(12) United States Patent
Hunter et al.

(10) Patent No.: US 11,553,968 B2
(45) Date of Patent: *Jan. 17, 2023

(54) APPARATUSES AND METHODS FOR REGISTERING A REAL-TIME IMAGE FEED FROM AN IMAGING DEVICE TO A STEERABLE CATHETER

(71) Applicant: Veran Medical Technologies, Inc., St. Louis, MO (US)

(72) Inventors: Mark Hunter, St. Louis, MO (US); Troy L. Holsing, Golden, CO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 561 days.

This patent is subject to a terminal disclaimer.

(21) Appl. No.: 16/682,132

(22) Filed: Nov. 13, 2019

(65) Prior Publication Data

US 2020/0078101 A1 Mar. 12, 2020

Related U.S. Application Data

(63) Continuation of application No. 15/208,534, filed on Jul. 12, 2016, now Pat. No. 10,624,701, which is a
(Continued)

(51) Int. Cl.
*A61B 1/00* (2006.01)
*A61B 34/20* (2016.01)
(Continued)

(52) U.S. Cl.
CPC .......... *A61B 34/20* (2016.02); *A61B 1/00009* (2013.01); *A61B 1/00057* (2013.01);
(Continued)

(58) Field of Classification Search
CPC . A61B 34/20; A61B 1/00009; A61B 1/00057; A61B 1/2676; A61B 5/061;
(Continued)

(56) References Cited

U.S. PATENT DOCUMENTS

| 466,609 A | 1/1892 | Lenox |
| 466,610 A | 1/1892 | Lewerth |

(Continued)

FOREIGN PATENT DOCUMENTS

| DE | 19751761 | 10/1998 |
| DE | 19725137 | 1/1999 |

(Continued)

OTHER PUBLICATIONS

Medical Industry Today, "New Navigational Aid Could Improve Hip Replacement Outcomes," Jul. 22, 1997.
(Continued)

*Primary Examiner* — Ashley K Buran
*Assistant Examiner* — Alisha B Diggs
(74) *Attorney, Agent, or Firm* — Forsgren Fisher; James M. Urzedowski; Daniel A. Tysver

(57) ABSTRACT

A method of registering a real-time image feed from an imaging device inserted into a steerable catheter using a navigation system is provided. The method includes inserting the imaging device into a working channel of the steerable catheter and generating a real-time image feed of one or more reference points, wherein the orientation of the reference points is known. The method further includes orienting a handle of the steerable catheter to a neutral position, displaying the real-time image feed on a display of the navigation system, and registering the real-time image feed to the steerable catheter by rotating the displayed image so that the reference points in the real-time image feed are matched to the known orientation of the reference points.

8 Claims, 30 Drawing Sheets

Related U.S. Application Data continuation of application No. 14/259,362, filed on Apr. 23, 2014, now abandoned.

(51) Int. Cl.
  *A61B 5/06* (2006.01)
  *A61B 5/113* (2006.01)
  *A61B 1/267* (2006.01)
  *A61B 90/00* (2016.01)

(52) U.S. Cl.
  CPC ............ *A61B 1/2676* (2013.01); *A61B 5/061* (2013.01); *A61B 5/062* (2013.01); *A61B 5/113* (2013.01); *A61B 5/1135* (2013.01); *A61B 2034/2051* (2016.02); *A61B 2034/2063* (2016.02); *A61B 2034/2065* (2016.02); *A61B 2090/364* (2016.02)

(58) Field of Classification Search
  CPC ....... A61B 5/062; A61B 5/113; A61B 5/1135; A61B 2034/2051; A61B 2034/2063; A61B 2034/2065; A61B 2090/364; A61B 1/000094
  See application file for complete search history.

(56) References Cited

U.S. PATENT DOCUMENTS

| | | | |
|---|---|---|---|
| 3,788,324 A | 1/1974 | Lim | |
| 4,421,106 A | 12/1983 | Uehara | |
| 4,583,538 A | 4/1986 | Onik et al. | |
| 5,053,042 A | 10/1991 | Bidwell | |
| 5,081,997 A | 1/1992 | Bosley, Jr. et al. | |
| 5,158,088 A | 10/1992 | Nelson et al. | |
| 5,186,174 A | 2/1993 | Schlondorff et al. | |
| 5,238,804 A | 8/1993 | Maskasky et al. | |
| 5,251,165 A | 10/1993 | James, III | |
| 5,251,635 A | 10/1993 | Dumoulin et al. | |
| 5,265,610 A | 11/1993 | Darrow et al. | |
| 5,295,493 A | 3/1994 | Radisch, Jr. | |
| 5,348,011 A | 9/1994 | Nessaiver | |
| 5,377,678 A | 1/1995 | Dumoulin et al. | |
| 5,391,199 A | 2/1995 | Ben-Haim | |
| 5,437,292 A | 8/1995 | Kipshidze et al. | |
| 5,483,691 A | 1/1996 | Heck et al. | |
| 5,483,961 A | 1/1996 | Kelly et al. | |
| 5,577,502 A | 11/1996 | Darrow et al. | |
| 5,581,183 A | 12/1996 | Lindstedt et al. | |
| 5,644,612 A | 7/1997 | Moorman et al. | |
| 5,671,739 A | 9/1997 | Darrow et al. | |
| 5,674,498 A | 10/1997 | Inoue et al. | |
| 5,718,241 A | 2/1998 | Ben-haim et al. | |
| 5,730,129 A | 3/1998 | Darrow et al. | |
| 5,740,808 A | 4/1998 | Panescu et al. | |
| 5,765,561 A | 6/1998 | Chen et al. | |
| 5,769,789 A | 6/1998 | Wang et al. | |
| 5,769,861 A | 6/1998 | Vilsmeier | |
| 5,771,306 A | 6/1998 | Stork et al. | |
| 5,787,886 A | 8/1998 | Kelly et al. | |
| 5,803,089 A | 9/1998 | Ferre et al. | |
| 5,814,022 A | 9/1998 | Antanavich et al. | |
| 5,814,066 A | 9/1998 | Spotnitz | |
| 5,833,608 A | 11/1998 | Acker | |
| 5,840,025 A | 11/1998 | Ben-haim | |
| 5,868,673 A | 2/1999 | Vesely | |
| 5,879,305 A | 3/1999 | Yock et al. | |
| 5,897,305 A | 4/1999 | Roddis | |
| 5,928,248 A | 7/1999 | Acker | |
| 5,951,461 A | 9/1999 | Nyo et al. | |
| 5,978,696 A | 11/1999 | Vomlehn et al. | |
| 6,016,439 A | 1/2000 | Acker | |
| 6,019,724 A | 2/2000 | Gronningsaeter et al. | |
| 6,026,173 A | 2/2000 | Svenson et al. | |
| 6,046,052 A | 4/2000 | Arter et al. | |
| 6,078,175 A | 6/2000 | Foo | |
| 6,122,538 A | 9/2000 | Sliwa, Jr. et al. | |
| 6,122,541 A | 9/2000 | Cosman et al. | |
| 6,132,396 A | 10/2000 | Antanavich et al. | |
| 6,139,508 A | 10/2000 | Simpson et al. | |
| 6,144,875 A | 11/2000 | Schweikard et al. | |
| 6,150,495 A | 11/2000 | Chou et al. | |
| 6,167,296 A | 12/2000 | Shahidi | |
| 6,173,201 B1 | 1/2001 | Front | |
| 6,188,355 B1 | 2/2001 | Gilboa | |
| 6,198,959 B1 | 3/2001 | Wang | |
| 6,201,987 B1 | 3/2001 | Dumoulin | |
| 6,226,543 B1 | 5/2001 | Gilboa et al. | |
| 6,226,548 B1 | 5/2001 | Foley et al. | |
| 6,233,476 B1 | 5/2001 | Strommer et al. | |
| 6,235,038 B1 | 5/2001 | Hunter et al. | |
| 6,236,875 B1 | 5/2001 | Bucholz et al. | |
| 6,246,896 B1 | 6/2001 | Dumoulin et al. | |
| 6,246,898 B1 | 6/2001 | Vesely et al. | |
| 6,253,770 B1 | 7/2001 | Acker et al. | |
| 6,254,550 B1 | 7/2001 | Mcnamara et al. | |
| 6,267,769 B1 | 7/2001 | Truwit | |
| 6,275,560 B1 | 8/2001 | Blake et al. | |
| 6,282,442 B1 | 8/2001 | Destefano et al. | |
| 6,285,902 B1 | 9/2001 | Kienzle, III et al. | |
| 6,298,259 B1 | 10/2001 | Kucharczyk et al. | |
| 6,314,310 B1 | 11/2001 | Ben-haim et al. | |
| 6,314,311 B1 | 11/2001 | Williams et al. | |
| 6,314,312 B1 | 11/2001 | Wessels et al. | |
| 6,317,616 B1 | 11/2001 | Glossop | |
| 6,317,619 B1 | 11/2001 | Boernert et al. | |
| 6,330,356 B1 | 12/2001 | Sundareswaran et al. | |
| 6,332,089 B1 | 12/2001 | Acker et al. | |
| 6,332,891 B1 | 12/2001 | Himes | |
| 6,335,617 B1 | 1/2002 | Osadchy et al. | |
| 6,335,623 B1 | 1/2002 | Damadian et al. | |
| 6,340,363 B1 | 1/2002 | Bolger et al. | |
| 6,347,240 B1 | 2/2002 | Foley et al. | |
| 6,348,058 B1 | 2/2002 | Melkent et al. | |
| 6,351,573 B1 | 2/2002 | Schneider | |
| 6,351,659 B1 | 2/2002 | Vilsmeier | |
| 6,361,759 B1 | 3/2002 | Frayne et al. | |
| 6,362,821 B1 | 3/2002 | Gibson et al. | |
| 6,368,331 B1 | 4/2002 | Front et al. | |
| 6,369,571 B1 | 4/2002 | Damadian et al. | |
| 6,369,574 B1 | 4/2002 | Ederlov et al. | |
| 6,373,998 B2 | 4/2002 | Thirion et al. | |
| 6,379,302 B1 | 4/2002 | Kessman et al. | |
| 6,380,732 B1 | 4/2002 | Gilboa | |
| 6,381,485 B1 | 4/2002 | Hunter et al. | |
| 6,402,762 B2 | 6/2002 | Hunter et al. | |
| 6,418,238 B1 | 7/2002 | Shiratani et al. | |
| 6,421,551 B1 | 7/2002 | Kuth et al. | |
| 6,424,856 B1 | 7/2002 | Vilsmeier et al. | |
| 6,425,865 B1 | 7/2002 | Salcudean et al. | |
| 6,430,430 B1 | 8/2002 | Gosche | |
| 6,434,416 B1 | 8/2002 | Mizoguchi et al. | |
| 6,434,507 B1 | 8/2002 | Clayton et al. | |
| 6,437,571 B1 | 8/2002 | Danby et al. | |
| 6,442,417 B1 | 8/2002 | Shahidi et al. | |
| 6,445,186 B1 | 9/2002 | Damadian et al. | |
| 6,445,943 B1 | 9/2002 | Ferre et al. | |
| 6,455,182 B1 | 9/2002 | Silver | |
| 6,461,372 B1 | 10/2002 | Jensen et al. | |
| 6,468,265 B1 | 10/2002 | Evans et al. | |
| 6,469,508 B1 | 10/2002 | Damadian et al. | |
| 6,470,066 B2 | 10/2002 | Takagi et al. | |
| 6,470,207 B1 | 10/2002 | Simon et al. | |
| 6,473,635 B1 | 10/2002 | Rasche | |
| 6,477,400 B1 | 11/2002 | Barrick | |
| 6,478,793 B1 | 11/2002 | Cosman et al. | |
| 6,478,802 B2 | 11/2002 | Kienzle, III et al. | |
| 6,483,801 B1 | 11/2002 | Novotny et al. | |
| 6,483,948 B1 | 11/2002 | Spink et al. | |
| 6,484,049 B1 | 11/2002 | Seeley et al. | |
| 6,485,413 B1 | 11/2002 | Boppart et al. | |
| 6,490,467 B1 | 12/2002 | Bucholz et al. | |
| 6,490,475 B1 | 12/2002 | Seeley et al. | |
| 6,490,477 B1 | 12/2002 | Zylka et al. | |

(56) References Cited

U.S. PATENT DOCUMENTS

| | | |
|---|---|---|
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,516,213 B1 | 2/2003 | Nevo |
| 6,517,485 B2 | 2/2003 | Olstad et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,947 B1 | 4/2003 | Dittmer et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,562,059 B2 | 5/2003 | Edwards et al. |
| 6,567,687 B2 | 5/2003 | Front et al. |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,593,884 B1 | 7/2003 | Gilboa et al. |
| 6,606,513 B2 | 8/2003 | Lardo et al. |
| 6,609,022 B2 | 8/2003 | Vilsmeier et al. |
| 6,615,155 B2 | 9/2003 | Gilboa |
| 6,636,757 B1 | 10/2003 | Jascob et al. |
| 6,650,924 B2 | 11/2003 | Kuth et al. |
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,702,780 B1 | 3/2004 | Gilboa et al. |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,774,624 B2 | 8/2004 | Anderson et al. |
| 6,782,287 B2 | 8/2004 | Grzeszczuk et al. |
| 6,796,988 B2 | 9/2004 | Melkent et al. |
| 6,799,569 B2 | 10/2004 | Danielsson et al. |
| 6,823,207 B1 | 11/2004 | Jensen et al. |
| 6,826,423 B1 | 11/2004 | Hardy et al. |
| 6,833,814 B2 | 12/2004 | Gilboa et al. |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,899,672 B2 | 5/2005 | Chin et al. |
| 6,907,281 B2 | 6/2005 | Grzeszczuk |
| 6,920,347 B2 | 7/2005 | Simon et al. |
| 6,925,200 B2 | 8/2005 | Wood et al. |
| 6,934,575 B2 | 8/2005 | Ferre et al. |
| 6,947,788 B2 | 9/2005 | Gilboa et al. |
| 6,968,224 B2 | 11/2005 | Kessman et al. |
| 6,978,166 B2 | 12/2005 | Foley et al. |
| 6,989,303 B2 | 1/2006 | Mori |
| 6,992,477 B2 | 1/2006 | Govari |
| 6,996,430 B1 | 2/2006 | Gilboa et al. |
| 7,015,859 B2 | 3/2006 | Anderson |
| 7,015,907 B2 | 3/2006 | Tek et al. |
| 7,035,683 B2 | 4/2006 | Guendel |
| 7,050,845 B2 | 5/2006 | Vilsmeier |
| 7,115,100 B2 | 10/2006 | Mcrury et al. |
| 7,130,700 B2 | 10/2006 | Gardeski et al. |
| 7,139,601 B2 | 11/2006 | Bucholz et al. |
| 7,153,297 B2 | 12/2006 | Peterson |
| 7,171,257 B2 | 1/2007 | Thomson |
| 7,174,201 B2 | 2/2007 | Govari et al. |
| 7,233,820 B2 * | 6/2007 | Gilboa ............ A61B 5/06 600/407 |
| 7,260,426 B2 | 8/2007 | Schweikard et al. |
| 7,300,428 B2 | 11/2007 | Ingenito |
| 7,339,587 B2 | 3/2008 | Kropfeld |
| 7,357,807 B2 | 4/2008 | Donohoe et al. |
| 7,366,562 B2 | 4/2008 | Dukesherer et al. |
| 7,371,067 B2 | 5/2008 | Anderson et al. |
| 7,398,116 B2 | 7/2008 | Edwards |
| 7,481,805 B2 | 1/2009 | Magnusson |
| 7,505,806 B2 | 3/2009 | Masutani et al. |
| 7,555,330 B2 | 6/2009 | Gilboa et al. |
| 7,594,925 B2 | 9/2009 | Danek et al. |
| 7,599,730 B2 | 10/2009 | Hunter et al. |
| 7,641,609 B2 | 1/2010 | Ohnishi et al. |
| 7,659,912 B2 | 2/2010 | Akimoto et al. |
| 7,697,972 B2 | 4/2010 | Verard et al. |
| 7,713,210 B2 | 5/2010 | Byrd et al. |
| 7,756,563 B2 | 7/2010 | Higgins et al. |
| 7,889,905 B2 | 2/2011 | Higgins et al. |
| 7,901,348 B2 | 3/2011 | Soper et al. |
| 7,962,193 B2 | 6/2011 | Edwards et al. |
| 7,969,143 B2 | 6/2011 | Gilboa |
| 7,985,187 B2 | 7/2011 | Wibowo et al. |
| 7,998,062 B2 | 8/2011 | Gilboa |
| 8,016,749 B2 | 9/2011 | Clerc et al. |
| 8,049,777 B2 | 11/2011 | Akimoto et al. |
| 8,064,669 B2 | 11/2011 | Higgins et al. |
| 8,096,957 B2 | 1/2012 | Conquergood et al. |
| 8,102,416 B2 | 1/2012 | Ito et al. |
| 8,150,138 B2 | 4/2012 | Ohnishi |
| 8,202,213 B2 | 6/2012 | Ito et al. |
| 8,214,015 B2 | 7/2012 | Macaulay et al. |
| 8,218,846 B2 | 7/2012 | Trumer et al. |
| 8,218,847 B2 | 7/2012 | Averbuch et al. |
| 8,219,179 B2 | 7/2012 | Ganatra et al. |
| 8,317,149 B2 | 11/2012 | Greenburg et al. |
| 8,317,726 B2 | 11/2012 | Timberlake et al. |
| 8,382,662 B2 | 2/2013 | Soper et al. |
| 8,428,328 B2 | 4/2013 | Averbuch et al. |
| 8,468,003 B2 | 6/2013 | Gibbs et al. |
| 8,473,032 B2 | 6/2013 | Averbuch |
| 8,494,246 B2 | 7/2013 | Trumer et al. |
| 8,494,612 B2 | 7/2013 | Vetter et al. |
| 8,611,983 B2 | 12/2013 | Glossop |
| 8,611,984 B2 | 12/2013 | Greenburg et al. |
| 8,632,461 B2 | 1/2014 | Glossop |
| 8,672,836 B2 | 3/2014 | Higgins et al. |
| 8,675,935 B2 | 3/2014 | Higgins et al. |
| 8,696,548 B2 | 4/2014 | Gilboa |
| 8,696,685 B2 | 4/2014 | Gilboa |
| 8,700,132 B2 | 4/2014 | Ganatra et al. |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Thomas, III et al. |
| 2001/0041835 A1 | 11/2001 | Front et al. |
| 2002/0044631 A1 | 4/2002 | Graumann et al. |
| 2002/0049375 A1 | 4/2002 | Strommer et al. |
| 2002/0049378 A1 | 4/2002 | Grzeszczuk et al. |
| 2002/0070970 A1 | 6/2002 | Wood et al. |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk |
| 2002/0085681 A1 | 7/2002 | Jensen |
| 2002/0143317 A1 | 10/2002 | Glossop |
| 2002/0161295 A1 | 10/2002 | Edwards et al. |
| 2003/0000535 A1 | 1/2003 | Robert, Jr. et al. |
| 2003/0004411 A1 | 1/2003 | Govari et al. |
| 2003/0016852 A1 | 1/2003 | Kaufman et al. |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0028107 A1 * | 2/2003 | Miller ............ A61B 5/6819 600/437 |

(56) References Cited

U.S. PATENT DOCUMENTS

| | | |
|---|---|---|
| 2003/0029464 A1 | 2/2003 | Chen et al. |
| 2003/0032878 A1 | 2/2003 | Shahidi |
| 2003/0040667 A1 | 2/2003 | Feussner et al. |
| 2003/0051733 A1 | 3/2003 | Kotmel et al. |
| 2003/0074011 A1 | 4/2003 | Gilboa et al. |
| 2003/0088179 A1 | 5/2003 | Seeley et al. |
| 2003/0125622 A1 | 7/2003 | Schweikard et al. |
| 2003/0130576 A1 | 7/2003 | Seeley et al. |
| 2003/0139663 A1 | 7/2003 | Graumann |
| 2003/0199785 A1 | 10/2003 | Hibner et al. |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0013548 A1 | 1/2004 | Seto et al. |
| 2004/0034300 A1 | 2/2004 | Verard et al. |
| 2004/0049121 A1 | 3/2004 | Yaron |
| 2004/0076259 A1 | 4/2004 | Jensen et al. |
| 2004/0091143 A1 | 5/2004 | Hu |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jascob et al. |
| 2004/0122311 A1 | 6/2004 | Cosman |
| 2004/0138548 A1 | 7/2004 | Strommer et al. |
| 2004/0152970 A1 | 8/2004 | Hunter et al. |
| 2004/0152974 A1 | 8/2004 | Solomon |
| 2004/0167393 A1 | 8/2004 | Solar et al. |
| 2004/0193042 A1 | 9/2004 | Scampini et al. |
| 2004/0210125 A1 | 10/2004 | Chen et al. |
| 2004/0249267 A1 | 12/2004 | Gilboa |
| 2005/0010099 A1 | 1/2005 | Raabe et al. |
| 2005/0020878 A1 | 1/2005 | Ohnishi et al. |
| 2005/0020900 A1 | 1/2005 | Yngvesson et al. |
| 2005/0027186 A1 | 2/2005 | Chen et al. |
| 2005/0033149 A1 | 2/2005 | Strommer et al. |
| 2005/0065433 A1 | 3/2005 | Anderson |
| 2005/0085718 A1 | 4/2005 | Shahidi |
| 2005/0085793 A1 | 4/2005 | Glossop |
| 2005/0107679 A1 | 5/2005 | Geiger et al. |
| 2005/0107688 A1 | 5/2005 | Strommer |
| 2005/0113809 A1 | 5/2005 | Melkent et al. |
| 2005/0137661 A1 | 6/2005 | Sra |
| 2005/0143651 A1 | 6/2005 | Verard et al. |
| 2005/0169510 A1 | 8/2005 | Zuhars et al. |
| 2005/0182295 A1 | 8/2005 | Soper et al. |
| 2005/0182319 A1 | 8/2005 | Glossop |
| 2005/0187482 A1 | 8/2005 | O'Brien et al. |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1 | 1/2006 | Saracen |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | Von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0142978 A1 | 6/2006 | Suenbuel et al. |
| 2006/0173269 A1 | 8/2006 | Glossop |
| 2006/0173291 A1 | 8/2006 | Glossop |
| 2006/0184016 A1 | 8/2006 | Glossop |
| 2006/0189867 A1 | 8/2006 | Revie et al. |
| 2006/0247511 A1 | 11/2006 | Anderson |
| 2006/0258933 A1 | 11/2006 | Ellis et al. |
| 2006/0270976 A1 | 11/2006 | Savage et al. |
| 2007/0032723 A1 | 2/2007 | Glossop |
| 2007/0038058 A1 | 2/2007 | West et al. |
| 2007/0066887 A1 | 3/2007 | Mire et al. |
| 2007/0078334 A1 | 4/2007 | Scully et al. |
| 2007/0110289 A1 | 5/2007 | Fu et al. |
| 2007/0129629 A1 | 6/2007 | Beauregard et al. |
| 2007/0167714 A1 | 7/2007 | Kiraly et al. |
| 2007/0167744 A1 | 7/2007 | Beauregard et al. |
| 2007/0225559 A1 | 9/2007 | Clerc et al. |
| 2007/0232896 A1 | 10/2007 | Gilboa et al. |
| 2007/0244355 A1 | 10/2007 | Shaw |
| 2007/0249896 A1 | 10/2007 | Goldfarb et al. |
| 2007/0276180 A1 | 11/2007 | Greenburg et al. |
| 2008/0047334 A1 | 2/2008 | Baba et al. |
| 2008/0071142 A1 | 3/2008 | Gattani et al. |
| 2008/0071143 A1 | 3/2008 | Gattani et al. |
| 2008/0118135 A1 | 5/2008 | Averbuch et al. |
| 2008/0123910 A1 | 5/2008 | Zhu |
| 2008/0125760 A1 | 5/2008 | Gilboa |
| 2008/0132757 A1 | 6/2008 | Tgavalekos |
| 2008/0140114 A1 | 6/2008 | Edwards et al. |
| 2008/0167639 A1 | 7/2008 | Gilboa |
| 2008/0221442 A1 | 9/2008 | Tolkowsky et al. |
| 2008/0247622 A1 | 10/2008 | Aylward et al. |
| 2008/0255416 A1 | 10/2008 | Gilboa |
| 2008/0262297 A1 | 10/2008 | Gilboa et al. |
| 2008/0262342 A1 | 10/2008 | Averbruch |
| 2008/0262430 A1 | 10/2008 | Anderson et al. |
| 2008/0269561 A1 | 10/2008 | Banik et al. |
| 2008/0287803 A1 | 11/2008 | Li et al. |
| 2009/0054908 A1 | 2/2009 | Zand et al. |
| 2009/0088600 A1 | 4/2009 | Meloul |
| 2009/0156895 A1 | 6/2009 | Higgins et al. |
| 2009/0156951 A1 | 6/2009 | Averbuch |
| 2009/0209817 A1 | 8/2009 | Averbuch |
| 2009/0227861 A1 | 9/2009 | Ganatra et al. |
| 2009/0240140 A1 | 9/2009 | Fitelzon et al. |
| 2009/0240198 A1 | 9/2009 | Averbuch |
| 2009/0284255 A1 | 11/2009 | Zur |
| 2010/0020161 A1 | 1/2010 | Bertrams et al. |
| 2010/0034449 A1 | 2/2010 | Averbuch et al. |
| 2010/0036241 A1 | 2/2010 | Mayse et al. |
| 2010/0041949 A1* | 2/2010 | Tolkowsky ...... A61B 17/12104 600/117 |
| 2010/0048993 A1 | 2/2010 | Shidara |
| 2010/0160733 A1 | 6/2010 | Gilboa |
| 2011/0065993 A1 | 3/2011 | Belson et al. |
| 2012/0046521 A1 | 2/2012 | Hunter et al. |
| 2012/0059220 A1 | 3/2012 | Holsing et al. |
| 2012/0059248 A1 | 3/2012 | Holsing et al. |
| 2012/0065481 A1 | 3/2012 | Hunter et al. |
| 2012/0071752 A1 | 3/2012 | Sewell et al. |
| 2012/0071753 A1 | 3/2012 | Hunter et al. |
| 2012/0123296 A1 | 5/2012 | Hashimshony et al. |
| 2012/0289825 A1 | 11/2012 | Rai et al. |
| 2013/0096572 A1 | 4/2013 | Donhowe et al. |
| 2014/0278108 A1 | 9/2014 | Kerrigan et al. |
| 2015/0209551 A1 | 7/2015 | Burdette et al. |
| 2016/0005168 A1 | 1/2016 | Merlet |

FOREIGN PATENT DOCUMENTS

| | | |
|---|---|---|
| DE | 19829224 | 1/2000 |
| DE | 19909816 | 5/2000 |
| DE | 10000937 | 8/2001 |
| DE | 102005010010 | 9/2005 |
| DE | 102004030836 | 1/2006 |
| DE | 102005026251 | 1/2006 |
| DE | 102005038394 | 3/2006 |
| DE | 102005050286 | 4/2006 |
| DE | 102004058122 | 7/2006 |
| EP | 0501993 | 9/1992 |
| EP | 0869745 | 10/1998 |
| EP | 900048 | 3/1999 |

(56) References Cited

FOREIGN PATENT DOCUMENTS

| | | |
|---|---|---|
| EP | 0928600 | 7/1999 |
| EP | 977510 | 2/2000 |
| EP | 1079240 | 2/2001 |
| EP | 1152706 | 11/2001 |
| EP | 1181897 | 2/2002 |
| EP | 1374792 | 1/2004 |
| EP | 1374793 | 1/2004 |
| EP | 1504726 | 2/2005 |
| EP | 1519140 | 3/2005 |
| EP | 1523951 | 4/2005 |
| EP | 1561423 | 8/2005 |
| EP | 1629774 | 3/2006 |
| EP | 1629789 | 3/2006 |
| EP | 2380550 | 10/2011 |
| FR | 2876273 | 4/2006 |
| JP | 2000023941 | 1/2000 |
| WO | WO9210972 | 7/1992 |
| WO | WO9424933 | 11/1994 |
| WO | WO9501757 | 1/1995 |
| WO | WO9608209 | 3/1996 |
| WO | WO9610949 | 4/1996 |
| WO | WO9626672 | 9/1996 |
| WO | WO9729699 | 8/1997 |
| WO | WO9729709 | 8/1997 |
| WO | WO9836684 | 8/1998 |
| WO | WO9916352 | 4/1999 |
| WO | WO9927839 | 6/1999 |
| WO | WO9943253 | 9/1999 |
| WO | WO0016684 | 3/2000 |
| WO | WO0028911 | 5/2000 |
| WO | WO0047103 | 8/2000 |
| WO | WO0049958 | 8/2000 |
| WO | WO0057767 | 10/2000 |
| WO | WO0069335 | 11/2000 |
| WO | WO0101845 | 1/2001 |
| WO | WO0137748 | 5/2001 |
| WO | WO0162134 | 8/2001 |
| WO | WO0164124 | 9/2001 |
| WO | WO0176496 | 10/2001 |
| WO | WO0176497 | 10/2001 |
| WO | WO0187136 | 11/2001 |
| WO | WO0193745 | 12/2001 |
| WO | WO0200093 | 1/2002 |
| WO | WO0200103 | 1/2002 |
| WO | WO0219936 | 3/2002 |
| WO | WO0222015 | 3/2002 |
| WO | WO0224051 | 3/2002 |
| WO | WO02056770 | 7/2002 |
| WO | WO02064011 | 8/2002 |
| WO | WO02082375 | 10/2002 |
| WO | WO02098273 | 12/2002 |
| WO | WO2004046754 | 6/2004 |
| WO | WO2004062497 | 7/2004 |
| WO | WO2005016166 | 2/2005 |
| WO | WO2005070318 | 8/2005 |
| WO | WO2005077293 | 10/2005 |
| WO | WO2005101277 | 10/2005 |
| WO | WO2005111942 | 11/2005 |
| WO | WO2006002396 | 1/2006 |
| WO | WO2006005021 | 1/2006 |
| WO | WO06027781 | 3/2006 |
| WO | WO06039009 | 4/2006 |
| WO | WO2006039009 | 4/2006 |
| WO | WO06051523 | 5/2006 |
| WO | WO2006051523 | 5/2006 |
| WO | WO2006090141 | 8/2006 |
| WO | WO2007002079 | 1/2007 |
| WO | WO2007031314 | 3/2007 |
| WO | WO2007033206 | 3/2007 |
| WO | WO2007062051 | 5/2007 |
| WO | WO2007084893 | 7/2007 |
| WO | WO2009158578 | 12/2009 |
| WO | WO2010111629 A2 | 9/2010 |
| WO | WO2012024686 | 2/2012 |

OTHER PUBLICATIONS

European Patent Office, Extended Search Report issued for EP 11818898.6, 6 pages Dec. 20, 2013.
Patent Cooperation Treaty, International Search Report and Written Opinion from PCT/US06/35548, dated Aug. 20, 2007, 7 pages.
Highlights from Presentation of 5th Joint Meeting of European Assn, for Cardio-Thoracic Surgery and European Society of Thoracic Surgeons "Evidence for Fleece-Bound Sealants in Cardiothoracic Surgery" Sep. 9-13, 2006 Sep. 9, 2006.
Moore, E. et al., Needle Aspiration Lung Biopsy: Re-evaluation of the blood patch technique in an equine model, Radiology, 196(1) Jul. 1, 1995.
FDA Approves Lung Sealant, May 31, 2000 [online], [retried Oct. 17, 2008 from Internet]; http://www.meds.com/archive/mol-cancer/2000/05/msg01329.html Aug. 31, 2000.
Jul. 2, 2018 USPTO Office Action (U.S. Appl. No. 15/208,534)—Our Matter 5702.
Patent Cooperation Treaty, International Search Report issued for PCT/US15/27273, dated Jul. 15, 2015, 6 pages.
Patent Cooperation Treaty, International Search Report issued for PCT/US11/48669, dated Apr. 9, 2012, 7 pages, Apr. 9, 2012.
Jan. 12, 2016 USPTO Office Action (U.S. Appl. No. 14/259,362)—Our Matter 5696.
Mar. 5, 2019 USPTO Office Action (U.S. Appl. No. 15/208,534)—Our Matter 5702.

\* cited by examiner

INSPIRATION

DEFORMATION VECTORS CALCULATED FROM INSPIRATION TO EXPIRATION

EXPIRATION

HYBRID INSPIRATION-EXPIRATION

APPARATUSES AND METHODS FOR REGISTERING A REAL-TIME IMAGE FEED FROM AN IMAGING DEVICE TO A STEERABLE CATHETER

CROSS-REFERENCE TO RELATED APPLICATIONS

The present application is a continuation of U.S. Ser. No. 15/208,534, filed on Jul. 12, 2016, which in turn is a continuation of U.S. Ser. No. 14/259,362, filed on Apr. 23, 2014. Both of these applications are hereby incorporated by reference in their entireties.

BACKGROUND

The invention relates generally to medical devices and particularly to apparatuses and methods associated with a range of image guided medical procedures for detecting, sampling, staging and/or treating target tissues in the lungs of a patient.

Image guided surgery (IGS), also known as image guided intervention (IGI), enhances a physician's ability to locate instruments within anatomy during a medical procedure. IGS can include 2-dimensional (2D), 3-dimensional (3D), and 4-dimensional (4D) applications. The fourth dimension of IGS can include multiple parameters either individually or together such as time, motion, electrical signals, pressure, airflow, blood flow, respiration, heartbeat, and other patient measured parameters.

Although significant improvements have been made in these fields, a need remains for improved medical devices and procedures for visualizing, accessing, locating, real-time confirming while sampling and manipulating a target tissue.

SUMMARY OF THE INVENTION

Among the various aspects of the present invention may be noted apparatuses for use in and methods associated with medical procedures; such apparatuses and methods, for example, may include apparatuses and methods that enhance a physician's ability to confirm the location of a target tissue within a patient during a medical procedure, such as image guided surgery (IGS) or image guided intervention (IGI) and such apparatuses and methods may further include apparatuses and methods that facilitate visualizing, accessing, locating, and manipulating the targeted tissue.

Briefly, therefore, one aspect of the present invention is a method of confirming the location of a target tissue within a patient using a navigation system. The navigation system comprises a localization device, a display, and a pre-acquired image dataset of an airway of the patient. The navigation system is adapted to display images from the image dataset and to provide location information of a medical device within the patient in relation to a patient tracking device comprising a plurality of localization elements. The method comprises affixing the patient tracking device to an external surface of the patient, tracking the location of the patient tracking device using the navigation system, displaying an image from the image dataset on the display, wherein the displayed image is registered to the patient tracking device, and determining an initial location of the target tissue in the image dataset and navigating a steerable catheter through the airway of the patient to a position proximate the initial location. The steerable catheter has a proximal end portion and a distal end portion terminating in a tip, a working channel extending there between, and a localization element disposed proximate the distal end portion thereof. The method further comprises tracking the location of the localization element of the steerable catheter in the airway using the navigation system, generating information regarding the presence of the target tissue using a tissue sensing device inserted into the working channel of the steerable catheter, and determining a confirmed location of the target tissue using the generated information regarding the presence of the target tissue and the tracked location of the localization element. The method further comprises recording the confirmed location of the target tissue and, displaying the confirmed location of the target tissue on the display of the navigation system in an image from the image dataset.

Another aspect of the present invention is a method of navigating a percutaneous needle to a target tissue within a patient using a navigation system. The navigation system comprises a localization device, a display, and a pre-acquired image dataset of an airway of the patient. The navigation system is adapted to display images from the image dataset and to provide location information of a medical device within the patient in relation to a patient tracking device comprising a plurality of localization elements. The method comprises affixing the patient tracking device to an external surface of the patient, tracking the location of the patient tracking device using the navigation system to monitor the respiratory state of the patient, and displaying an image from the image dataset on the display as a function of the monitored respiratory state, wherein the displayed image is registered to the patient tracking device. The method further comprises determining an initial location of the target tissue in the image dataset and navigating a steerable catheter through the airway of the patient to a position proximate the initial location. The steerable catheter has a proximal end portion and a distal end portion terminating in a tip, a working channel extending there between, and a localization element disposed proximate the distal end portion thereof. The method further comprises tracking the location of the localization element of the steerable catheter in the airway using the navigation system, generating one or more images of the target tissue using an imaging device inserted into the working channel of the steerable catheter, and determining a confirmed location of the target tissue in relation to the patient tracking device using the generated images and the tracked location of the localization element. The method further comprises recording the confirmed location of the target tissue, the recording comprising four-dimensional data comprising a three-dimensional location of the confirmed target tissue in relation to the patient tracking device and the respiratory state of the patient at the time the location of the target tissue was confirmed and applying the confirmed location of the target tissue to an image from the image dataset depicting the airway at the respiratory state of the patient at the time the location of the target tissue was confirmed. The method further comprises displaying the confirmed location of the target tissue on the display of the navigation system in an image from the image dataset, the displayed image depicting the airway at the respiratory state of the patient at the time the location of the target tissue was confirmed. Furthermore, the method comprises displaying a trajectory of a percutaneous device from an entry point on the patient's body to the confirmed location on the display of the navigation system, wherein the percutaneous device includes a localization element, inserting the percutaneous device into the patient and navigating the percutaneous device to the confirmed location, and intercepting the target tissue at the confirmed location.

Another aspect of the present invention is a method of navigating a medical device to the confirmed location of the target tissue using indicia indicating the confirmed location of the target tissue and/or indicia indicating the location of the medical device. Thus the method may include displaying the confirmed location of the target tissue on the display of the navigation system without requiring that an image of the image dataset be displayed. This method of navigating a medical device to the confirmed location of the target tissue does not require re-registering one or more image datasets to the patient so long as the patient tracking device affixed to the patient does not move or the patient does not move relative to an electromagnetic field generator of the navigation system. Therefore, this method does not require displaying a hybrid "Inspiration-Expiration" 3D airway model, one or more images from one or more image datasets, a navigation pathway, and/or a real-time image feed from a bronchoscopic video camera, in order to permit a physician or other healthcare professional in navigating a medical device to the confirmed location of the target tissue.

Another aspect of the present invention is directed to a method of registering a real-time image feed from an imaging device inserted into a steerable catheter using a navigation system comprising a display. The steerable catheter comprises an elongate flexible shaft having a proximal end portion, a distal end portion terminating in a tip, a working channel extending therebetween, and handle attached to the proximal end portion of the flexible shaft. The method comprises inserting the imaging device into the working channel of the steerable catheter, generating a real-time image feed of one or more reference points, wherein the orientation of the reference points is known, orienting the handle of the steerable catheter to a neutral position, displaying the real-time image feed on the display, and registering the real-time image feed to the steerable catheter by rotating the displayed image so that the reference points in the real-time image feed are matched to the known orientation of the reference points.

Another aspect of the present invention is directed to a method of enhancing registration of the real-time image feed of a bronchoscopic video camera by correcting image distortion in the real time image feed. For example, bronchoscopic video cameras typically include fish-eye lenses which increase the field of view of the bronchoscopic video camera thus providing the physician or other healthcare professional with a larger view of the airway of the patient. However, the fish-eye lenses introduce barrel distortion into the real-time image feed. Due to this barrel distortion, the interpretation of the real-time image feed may be compromised. Correcting for this image distortion in the real-time image feed provides a more accurate depiction of the airway of the patient, thus permitting an enhanced registration of the real-time image feed.

Yet another aspect of the present invention is directed to the construction and use of a hybrid "Inspiration-Expiration" 3D airway model. The hybrid "Inspiration-Expiration" 3D airway model may be used to reduce or eliminate errors in registration. Constructing the hybrid "Inspiration-Expiration" 3D airway model comprises calculating a population of deformation vector fields, wherein the deformation vector field(s) comprise vectors from one or more voxels in inspiration images or in an inspiration 3D airway model to one or more corresponding voxels in expiration images or in an expiration 3D airway model. After the deformation vector field is calculated, the inspiration images and/or the inspiration 3D airway model may be deformed to the expiration state of the patient using the deformation vector field. Accordingly, the voxels in the inspiration images and/or inspiration 3D airway model are deformed to match the location, shape, and orientation of the airways of the patient at expiration. This results in the hybrid "Inspiration-Expiration" 3D airway model, wherein the hybrid "Inspiration-Expiration" 3D airway model contains the structural information of the airways of patient depicted in the inspiration images and/or inspiration 3D airway model. However, this structural information is now more closely matched to the location, shape, and orientation of the airways of the patient depicted in the expiration images and/or expiration 3D airway model. Accordingly, the deformation vectors represent a change in location of the structure of the airway and a change in shape of the structure of the airway from inspiration to expiration.

Yet another aspect of the present invention is directed to a method of injecting dye into a target tissue using a needle inserted into the working channel of a steerable catheter or using a needle inserted into the working channel of a percutaneous needle. Thus, when sampling the target tissue using a medical device inserted into the steerable catheter or percutaneous needle, the presence of dye in the sample provides an indication that the correct target tissue was sampled. This may be helpful, for example, in lung resections where there is significant movement of the lungs of the patient. For example, during lung resections there may be a gap between the chest wall and the lung and the physician or other healthcare profession may use a rigid scope to enter into the patient. Because the target tissue was previously dyed using a needle inserted into the working channel of steerable catheter or using a needle inserted into the working channel of the percutaneous needle, the physician or other healthcare professional may be able to visually see the dye. This may assist the physician or healthcare professional in sampling and/or treating the correct target tissue.

Yet another aspect of the present invention is directed to a method of simulating and/or displaying a variety of image views using a navigation system based on the position and orientation (POSE) of a localization element in a steerable catheter, percutaneous device, and/or some other medical device. For example, the navigation system may be able to simulate and/or display axial images, coronal images, oblique images, orthogonal image slices, oblique or off-axis image slices, volume rendered images, segmented images, fused modality images, maximum intensity projection (MIPS) images, video, and video enhanced images. To simulate these views, the navigation system may modify one or more images from an image dataset using known image manipulation techniques. The images in the image dataset may be fluoroscopic images, ultrasound images, to computed tomography (CT) images, fused computed tomography—positron emission tomography (CT/PET) images, magnetic resonance imaging (MRI) images, etc.

BRIEF DESCRIPTION OF THE DRAWINGS

The details of the present invention, both as to its construction and operation can best be understood with reference to the accompanying drawings, in which like numerals refer to like parts, and in which.

DETAILED DESCRIPTION

Figure 1:
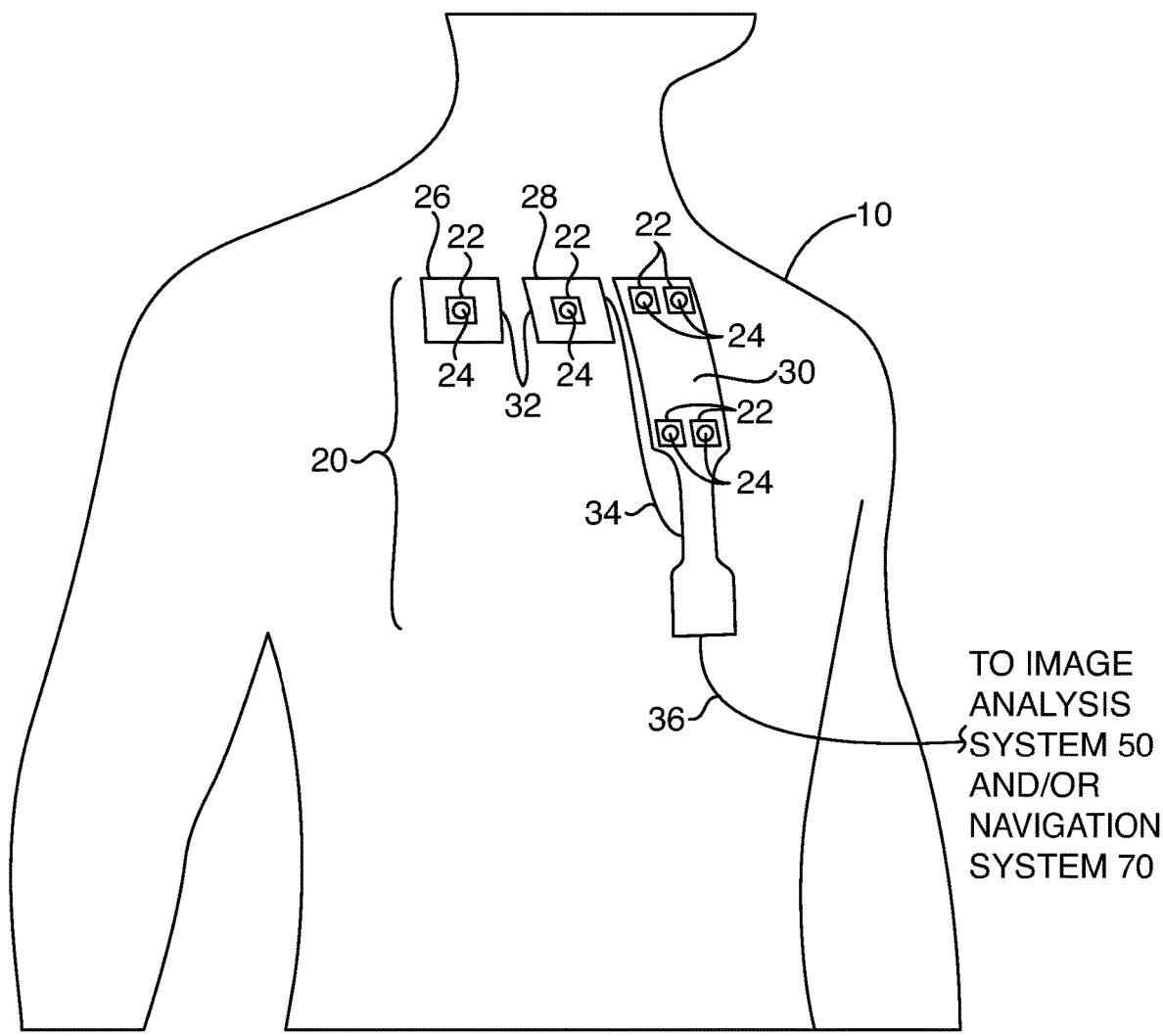
FIG. 1 left perspective view of a patient tracking device on a patient according to an embodiment of the invention.

The accompanying Figures and this description depict and describe embodiments of a navigation system (and related methods and devices) in accordance with the present invention, and features and components thereof. It should also be noted that any references herein to front and back, right and left, top and bottom and upper and lower are intended for convenience of description, not to limit the present invention or its components to any one positional or spatial orientation.

Those of skill in the art will appreciate that in the detailed description below, certain well known components and assembly techniques have been omitted so that the present methods, apparatuses, and systems are not obscured in unnecessary detail.

With larger volumes of patients expected to obtain lung cancer screening, obtaining definitive diagnoses may avoid numerous unneeded lung resections as about only 4% of patients from lung cancer screening are typically found to have a malignancy. However, peripheral target tissues (e.g., nodule, lesion, lymph node, tumor, etc.) that are smaller than 2 cm in size still present a difficult problem to solve. Typical bronchoscopes that are designed mainly for central airway inspection will be limited to the extent they can travel due to their large diameters before becoming wedged in the airway of the patient. Thus, to affect the 5 and 10 year survival rate of patient's that have target tissues which may be less than 2 cm in size, the apparatuses and methods as described herein allow for enhanced target tissue analysis for staging, intercepting target tissues in the periphery of the lungs that may not be accessible via airways, obtaining larger and higher quality tissue samples for testing, and provide a streamlined patient flow. Accordingly, the apparatuses and methods described herein enable a physician or other healthcare professional to initially determine the location of a target tissue and to confirm the location of the target tissue. In one embodiment, a hybrid "Inspiration-Expiration" 3D model may be used to provide patient specific 4D respiratory models which address peripheral respiratory motion. In certain patients, portions of the lungs including the upper lobes may move, on average, 15 mm between inspiration and expiration. Using a steerable catheter with an imaging device, such as a radial endobronchial ultrasound (EBUS) device inserted therein, a physician or other healthcare professional can determine a confirmed location of the target tissue. Additionally, apparatuses and methods described herein enable a physician or other healthcare professional to transition to a percutaneous approach to the target tissue, if needed. If the physician or other healthcare professional is unable to reach the target tissue for any reason, including but not limited to, the target tissue being below the surface of the airway (i.e., sub-surface target tissue), no airway proximate the target tissue, the pathway to the target tissue is very tortuous, or larger or additional tissue sample from a core biopsy is desired, the physician or other healthcare professional may insert navigated percutaneous needles to the confirmed location of the target tissue. Thus it will be understood that the apparatuses and methods described herein may be used to intercept target tissue(s) in the airway, on the wall of the airway, in the wall of the airway, and/or beyond the wall of the airway. That is, the apparatuses and methods described herein may be used to intercept target tissue(s) not only inside the airway, but may intercept target tissue(s) and other anatomical structures inside and/or beyond the wall of the airway. Thus in certain embodiments, sub-surface target tissue(s) may be intercepted.

Additionally, the apparatuses and methods described herein provide easy to understand localization information to the physician or other healthcare professional, as well as display the preferred entry site and trajectory views of the percutaneous needle that are aligned to the target tissue. Once aligned, the physician or other healthcare professional may direct the percutaneous needle along the trajectory to the target tissue while viewing a display of the location of the tip of percutaneous needle on a navigation system as described herein. The physician or other healthcare professional may then intercept the target tissue in a variety of ways, including, but not limited to, performing a standard core biopsy, an aspiration, and/or delivering therapy using a variety of medical devices inserted through the percutaneous needle.

As shown in FIG. 1, an apparatus according to an embodiment of the invention includes patient tracking device (PTD) 20 comprising two or more markers 22 and two or more localization elements 24 proximate markers 22. Markers 22 are visible in images captured by an imaging device and the position and orientation (POSE) of localization elements 24 may be tracked by a localization device in an image analysis system and/or a navigation system. PTD 20 comprises a population of separate pads 26, 28, 30, each of which may include one or more markers 22 and localization elements 24 proximate markers 22. First and second pads 26, 28 may each include one marker 22 and one localization element 24. Third pad 30 may include four markers 22 and four localization elements 24 located proximate the periphery of third pad 30. Additionally, wires 32, 34, 36 are used to connect localization elements 24 in each of first, second, and third pads 26, 28, 30 to image analysis system 50 (see FIG. 2) and/or navigation system 70 (see FIG. 3). In alternative embodiments, localization elements 24 may be wirelessly connected to navigation system 70. FIG. 1 illustrates PTD 20 having six markers 22 and six localization elements 24, but any number of two or more markers 22 and localization elements 24 can be used. Patient tracking device (PTD) 20 can be coupled to a dynamic body such as, for example, a selected dynamic portion of the anatomy of a patient 10.

Markers 22 are constructed of a material that can be viewed on an image, such as, for example, X-ray images or CT images. In certain embodiments, markers 22 can be, for example, radiopaque such that they are visible via fluoroscopic imaging. In other embodiments, for example, markers 22 may be echogenic such that they are visible via ultrasonic imaging. In yet other embodiments, markers 22 may be both radiopaque and echogenic. In certain embodiments, for example, localization elements 24 comprise six (6) degree of freedom (6DOF) electromagnetic coil sensors. In other embodiments, localization elements 24 comprise five (5) degree of freedom (5DOF) electromagnetic coil sensors. In other embodiments, localization elements 24 comprise other localization devices such as radiopaque markers that are visible via fluoroscopic imaging and echogenic patterns that are visible via ultrasonic imaging. In yet other embodiments, localization elements 24 can be, for example, infrared light emitting diodes, and/or optical passive reflective markers. Localization elements 24 can also be, or be integrated with, one or more fiber optic localization (FDL) devices.

While PTD 20 is shown comprising a population of separate pads containing markers 22 and localization elements 24, in certain embodiments, PTD 20 may comprise one pad containing markers 22 and localization elements 24. In another embodiment, for example, PTD 20 may include markers 22 but not localization elements 24. In another embodiment, for example, PTD 20 may include localization elements 24 but not markers 22. In various embodiments, markers 22 and localization elements 24 can be the same device. In certain embodiments, for example, localization elements 24 may function or serve as markers 22. PTD 20 can be a variety of different shapes and sizes. For example, in one embodiment PTD 20 is substantially planar, such as in the form of a pad that can be disposed at a variety of locations on a patient's 10 body. PTD 20 can be coupled to patient 10 with adhesive, straps, hook and pile, snaps, or any other suitable coupling method. In another embodiment the PTD can be a catheter type device with a pigtail or anchoring mechanism that allows it to be attached to an internal organ or along a vessel.

As described more fully elsewhere herein, an image analysis system is configured to receive image data associated with the dynamic body generated during a pre-surgical or pre-procedural first time interval. The image data can include an indication of a position of each of markers 22 for multiple instants in time during the first time interval. Then a navigation system can also receive position data associated with localization elements 24 during a second time interval in which a surgical procedure or other medical procedure is being performed. The navigation system can use the position data received from localization elements 24 to determine a distance between the localization elements 24 for a given instant in time during the second time interval. The navigation system can also use the image data to determine the distance between markers 22 for a given instant in time during the first time interval. The navigation system can then find a match between an image where the distance between markers 22 at a given instant in time during the first time interval is the same or substantially the same as the distance between localization elements 24 associated with those markers 22 at a given instant in time during the medical procedure, or second time interval. Additionally, the navigation system can determine a sequence of motion of the markers and match this sequence of motion to the recorded motion of the markers over the complete procedure or significant period of time. Distance alone between the markers may not be sufficient to match the patient space to image space in many instances, the system may also determine the direction the markers are moving and the range and speed of this motion to find the appropriate sequence of motion for a complex signal or sequence of motion by the patient.

A physician or other healthcare professional can use the images selected by the navigation system during a medical procedure performed during the second time interval. For example, when a medical procedure is performed on a targeted anatomy of a patient, such as a heart or lung, the physician may not be able to utilize an imaging device during the medical procedure to guide him to the targeted area within the patient. Accordingly, PTD 20 can be positioned or coupled to the patient proximate the targeted anatomy prior to the medical procedure, and pre-procedural images can be taken of the targeted area during a first time interval. Markers 22 of PTD 20 can be viewed with the image data, which can include an indication of the position of markers 22 during a given path of motion of the targeted anatomy (e.g., the heart) during the first time interval. Such motion can be due, for example, to inspiration (i.e., inhaling) and expiration (i.e., exhaling) of the patient, or due to the heart beating. During a medical procedure, performed during a second time interval, such as a procedure on a heart or lung, the navigation system receives data from localization elements 24 associated with a position of localization elements 24 at a given instant in time during the medical procedure (or second time interval). The distance between selected pairs of markers 22 can be determined from the image data and the distance, range, acceleration, and speed between corresponding selected pairs of localization elements 24 can be determined based on the position and orientation (POSE) data for given instants in time. Accordingly, the range of motion and speed of markers 22 can be calculated.

Because localization elements 24 are proximate the location of markers 22, the distance between a selected pair of localization elements 24 can be used to determine an intra-procedural distance between the pair of corresponding markers 22. An image from the pre-procedural image data taken during the first time interval can then be selected where the distance between the pair of selected markers 22 in that image corresponds with or closely approximates the same distance determined using localization elements 24 at a given instant in time during the second time interval. This process can be done continuously during the medical procedure, producing simulated real-time, intra-procedural images illustrating the orientation and shape of the targeted anatomy as a catheter, sheath, needle, forceps, guidewire, fiducial delivery devices, therapy device, or similar medical device(s) is/are navigated to the targeted anatomy. Thus, during the medical procedure, the physician can view selected image(s) of the targeted anatomy that correspond to and simulate real-time movement of the anatomy. In addition, during a medical procedure being performed during the second time interval, such as navigating a catheter or other medical device or component thereof to a targeted anatomy, the location(s) of a localization element (e.g., an electromagnetic coil sensor) coupled to the catheter during the second time interval can be superimposed on an image of a catheter. The superimposed image(s) of the catheter can then be superimposed on the selected image(s) from the first time interval, providing simulated real-time images of the catheter location relative to the targeted anatomy. This process and other related methods are described in U.S. Pat. No. 7,398,116, entitled Methods, Apparatuses, and Systems Useful in Conducting Image Guided Interventions, filed Aug. 26, 2003, which is hereby incorporated by reference.

Figure 2:
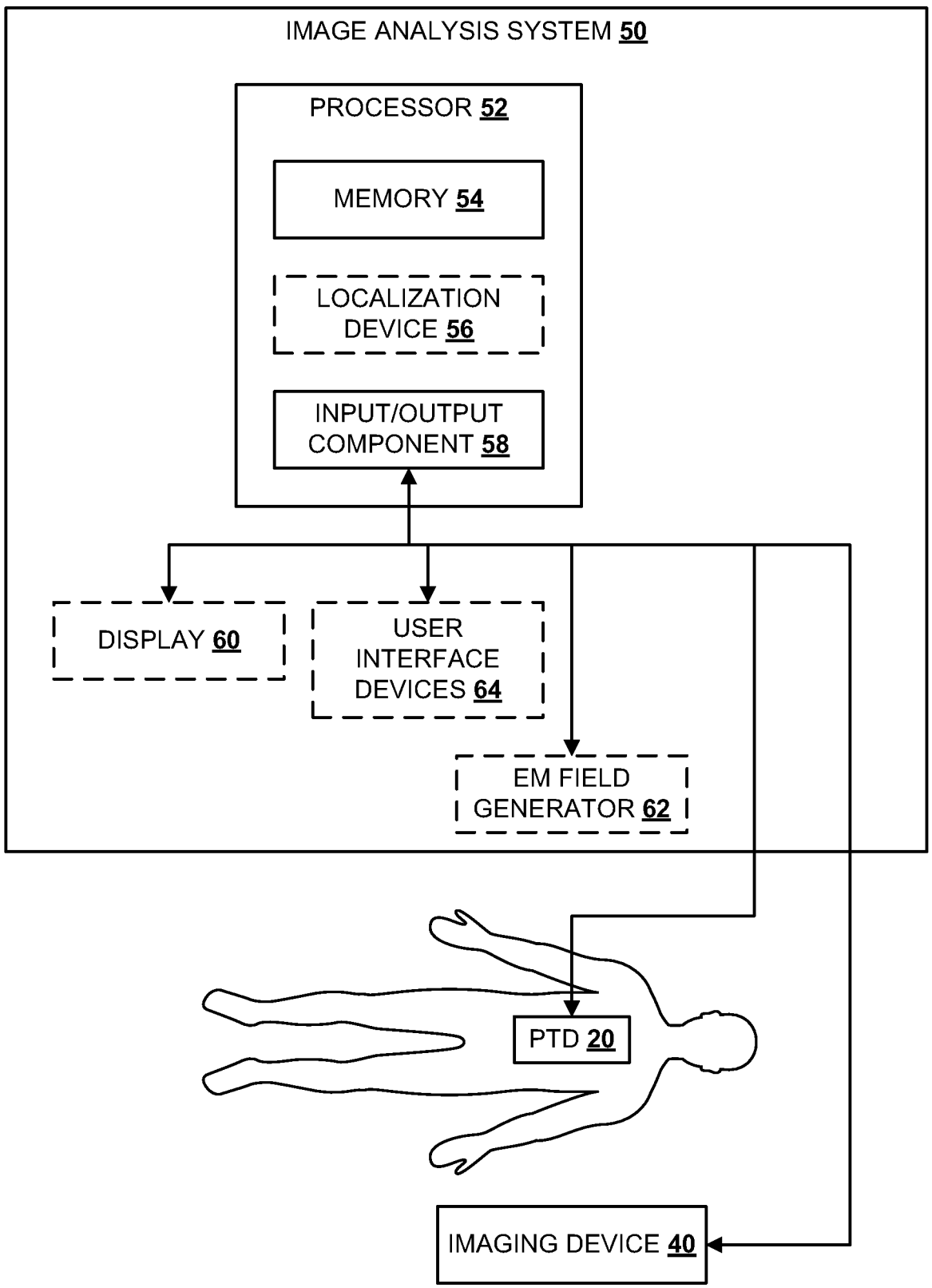
FIG. 2 is a schematic illustration of an image analysis system according to an embodiment of the invention.
Figure 3:
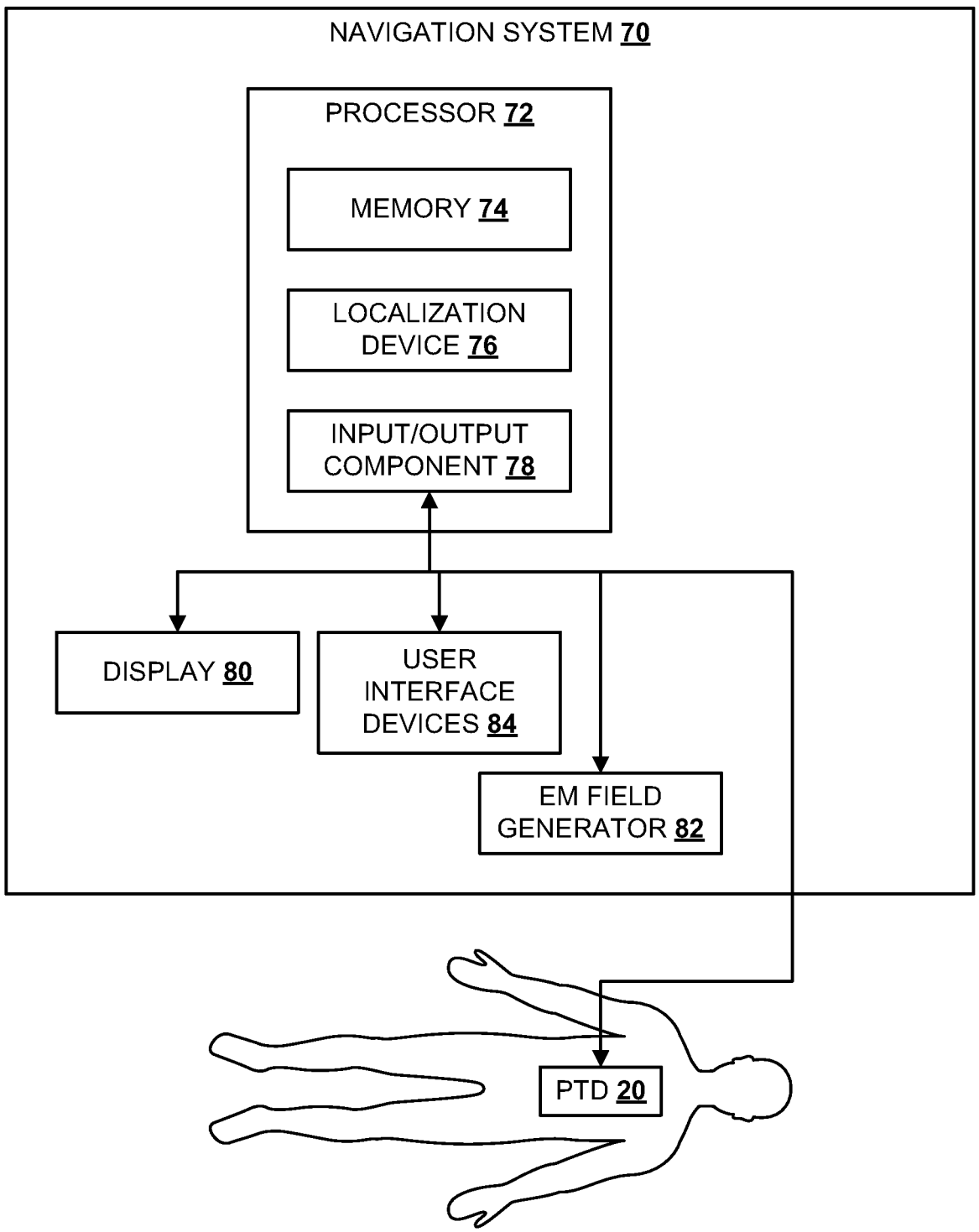
FIG. 3 is a schematic illustration of a navigation system according to an embodiment of the invention.

Referring now to FIGS. 2 and 3, two systems which may be used during image guided surgery are described in detail. The first system illustrated in FIG. 2, is image analysis system 50. Image analysis system 50 is used during generation of a population of images of patient 10 during a first time interval, prior to a medical procedure being performed on patient 10. The second system, illustrated in FIG. 3, is navigation system 70. Navigation system 70 is used during a medical procedure performed on patient 10 during a second time interval. As will be described, imaging system 50 and navigation system 70 may include, in various embodiments, substantially similar or identical components. Accordingly, image analysis system 50 and navigation system 70 may be able to carry out substantially similar or identical functions. In certain embodiments, image analysis system 50 and navigation system 70 and may comprise a single system. In certain embodiments, for example, image analysis system 50 may also function or serve as a navigation system. In certain embodiments, for example, navigation system 70 may also function or serve as an image analysis system.

As shown in FIG. 2, image analysis system 50 comprises a processor 52 having memory component 54, input/output (I/O) component 58, and optional localization device 56. Image analysis system 50 may also optionally include display 60, electromagnetic field generator 62, and/or user interface device(s) 64 (e.g., keyboard, mouse).

Image analysis system 50 further includes and/or is in data communication with imaging device 40. Imaging device 40 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, a 2D or 3D fluoroscopic imaging device, and 2D, 3D or 4D ultrasound imaging devices, or any other suitable medical imaging device. In one embodiment, for example, imaging device 40 is a computed tomography—positron emission tomography (CT/PET) device that produces a fused computed tomography—positron emission tomography (CT/PET) image dataset. In the case of a two-dimensional imaging device, a population of two-dimensional images may be acquired and then assembled into volumetric data (e.g., three-dimensional (3D) image dataset) as is well known in the art using a two-dimensional to three-dimensional conversion. Pre-procedurally during a first time interval, imaging device 40 can be used to generate a population of images of patient 10 while PTD 20 is coupled to patient 10; wherein the population of images depict the anatomy of patient 10. The anatomy, may include, but is not limited to, the lungs, heart, liver, kidneys, and/or other organs of patient 10. The population of images can be compiled into an image dataset. As stated above, some or all markers 22 of PTD 20 are visible on the population of images and provide an indication of a position of some or all of markers 22 during the first time interval. The position of markers 22 at given instants in time through a path of motion of patient 10 can be illustrated with the images.

Processor 52 of image analysis system 50 includes a processor-readable medium storing code representing instructions to cause the processor 52 to perform a process. Processor 52 can be, for example, a commercially available personal computer, or a less complex computing or processing device that is dedicated to performing one or more specific tasks. For example, processor 52 can be a terminal dedicated to providing an interactive graphical user interface (GUI) on optional display 60. Processor 52, according to one or more embodiments of the invention, can be a commercially available microprocessor. Alternatively, processor 52 can be an application-specific integrated circuit (ASIC) or a combination of ASICs, which are designed to achieve one or more specific functions, or enable one or more specific devices or applications. In yet another embodiment, processor 52 can be an analog or digital circuit, or a combination of multiple circuits.

Additionally, processor 52 can include memory component 54. Memory component 54 can include one or more types of memory. For example, memory component 54 can include a read only memory (ROM) component and a random access memory (RAM) component. Memory component 54 can also include other types of memory that are suitable for storing data in a form retrievable by processor 52. For example, electronically programmable read only memory (EPROM), erasable electronically programmable read only memory (EEPROM), flash memory, as well as other suitable forms of memory can be included within the memory component. Processor 52 can also include a variety of other components, such as for example, coprocessors, graphic processors, etc., depending upon the desired functionality of the code.

Processor 52 can store data in memory component 54 or retrieve data previously stored in memory component 54. The components of processor 52 can communicate with devices external to processor 52 by way of input/output (I/O) component 58. According to one or more embodiments of the invention, I/O component 58 includes a variety of suitable communication interfaces. For example, I/O component 58 can include, for example, wired connections, such as standard serial ports, parallel ports, universal serial bus (USB) ports, S-video ports, local area network (LAN) ports, small computer system interface (SCSI) ports, and so forth. Additionally, I/O component 58 can include, for example, wireless connections, such as infrared ports, optical ports, Bluetooth® wireless ports, wireless LAN ports, or the like. Embodiments of image analysis system 50 which include display 60, electromagnetic field generator 62, and/or user interface device(s) 64, such components communicate with processor 52 via I/O component 58.

Processor 52 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

As stated above, processor 52 receives the population of images from imaging device 40. Processor 52 identifies the position of selected markers 22 within the image data or voxel space using various segmentation techniques, such as Hounsfield unit thresholding, convolution, connected component, or other combinatory image processing and segmentation techniques. Processor 52 determines a distance and direction between the position of any two markers 22 during multiple instants in time during the first time interval, and stores the image data, as well as the position and distance data, within memory component 54. Multiple images can be produced providing a visual image at multiple instants in time through the path of motion of the dynamic body.

As stated above, processor 52 can optionally include a receiving device or localization device 56 for tracking the location of localization elements 24 of PTD 20, as described more fully elsewhere herein. By tracking localization elements 24 associated with PTD 20 when the population of images are generated by imaging device 40, the population of images may be gated. That is, image analysis system 50 determines the respiratory phase at which the population of images were generated and this information may be stored in an image dataset and/or in another data store in memory component 54.

In general, image analysis system 50 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, image analysis system 50 may include an electromagnetic tracking system, typically comprising an electromagnetic (EM) field generator 62 that emits a series of electromagnetic fields designed to engulf patient 10, and localization elements 24 coupled to PTD 20. In certain embodiments, for example, localization elements 24 are electromagnetic coils that receive an induced voltage from electromagnetic (EM) field generator 62, wherein the induced voltage is monitored and translated by localization device 56 into a coordinate position of localization elements 24. In certain embodiments, localization elements 24 are electrically coupled to twisted pair conductors to provide electromagnetic shielding of the conductors. This shielding prevents voltage induction along the conductors when exposed to the magnetic flux produced by the electromagnetic field generator.

Accordingly, localization device 56 can be, for example, an analog to digital converter that measures voltages induced onto localization elements 24 in the field generated by EM field generator 62; creates a digital voltage reading; and maps that voltage reading to a metric positional measurement based on a characterized volume of voltages to millimeters from electromagnetic field generator 62. Position data associated with localization elements 24 can be transmitted or sent to localization device 56 continuously during imaging of patient 10 during the first time interval. Thus, the position of localization elements 24 can be captured at given instants in time during the first time interval. Because localization elements 24 are proximate markers 22, localization device 56 uses the position data of localization elements 24 to deduce coordinates or positions associated with markers 22 during the first time interval. The distance, range, acceleration, and speed between one or more selected pairs of localization elements 24 (and corresponding markers 22) is then determined and various algorithms are used to analyze and compare the distance between selected elements 24 at given instants in time, to the distances between and orientation among corresponding markers 22 observed in a population of pre-procedural images.

As shown in FIG. 3, navigation system 70 comprises a processor 72 having memory component 74, input/output (I/O) component 78, and localization device 76. Navigation system 70 also includes display 80, electromagnetic field generator 82, and/or user interface device(s) 84 (e.g., keyboard, mouse). In certain embodiments, navigation system 50 further includes and/or is in data communication with imaging device 40 (see FIG. 2).

Processor 72 of navigation system 70 includes a processor-readable medium storing code representing instructions to cause the processor 72 to perform a process. Processor 72 can be, for example, a commercially available personal computer, or a less complex computing or processing device that is dedicated to performing one or more specific tasks. For example, processor 72 can be a terminal dedicated to providing an interactive graphical user interface (GUI) on optional display 80. Processor 72, according to one or more embodiments of the invention, can be a commercially available microprocessor. Alternatively, processor 72 can be an application-specific integrated circuit (ASIC) or a combination of ASICs, which are designed to achieve one or more specific functions, or enable one or more specific devices or applications. In yet another embodiment, processor 72 can be an analog or digital circuit, or a combination of multiple circuits.

Additionally, processor 72 can include memory component 74. Memory component 74 can include one or more types of memory. For example, memory component 74 can include a read only memory (ROM) component and a random access memory (RAM) component. Memory component 74 can also include other types of memory that are suitable for storing data in a form retrievable by processor 72. For example, electronically programmable read only memory (EPROM), erasable electronically programmable read only memory (EEPROM), flash memory, as well as other suitable forms of memory can be included within the memory component. Processor 72 can also include a variety of other components, such as for example, coprocessors, graphic processors, etc., depending upon the desired functionality of the code.

Processor 72 can store data in memory component 74 or retrieve data previously stored in memory component 74. The components of processor 72 can communicate with devices external to processor 72 by way of input/output (I/O) component 78. According to one or more embodiments of the invention, I/O component 78 includes a variety of suitable communication interfaces. For example, I/O component 78 can include, for example, wired connections, such as standard serial ports, parallel ports, universal serial bus (USB) ports, S-video ports, local area network (LAN) ports, small computer system interface (SCSI) ports, and so forth. Additionally, I/O component 78 can include, for example, wireless connections, such as infrared ports, optical ports, Bluetooth® wireless ports, wireless LAN ports, or the like. Additionally, display 80, electromagnetic field generator 82, and/or user interface device(s) 84, communicate with processor 72 via I/O component 78.

Processor 72 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

In general, navigation system 70 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, navigation system 70 may include an electromagnetic tracking system, typically comprising an electromagnetic (EM) field generator 82 that emits a series of electromagnetic fields designed to engulf patient 10, and localization elements 24 coupled to PTD 20. In certain embodiments, for example, localization elements 24 are electromagnetic coils that receive an induced voltage from electromagnetic (EM) field generator 82, wherein the induced voltage is monitored and translated by localization device 76 into a coordinate position of localization elements 24. In certain embodiments, localization elements 24 are electrically coupled to twisted pair conductors to provide electromagnetic shielding of the conductors. This shielding prevents voltage induction along the conductors when exposed to the magnetic flux produced by the electromagnetic field generator.

Accordingly, localization device 76 may be, for example, an analog to digital converter that measures voltages induced onto localization elements 24 in the field generated by EM field generator 82; creates a digital voltage reading; and maps that voltage reading to a metric positional measurement based on a characterized volume of voltages to millimeters from electromagnetic field generator 82. Position data associated with localization elements 24 may be transmitted or sent to localization device 76 continuously during the medical procedure performed during the second time interval. Thus, the position of localization elements 24 may be captured at given instants in time during the second time interval. Because localization elements 24 are proximate markers 22, localization device 76 uses the position data of localization elements 24 to deduce coordinates or positions associated with markers 22 during the second time interval. The distance, range, acceleration, and speed between one or more selected pairs of localization elements 24 (and corresponding markers 22) is then determined and various algorithms are used to analyze and compare the distance between selected elements 24 at given instants in time, to the distances between and orientation among corresponding markers 22 observed in a population of pre-procedural images.

Because localization elements 24 of PTD 20 may be tracked continuously during the first and/or second time intervals, a sequence of motion of PTD 20 that represents the motion of an organ of patient 10 or the patient's 10 respiratory cycle may be collected. As patient 10 inhales and exhales, the individual localization elements 24 of PTD 20 will move relative to one another. That is, as patient 10 inhales, the distance between some or all of localization elements 24 of PTD 20 may increase. Conversely, as patient 10 exhales, the distance between some or all of localization elements 24 of PTD 20 may decrease. The sequence of motion of localization elements 24 is tracked by image analysis system 50 and/or navigation system 70 and image analysis system 50 and/or navigation system 70 derives a respiratory signal based on the positions of localization elements 24 during the respiratory cycle of patient 10. The sequence of motion may then be analyzed to find unique similar points within the image dataset and images within the image dataset may be grouped.

According to one particular embodiment, the respiratory signal derived from PTD 20 is used to gate the localization information of a medical device in the airway of patient 10. In other embodiments, the respiratory signal derived from PTD 20 is used during the first time interval to gate the population of images generated by imaging device 40. Using PTD 20 to derive a respiratory signal may assist in determining multiple airway models, for example, by performing a best fit of the real-time patient airway model to the image dataset to derive the optimal registration and gated period in the patient's respiratory cycle. Additionally or alternatively, the respiratory signal may be derived from devices other than PTD 20 that are known in the art for measuring the respiratory cycle of a patient. In certain embodiments, for example, a device that records the resistance between two locations on the patient may be used to measure the respiratory cycle. For example, such device a is similar to a variable potentiometer in that the resistance of the patient changes between two fixed points as the patient inhales and exhales. Thus, the resistance may be measured to create a respiratory signal. In other embodiments, a spirometer may be used to measure the respiratory cycle. In yet other embodiments, a cardiac signal may be used to gate the localization information of a medical device in the airway of patient 10. It will be understood that any type of device for generating a cardiac signal may be used, including, but not limited to an ECG device, PTD 20, etc.

Figure 4:
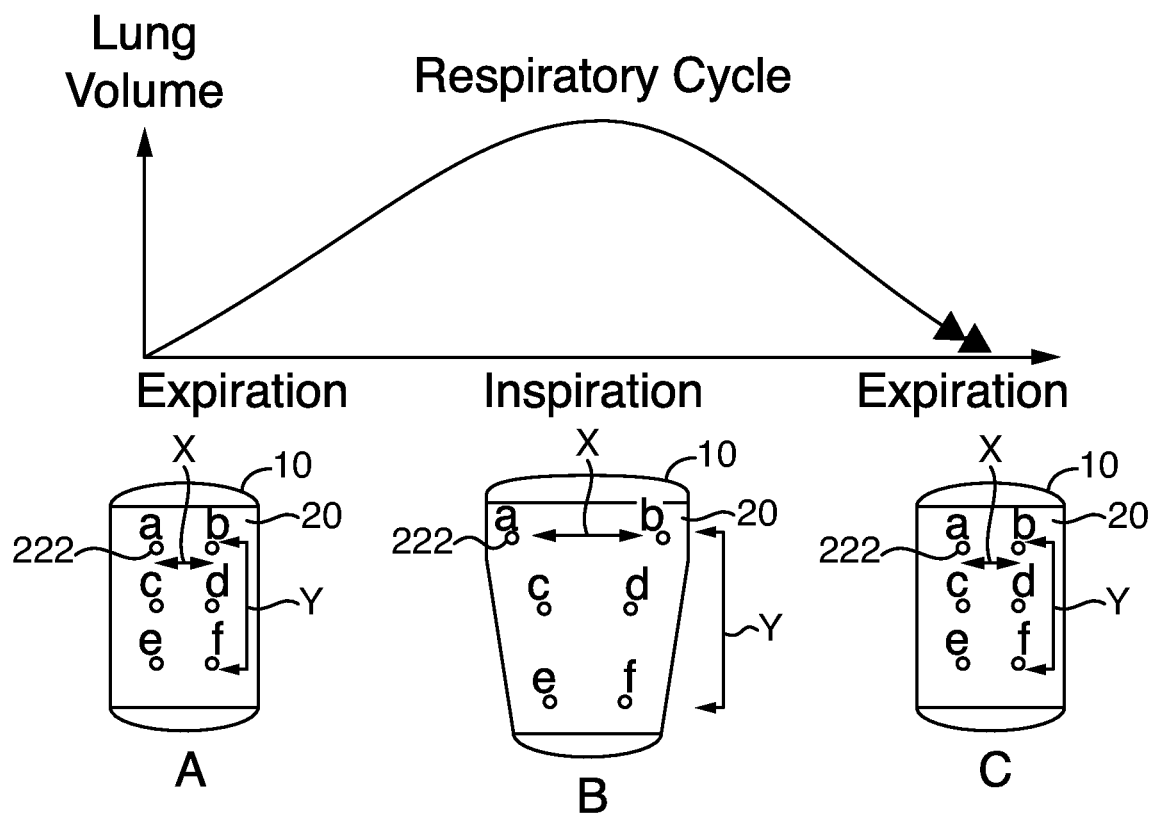
FIG. 4 is a graphical representation illustrating the function of the patient tracking device according to an embodiment of the invention.

FIG. 4 is a schematic illustration indicating how markers 22 of PTD 20 can move and change orientation and shape during movement of patient 10. The graph is one example of how the lung volume can change during inhalation (inspiration) and exhalation (expiration) of patient 10. The corresponding changes in shape and orientation of PTD 20 during inhalation and exhalation are also illustrated. The six markers 22 shown in FIG. 1 are schematically represented and labeled a, b, c, d, e, and f. As described above, a population of images of PTD 20 may be taken during a first time interval. The population of images include an indication of relative position of one or more markers 22; that is, one or more markers 22 are visible in the images, and the position of each marker 22 is then observed over a period of time. A distance between any two markers 22 may then be determined for any given instant of time during the first time interval. For example, a distance X between markers a and b is illustrated, and a distance Y between markers b and f is illustrated. These distances may be determined for any given instant in time during the first time interval from an associated image that illustrates the position and orientation of markers 22. As illustrated, during expiration of patient 10 at times indicated as A and C, the distance X is smaller than during inspiration of patient 10, at the time indicated as B. Likewise, the distance Y is greater during inspiration than during expiration. The distance between any pair of markers 22 may be determined and used in the processes described herein. Thus, the above embodiments are merely examples of possible pair selections. For example, a distance between a position of marker e and a position of marker b may be determined. In addition, multiple pairs or only one pair may be selected for a given procedure.

Figure 5A:
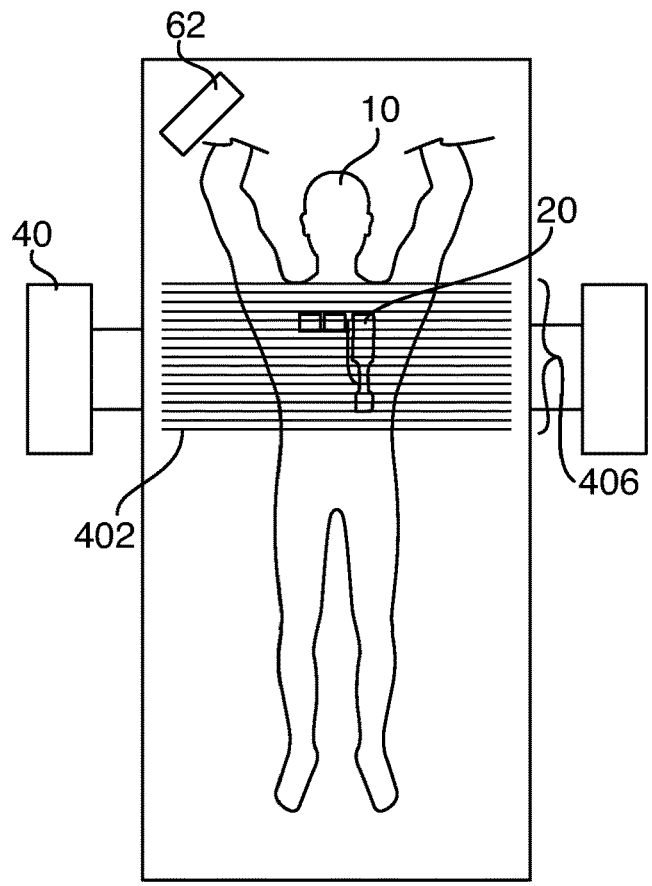
FIG. 5A is an illustration of a patient being imaged using an imaging device according to an embodiment of the invention.
Figure 5B:
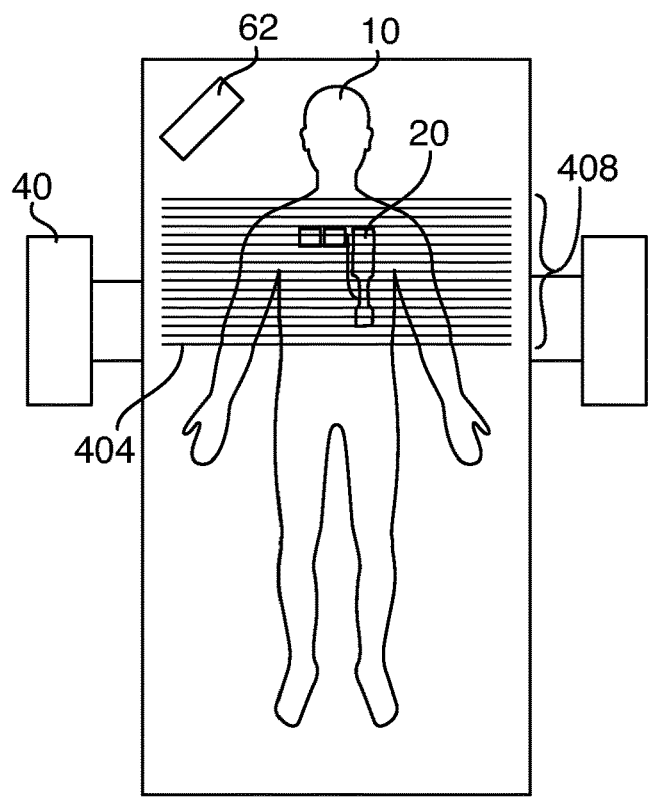
FIG. 5B is an illustration of a patient being imaged using an imaging device according to an embodiment of the invention.

FIGS. 5A and 5B illustrate the generation of a population of images during a first time interval using imaging device 40, PTD 20, and optionally electromagnetic field generator 62 of image analysis system 50. In FIG. 5A, patient 10 inhales and patient 10 is scanned using imaging device 40 which generates a population of images 402 of the anatomy of patient 10 and markers 22 at inspiration. As shown, patient 10 may place their arms above their head as they inhale, and this may be considered a total lung capacity (TLC) scan. In FIG. 5B, patient 10 exhales and patient 10 is scanned using imaging device 40 which generates a population of images 404 of the anatomy of patient 10 and markers 22 at expiration. As shown, patient 10 may place their arms below their head, and this may be considered a functional residual capacity (FRC) scan. The Functional Residual Capacity is the lung volume at the end of a normal expiration, when the muscles of respiration are completely relaxed. At FRC (and typically at FRC only), the tendency of the lungs to collapse is exactly balanced by the tendency of the chest wall to expand. In various embodiments, the population of images 402, 404 may be two-dimensional (2D) images. In other embodiments, for example, the population of images 402, 404 may be three-dimensional (3D) images. Additionally, the population of images 402, 404 may be respiratory gated by tracking the location of localization elements 24 of PTD 20 by image analysis system 50 and/or navigation system 70 using EM field generator 62, 82 during image generation. In other embodiments, for example, the population of images 402, 404 may be gated using any type of device known for generating a physiological signal for gating.

In various embodiments, for example, instead of patient 10 holding an inspiration or expiration state, a cine loop of images may be generated in conjunction with the patient's respiratory cycle information from PTD 20. Thus the cine loop comprises a population of images generated from inspiration to expiration where the population of images are gated to the respiratory cycle of patient 10 using PTD 20. This can serve to limit registration point selection, in order to be consistent with the patient's respiratory cycle that a 3D dataset such as CT, MR, or PET has acquired. This technique advantageously maximizes registration accuracy, a major flaw in conventional systems in the prior art.

Figure 5C:
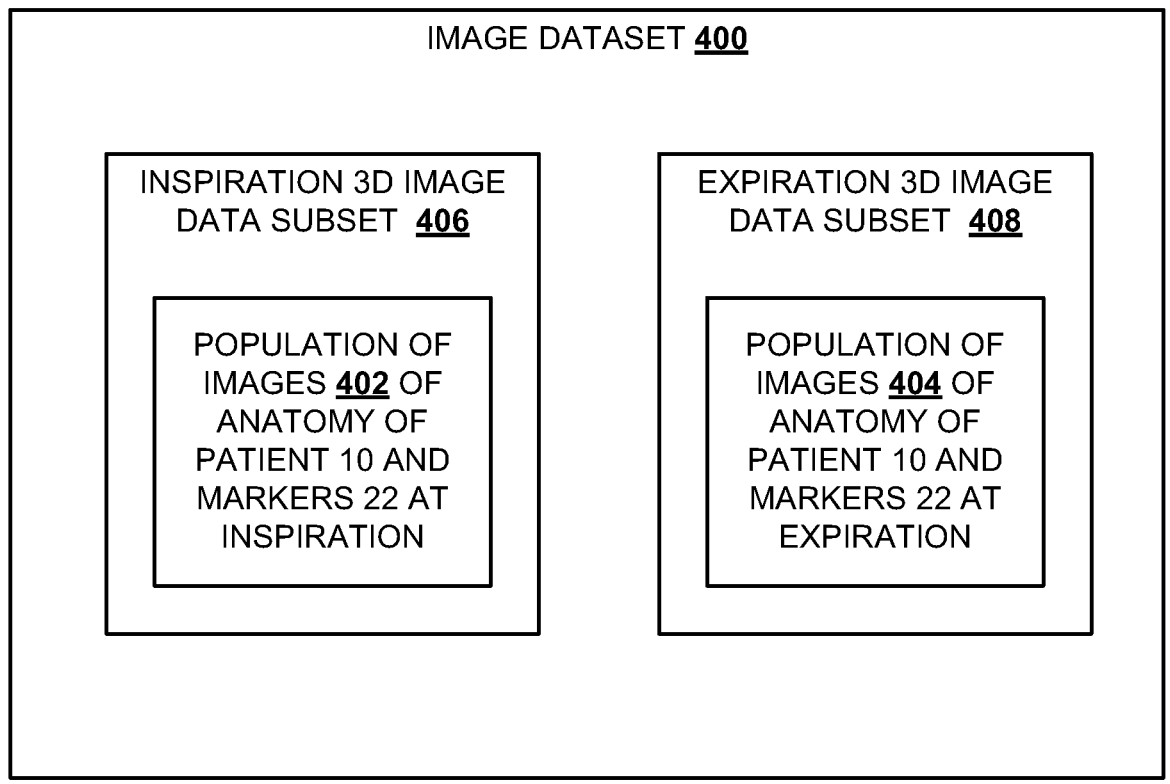
FIG. 5C is a schematic illustration of an image dataset according to an embodiment of the invention.

As described above, imaging device 40 is in data communication with image analysis system 50 and/or navigation system 70 and sends, transfers, copies and/or provides the population of images 402, 404 taken during the first time interval associated with patient 10 to image analysis system 50 and/or navigation system 70. As shown in FIG. 5C, image analysis system 50 and/or navigation system 70 compiles the population of images 402 at inspiration into a 3D image data subset 406 of the anatomy of patient 10 and markers 22 at inspiration (referred to herein as inspiration 3D image data subset 406). Additionally, image analysis system 50 and/or navigation system 70 compiles the population of images 404 at expiration into a 3D image data subset 408 of the anatomy of patient 10 at expiration (referred to herein as expiration 3D image data subset 408). The inspiration 3D image data subset 406 and the expiration 3D image data subset 408 are then stored in an image dataset 400 in memory component 54, 74 of image analysis system 50 and/or navigation system 70.

Figure 6A:
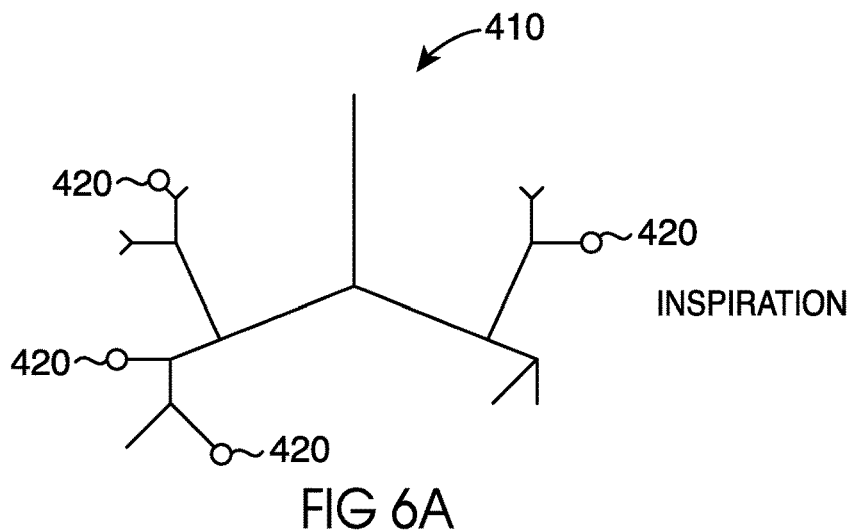
FIG. 6A is a schematic illustration of an inspiration 3D airway model according to an embodiment of the invention.
Figure 6B:
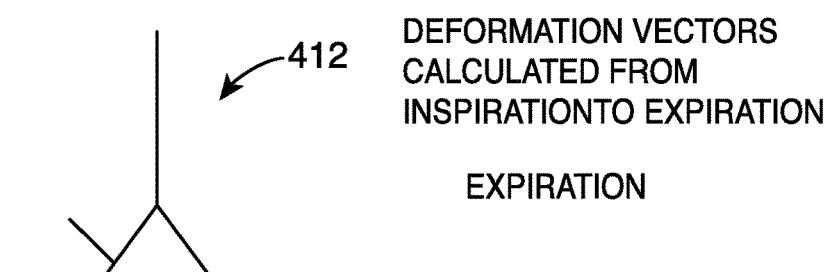
FIG. 6B is a schematic illustration of an expiration 3D airway model according to an embodiment of the invention.
Figure 6C:
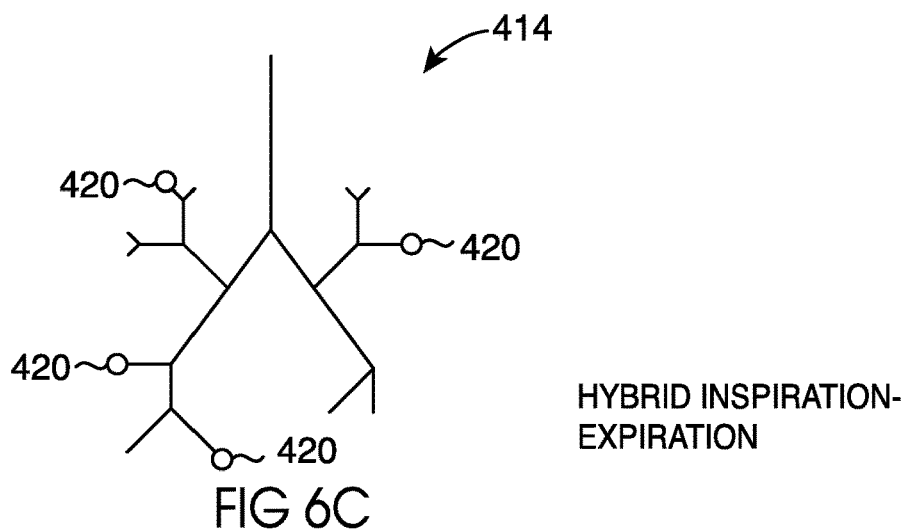
FIG. 6C is a schematic illustration of a hybrid "Inspiration-Expiration" 3D airway model according to an embodiment of the invention.

Additionally, acquiring a population of images at both inspiration and expiration may assist navigation of a steerable catheter during a second time interval. Referring now to FIGS. 6A-6C, in addition to segmenting the markers 22 of PTD 20 from the population of images 402, 404 generated during the first time interval, processor 52 of image analysis workstation 50 generates three-dimensional models of the airway of patient 10 by segmenting the 3D image data subsets 406, 408. In various embodiments, segmentation of the airway may be accomplished using an iterative region growing technique wherein a seed voxel in the airway is selected as an initialization parameter. Voxels neighboring the seed voxel are then evaluated to determine whether they are a part of the airway, form the wall surrounding the airway, or form other tissue. Following segmentation, a surface mesh of the airway may be generated to produce a surface skeleton. The surface of the airway may then be rendered.

As shown in FIG. 6A, a three-dimensional model of the airway of patient 10 at inspiration ("inspiration 3D airway model 410") is generated by segmenting the inspiration 3D image data subset 406. FIG. 6A shows an Inspiration/arms-up pathway registration; this is, generally speaking, the preferred image scan acquisition state for automatic segmentation of the tracheo-bronchial tree. Processor 52 may also segment one or more target tissues 420 (e.g., lesions, lymph nodes, blood vessels, tumors, etc.) which may be navigated to during a second time interval using a variety of medical devices as described more fully elsewhere herein. The segmentation of the target tissue(s) 420 may be refined to define different characteristics of the target tissue, such as, for example, density of the target tissue. Additional image data formats may also be loaded into processor 52, such as, for example, PET or MR and processor 52 may be able to map the CT, PET, and/or MR data to one another.

As shown at FIG. 6B, a three-dimensional model of the airway of patient 10 at expiration ("expiration 3D airway model 412") is generated by segmenting the expiration 3D image data subset 408. As discussed above, a variety of segmentation algorithms known in the art may be used to generate the inspiration and expiration 3D airway models 410, 412. FIG. 6B shows, in contrast to FIG. 6A, an FRC/arms-down segmentation. Because the patient's 10 lungs are more full of air at inspiration than at expiration, the inspiration 3D airway model 410 includes more structure than the expiration 3D airway model 412. Accordingly, as shown in FIG. 6B, expiration 3D airway model 412 includes fewer structure(s) and the structure(s) are in different locations and/or orientations than at inspiration. However during a procedure such as directing a navigated steerable catheter to a target tissue within the airway of patient 10 (e.g., during a second time interval), the breathing cycle of patient 10 may be closer to tidal breathing. That is, patient 10 usually never reaches full inspiration during the procedure and thus if the segmentation of the airways of patient 10 at inspiration is used for navigation purposes, there will be significant error in the registration of the segmented airway to patient 10.

In certain embodiments, a hybrid "Inspiration-Expiration" 3D airway model 414 is constructed as shown in FIG. 6C using the inspiration 3D airway model 410 and the expiration 3D airway model 412. The hybrid "Inspiration-Expiration" 3D airway model 414 may be used to reduce or eliminate the errors in registration. To construct the hybrid "Inspiration-Expiration" 3D airway model 414, a population of deformation vector fields is calculated by processor 52, 72 of image analysis system 50 and/or navigation system 70. The deformation vector field comprises vectors from one or more voxels in the inspiration 3D airway model 410 to one or more corresponding voxels in the expiration 3D airway model 412. After the deformation vector field is calculated, the inspiration 3D airway model 410 is deformed to the expiration state of patient 10 using the deformation vector field. Accordingly, the voxels in the inspiration 3D airway model 410 are deformed to match the location, shape, and orientation of the airways of patient 10 at expiration. This results in the hybrid "Inspiration-Expiration" 3D airway model 414, wherein the hybrid "Inspiration-Expiration" 3D airway model 414 contains all of the structural information of the airways of patient 10 depicted in inspiration 3D airway model 410. However, this structural information is now more closely matched to the location, shape, and orientation of the airways of patient 10 depicted in expiration 3D airway model 412. Accordingly, the deformation vectors represent not only a change in location of the structure of the airway but a change in shape of the structure of the airway from inspiration to expiration.

Figure 7:
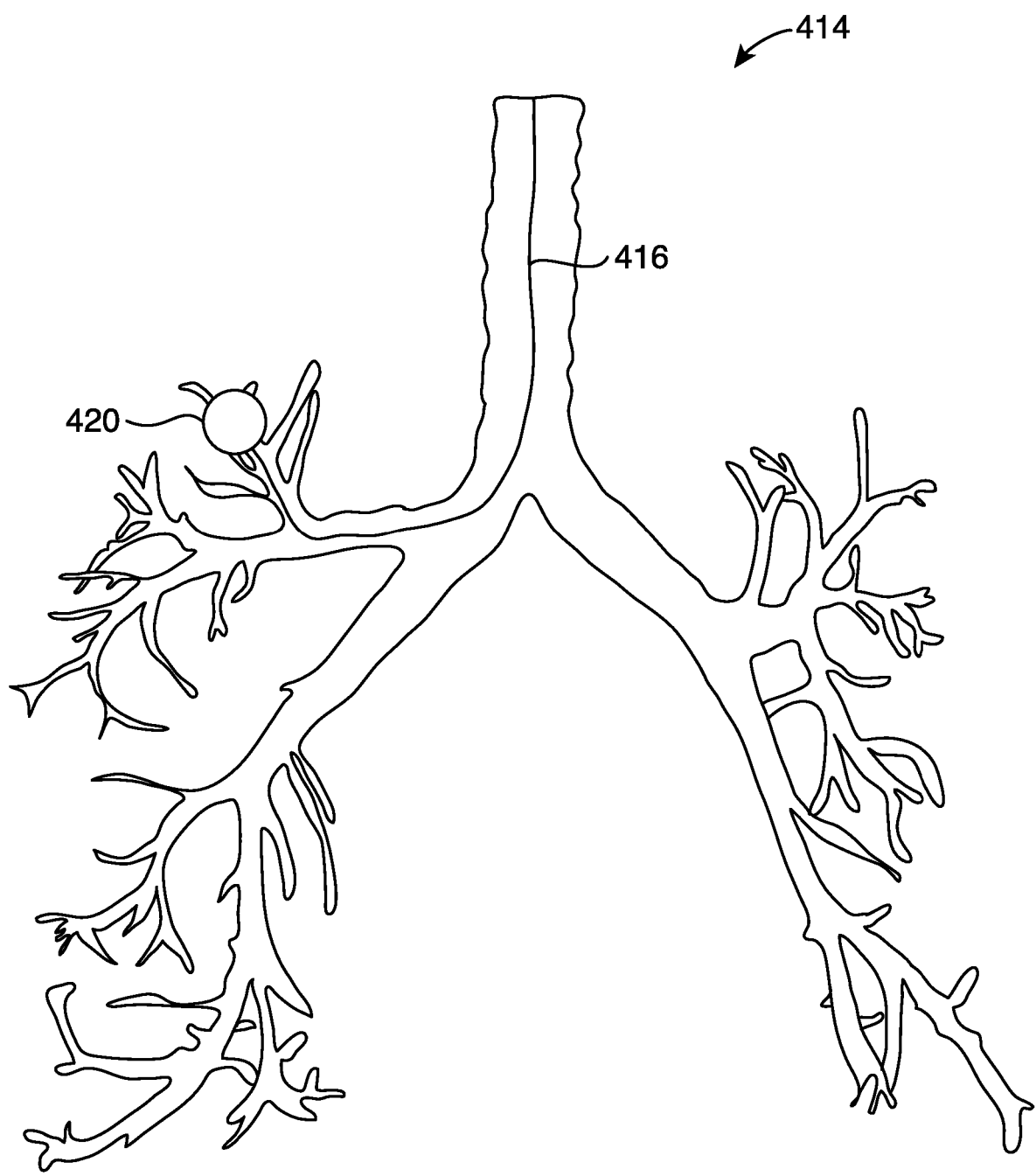
FIG. 7 is a front perspective view of a hybrid "Inspiration-Expiration" 3D airway model according to an embodiment of the invention.

FIG. 7, illustrates a 3D representation of hybrid "Inspiration-Expiration" 3D airway model 414 which includes a target tissue 420 segmented by processor 52, 72. This 3D representation of hybrid "Inspiration-Expiration" 3D airway model 414 may include surface information. Hybrid "Inspiration-Expiration" 3D airway model 414 may additionally include navigation pathway 416. Image analysis system 50 and/or navigation system 70 may calculate navigation pathway 416 from the entry of the airway to the location of target tissue 420. In certain embodiments, navigation pathway 416 may be an optimal endobronchial path to a target tissue. For example, navigation pathway 416 may represent the closest distance and/or closest angle to the target tissue. A physician or other healthcare professional may follow navigation pathway 416 during an image guided intervention to reach the location of target tissue 420.

Although target tissue 420 locations and navigation pathway(s) 416 may be automatically calculated by image analysis system 50 and/or navigation system 70, a physician or other healthcare professional may manually adjust target tissue 420 locations and/or navigation pathway(s) 416.

In general, the embodiments described herein have applicability in "Inspiration to Expiration"-type CT scan fusion. According to various methods, the user navigates on the expiration 3D image data subset 408 for optimal accuracy, while using the inspiration 3D image data subset 406 to obtain maximum airway segmentation. In one embodiment, for example, a user could complete planning and pathway segmentation on the inspiration 3D image data subset 406 of patient 10. Preferably, a deformation vector field is created between at least two datasets (e.g., from inspiration 3D image data subset 406 to expiration 3D image data subset 408). The deformation or vector field may then be applied to the segmented vessels and/or airways and navigation pathway 416 and target tissue 420 locations. In these and other embodiments, the deformation or vector field may also be applied to multiple image datasets or in a progressive way to create a moving underlying image dataset that matches the respiratory or cardiac motion of patient 10.

By way of example, in certain embodiments, "Inspiration to Expiration" CT fusion using the lung lobe centroid and vector change to modify an airway model may also be applicable. In accordance with various embodiments, this technique is used to translate and scale each airway based on the lung lobe change between inspiration images and expiration images. The lung is constructed of multiple lobes and these lobes are commonly analyzed for volume, shape, and translation change. Each lobe changes in a very different way during the patient's breathing cycle. Using this information to scale and translate the airways that are located in each lobe, it is possible to adapt for airway movement. This scaled airway model may then be linked to the 4D tracking of the patient as described herein.

In various aspects, the systems and methods described herein involve modifying inspiration images generated by imaging device 40 (e.g., CT, CT/PET, MRI, etc.) to the expiration cycle for navigation. It is well understood that the patient's airways are contained within multiple lobes of the lung. It is also understood that airways significantly change between inspiration and expiration. In certain embodiments, to increase the accuracy of the map for navigation, it may be beneficial to include the detail of the inspiration images, coupled with the ability to navigate it accurately during expiration. For many patients, the expiration state may be the most repeatable point in a patient's breath cycle. In preferred embodiments, this modification may be carried out in accordance with the following steps:

1) Generate a population of images of patient 10 at both inspiration and expiration using imaging device 40;

2) Segment the airways in both the inspiration and expiration images;

3) Segment the lung lobes in both the inspiration and expiration images (as the lung lobes are identifiable in both the inspiration and expiration images with a high degree of accuracy);

4) Determine a volume difference for each lung lobe between inspiration and expiration, use this change to shrink the airway size from the inspiration to the expiration cycle. Preferably, this is done for each individual lobe, as the percentage change will typically be different for each lobe.

5) Determine the centroid for each lung lobe and the vector change in motion from the main carina in both inspiration images and expiration images. This vector may then be used to shift the airways that are associated with each lung lobe. A centroid for the airway may be calculated based on the segmented branches. For each airway branch in the segmentation, it includes a tag that associates it with the respective lung lobe. The central airway including the main carina and initial airway branches for each lobe that is linked according to the expiration scan location of these points. Next, a plane may be defined using the main carina and initial airway branch exits to determine the vector change for each lobe.

Among the lobes to modify, for example:

left inferior lobe—the bottom lobe of the lung on the left side of patient 10;

left superior lobe—the top lobe of the lung on the left side of patient 10.

right inferior lobe—the bottom lobe of the lung on the right side of patient 10;

right middle lobe—the middle lobe of the lung on the right side of patient 10;

right superior lobe—the top lobe of the lung on the right side of patient 10.

Exemplary calculations are as follows:

Inspiration Airway—Left Inferior Lobe (LIL)×70% (reduction in volume Inspiration to Expiration calculated)=ExAirwayLIL;

Determine Expiration Central Airway points (Main Carina and Initial Airway branches) based upon segmentation;

Shift ExAirwayLIL by vector distance (3 cm, 45 degrees up and back from main carina) that LIL centroid moved from inspiration to expiration.

Preferably, this process is repeated for each lobe. In certain embodiments, the completion of 5 lobes will result in a hybrid "Inspiration-Expiration" 3D airway model for patient 10.

In various embodiments, the target location for the patient may be selected in the expiration images and applied to the hybrid "Inspiration-Expiration" 3D airway model 414. Alternatively, it may be selected in the inspiration images and adjusted based on the same or similar criteria as the inspiration airways. In either case, it may be adjusted individually or linked to the airway via a 3D network and moved in the same transformation.

A deformation field may also be included in the analysis in various other embodiments described herein. For example, the deformation field may be applied to fuse 3D fluoroscopic images to CT images to compensate for different patient orientations, patient position, respiration, deformation induced by the catheter or other instrument, and/or other changes or perturbations that occur due to therapy delivery or resection or ablation of tissue.

Following the generation of hybrid "Inspiration-Expiration" 3D airway model 414, during a second time interval, a medical procedure is then performed on patient 10 with PTD 20 coupled to patient 10 at the same location as during the first time interval when the population of pre-procedural images were taken. Preferably, the second time interval immediately follows the first time interval. However, in certain embodiments, second time interval may occur several hours, days, weeks or months after the first time interval. After hybrid "Inspiration-Expiration" 3D airway model 414 is generated and one or more target tissues 420 are identified and one or more navigation pathways 416 are calculated, this information is transferred from image analysis system 50 to navigation system 70. This transfer may be done according to the DICOM (Digital Imaging and Communications in Medicine) standard as known in the art. It will be understood that the transfer may be done using any method and according to any standard without departing from the scope of the invention. For example, this transfer may be accomplished between image analysis system 50 to navigation system 70 using a variety of methods, including, but not limited to, a wired connection, a wireless connection, via CD, via a USB device, etc.

It should be noted that image dataset 400 may be supplemented, replaced or fused with an additional image dataset. In one embodiment, for example, during the second time interval an additional population of images may be taken. In other embodiments, for example, after the second time interval an additional population of images may be taken. By generating one or more additional image datasets, potential changed physical parameters of patient such as patient 10 movement, anatomical changes due to resection, ablation, general anesthesia, pneumothorax, and/or other organ shift may be accounted for during the procedure. Accordingly, images from CT-Fluoro, fluoroscopic, ultrasound or 3D fluoroscopy may be imported into image analysis system 50 and/or navigation system 70.

Using the respiratory signal derived from PTD 20, navigation system 70 selects an image from the population of pre-procedural images 402, 404 taken during the first time interval that indicates a distance or is grouped in a similar sequence of motion between corresponding markers 22 at a given instant in time, that most closely approximates or matches the distance or similar sequence of motion between the selected localization elements 24. The process of comparing the distances is described in more detail below. Thus, navigation system 70 displays images corresponding to the actual movement of the targeted anatomy during the medical procedure being performed during the second time interval. The images illustrate the orientation and shape of the targeted anatomy during a path of motion of the anatomy, for example, during inhaling and exhaling.

Figure 8:
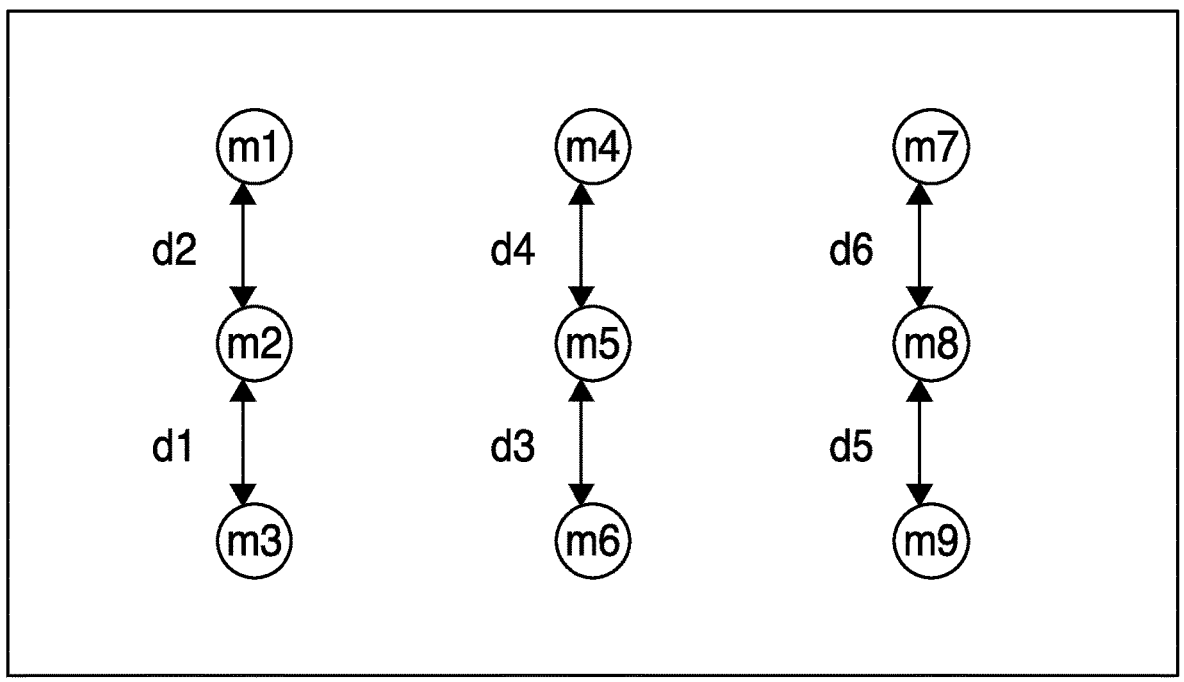
FIG. 8 is a schematic illustrating vector distances of the patient tracking device according to an embodiment of the invention.

FIG. 8 illustrates an example set of distances or vectors d1 through d6 between a set of markers 22, labeled m1 through m9 that are disposed at spaced locations on PTD 20. As described above, a population of pre-procedural images is taken of a patient 10 to which PTD 20 is coupled during a first time interval. The distances between markers 22 are determined for multiple instants in time through the path of motion of the dynamic body (e.g., the respiratory cycle of the patient). Then, during a medical procedure, performed during a second time interval, localization elements 24 (not shown in FIG. 8) proximate the location of markers 22 provide position data for localization elements 24 to localization device 76 (not shown in FIG. 8). Navigation system 70 uses the position data to determine distances or vectors between localization elements 24 for multiple instants in time during the medical procedure or second time interval.

Figure 9A:
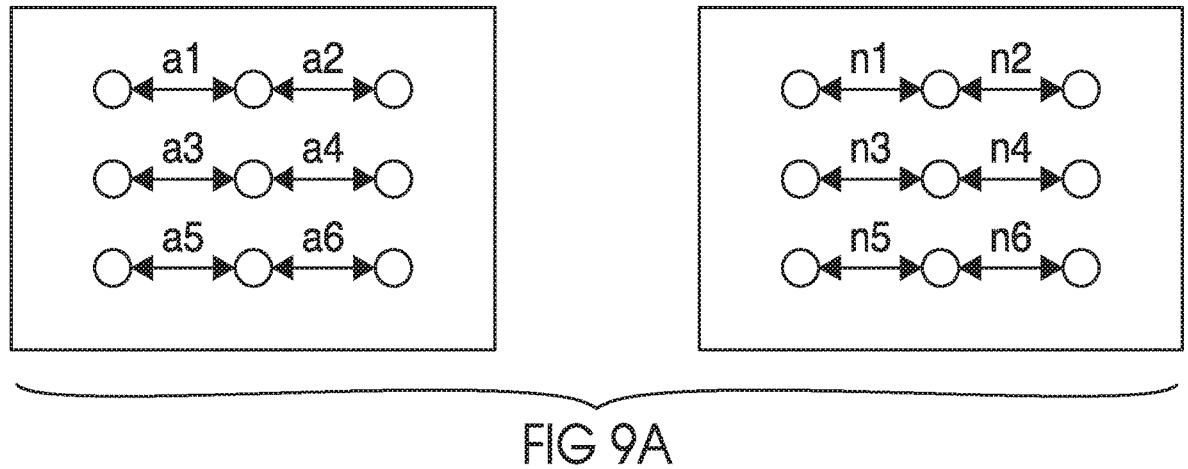
FIG. 9A is a schematic illustrating vector distances from a localization element on the patient tracking device according to an embodiment of the invention.

FIG. 9A shows an example of distance or vector data from localization device 76. Vectors a1 through a6 represent distance data for one instant in time and vectors n1 through n6 for another instant in time, during a time interval from a to n. As previously described, the vector data may be used to select an image from the population of pre-procedural images that includes distances between the markers m1 through m9 that correspond to or closely approximate the distances a1 through a6 for time a, for example, between the localization elements. The same process may be performed for the vectors n1 through n6 captured during time n.

Figure 9B:
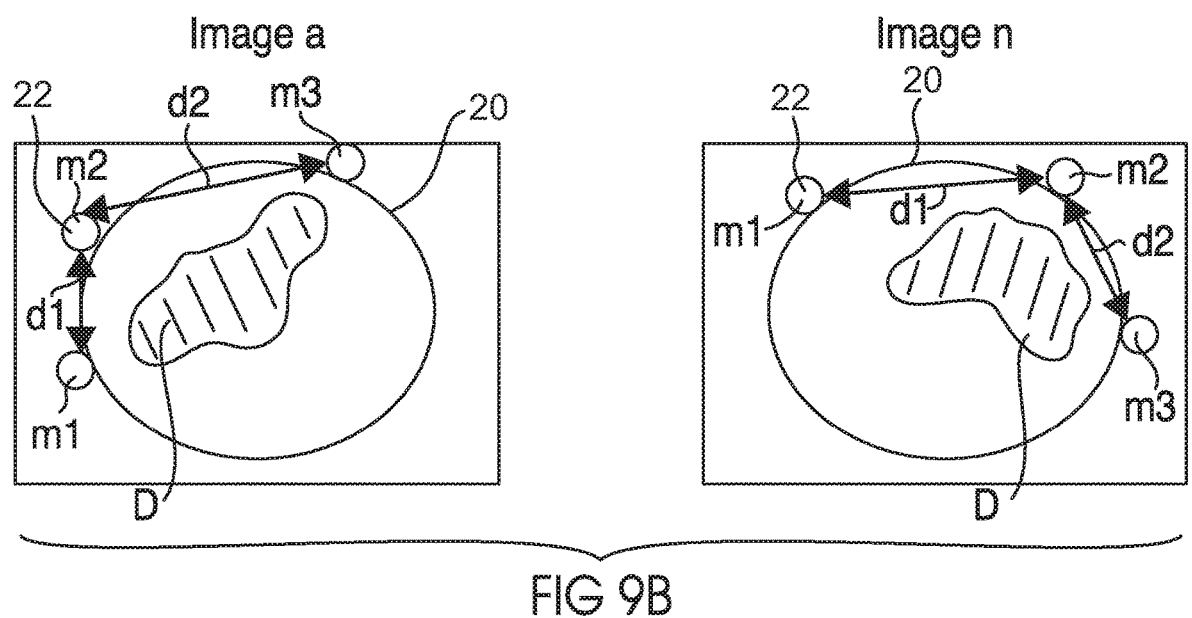
FIG. 9B is a schematic illustrating vector distances from an image dataset according to an embodiment of the invention.

One method of selecting the appropriate image from the population of pre-procedural images 402, 404 is to execute an algorithm that sums all of the distances a1 through a6 and then search for and match this sum to an image containing a sum of all of the distances d1 through d6 obtained pre-procedurally from the image data that is equal to the sum of the distances a1 through a6. When the difference between these sums is equal to zero, the relative position and orientation of the anatomy or dynamic body D during the medical procedure will substantially match the position and orientation of the anatomy in the particular image. The image associated with distances d1 through d6 that match or closely approximate the distances a1 through a6 may then be selected and displayed. For example, FIG. 9B illustrates examples of pre-procedural images, Image a and Image n, of a dynamic body D that correspond to the distances a1 through a6 and n1 through n6, respectively. An example of an algorithm for determining a match is as follows:

Does $\Sigma a_i = \Sigma d_i$ (i=1 to 6 in this example) OR
Does $\Sigma(a_i - d_i) = 0$ (i=1 to 6 in this example).

If yes to either of these, then the image is a match to the vector or distance data obtained during the medical procedure.

Figure 10:
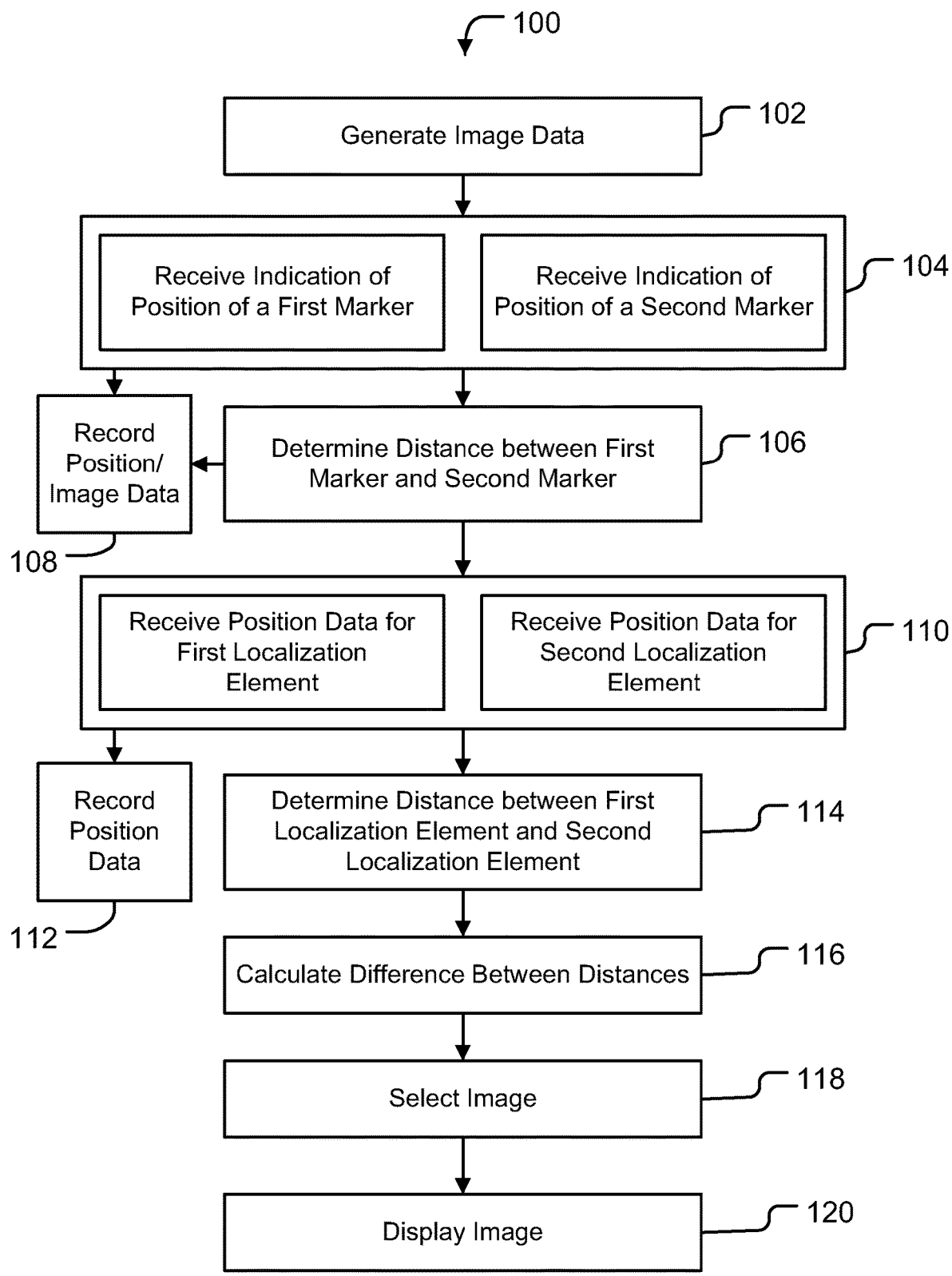
FIG. 10 is a flowchart illustrating a method according to an embodiment of the invention.

FIG. 10 is a flowchart illustrating a method according to an embodiment of the invention. A method 100 includes at step 102 generating image data during a pre-procedural or first time interval. As discussed above, a population of images are generated of a dynamic body, such as patient 10, using imaging device 40 (e.g., CT Scan, MRI, etc.). The image data is associated with one or more images generated of PTD 20 coupled to a dynamic body, where PTD 20 includes two or more markers 22. In other words, the image data of the dynamic body is correlated with image data related to PTD 20. The one or more images may be generated using a variety of different imaging devices as described previously. The image data include an indication of a position of a first marker and an indication of a position of a second marker, as illustrated at step 104. The image data include position data for multiple positions of the markers during a range or path of motion of the dynamic body over a selected time interval. As described above, the image data include position data associated with multiple markers, however, only two are described here for simplicity. A distance between the position of the first marker and the position of the second marker is determined for multiple instants in time during the first time interval, at step 106. As also described above, the determination may include determining the distance based on the observable distance between the markers on a given image. The image data, including all of the images received during the first time interval, the position, and the distance data is recorded in a memory component at step 108.

Then at step 110, during a second time interval, while performing a medical procedure on patient 10 with PTD 20 positioned on patient 10 at substantially the same location, position data is received for a first localization element and a second localization element. Localization elements 24 of PTD 20 are proximate markers 22, such that the position data associated with localization elements 24 is used to determine the relative position of markers 22 in real-time during the medical procedure. The position data of localization elements 24 are recorded in a memory component at step 112.

A distance between the first and second localization elements is determined at step 114. Although only two localization elements 24 are described, as with the markers, position data associated with more than two localization elements may be received and the distances between the additional localization elements may be determined.

The next step is to determine which image from the population of images taken during the first time interval represents the relative position and/or orientation of the dynamic body at a given instant in time during the second time interval or during the medical procedure. To determine this, at step 116, the distance between the positions of the first and second localization elements at a given instant in time during the second time interval determined in step 114 are compared to the distance(s) determined in step 106 between the positions of the first and second markers obtained with the image data during the first time interval.

An image is selected from the first time interval that best represents the same position and orientation of the dynamic body at a given instant in time during the medical procedure. To do this, the difference between the distance between a given pair of localization elements during the second time interval is used to select the image that contains the same distance between the same given pair of markers from the image data received during the first time interval. This is accomplished, for example, by executing an algorithm to perform the calculations. When there are multiple pairs of markers and localization elements, the algorithm may sum the distances between all of the selected pairs of elements for a given instant in time during the second time interval and sum the distances between all of the associated selected pairs of markers for each instant in time during the first time interval when the pre-procedural image data was received.

When an image is found that provides the sum of distances for the selected pairs of markers that is substantially the same as the sum of the distances between the localization elements during the second time interval, then that image is selected at step 118. The selected image is then displayed at step 120. The physician or other healthcare professional may then observe the image during the medical procedure. Thus, during the medical procedure, the above process may be continuously executed such that multiple images are displayed and images corresponding to real-time positions of the dynamic body may be viewed.

In addition to tracking the location of PTD 20, navigation system 70 (see FIG. 3) may also track any type of device which includes one or more localization elements. The localization elements in the medical devices may be substantially similar or identical to localization elements 24 of PTD 20. The devices preferably include medical devices, including, but not limited to, steerable catheters, needles, stents, ablation probes, biopsy devices, guide wires, forceps devices, brushes, stylets, pointer probes, radioactive seeds, implants, endoscopes, energy delivery devices, therapy delivery devices, delivery of energy activated substances (e.g., porfimer sodium) and energy devices, radiofrequency (RF) energy devices, cryotherapy devices, laser devices, microwave devices, diffuse infrared laser devices, etc. In certain embodiments, the location of these devices are tracked in relation to PTD 20. In other embodiments, for example, these devices are tracked in relation to electromagnetic field generator 62, 82. It is also envisioned that at least some of these medical devices may be wireless or have wireless communications links. It is also envisioned that the medical devices may encompass medical devices which are used for exploratory purposes, testing purposes or other types of medical procedures.

Figure 11:
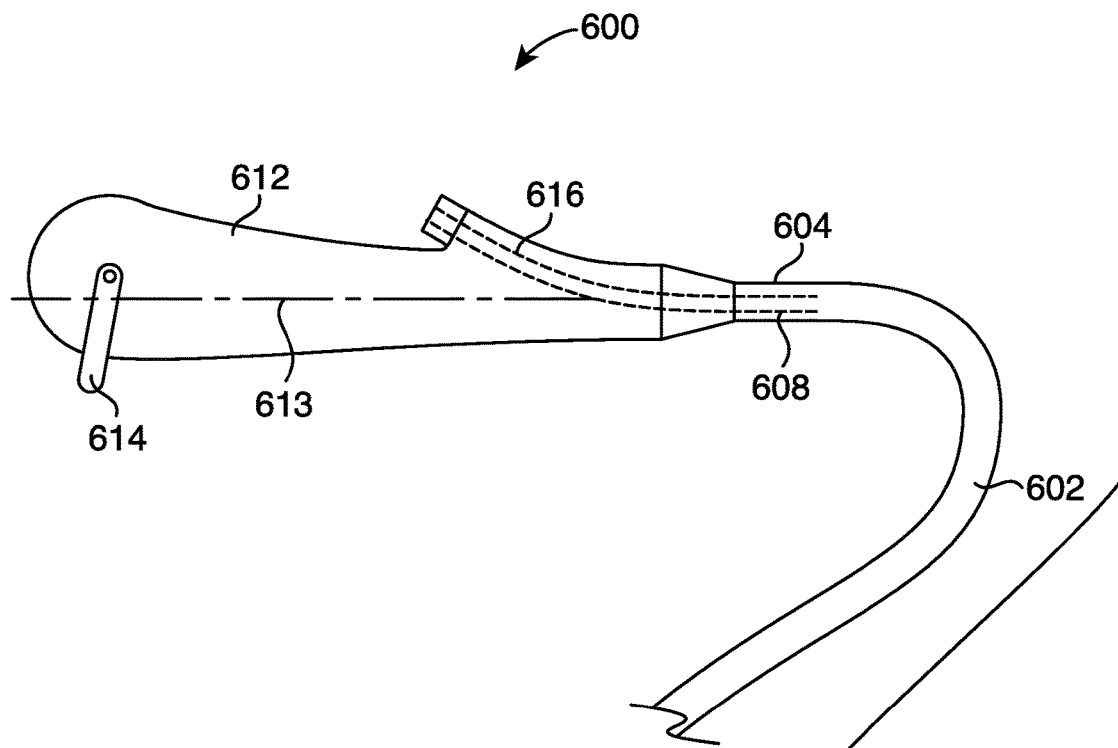
FIG. 11 is a left side view of a steerable catheter according to an embodiment of the invention.
Figure 11:
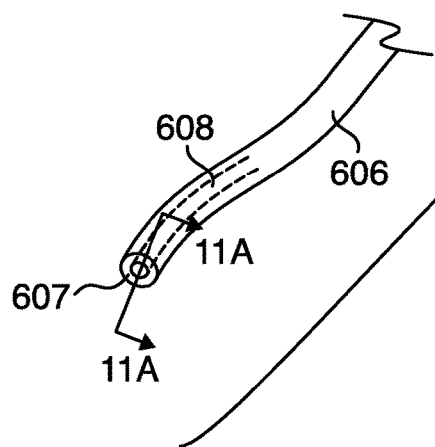
Figure 11A:
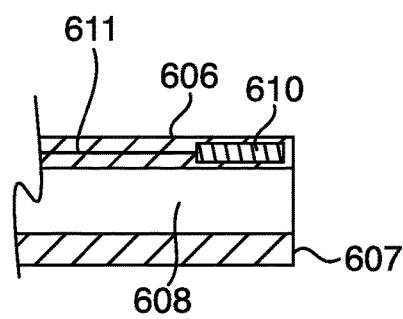
FIG. 11A is a left partial section view of a steerable catheter according to an embodiment of the invention.

One embodiment of a medical device which may be tracked by navigation system 70 is illustrated in FIGS. 11 and 11A. In one embodiment of the present invention, a navigated surgical catheter that is steerable 600 (referred herein to as "steerable catheter") may be used to gain access to, manipulate, remove, sample or otherwise treat tissue within the body including, but not limited to, for example, heart or lung tissue. Steerable catheter 600 comprises an elongate flexible shaft 602 having a proximal end portion 604, a distal end portion 606 terminating in tip 607, and one or more working channels 608 extending from proximal end portion 604 to tip 607. As shown in FIG. 11A, one or more localization elements 610 that are detectable by navigation system 70 are disposed proximate the distal end portion 606 of elongate flexible shaft 602. Accordingly, the position and orientation (POSE) of localization elements 610 are tracked by localization device 76 of navigation system 70. The one or more localization elements 610 are connected by wire 611 to navigation system 70; in alternative embodiments, the one or more localization elements 610 may be wirelessly connected to navigation system 70. In certain embodiments, localization elements 610 comprise six (6) degree of freedom (6DOF) electromagnetic coil sensors. In other embodiments, localization elements 610 comprise five (5) degree of freedom (5DOF) electromagnetic coil sensors. In other embodiments, localization elements 610 comprise other localization devices such as radiopaque markers that are visible via fluoroscopic imaging and echogenic patterns that are visible via ultrasonic imaging. In yet other embodiments, localization elements 610 may be, for example, infrared light emitting diodes, and/or optical passive reflective markers. Localization elements 610 may also be, or be integrated with, one or more fiber optic localization (FDL) devices. Accordingly, in certain embodiments, localization elements 610 may be substantially similar or identical to localization elements 24 of PTD 20. In other embodiments the steerable catheter may be non-navigated, such that it does not include any localization elements.

Steerable catheter 600 further comprises handle 612 attached to the proximal end portion 604 of elongate flexible shaft 602. Handle 612 of steerable catheter 600 includes steering actuator 614 wherein distal end portion 606 is moved "up" and "down" relative to proximal end portion 604 by manipulating steering actuator 614 "up" and "down," respectively. Additionally, distal end portion 606 is moved "left" and "right" relative to proximal end portion 604 by rotating handle 612 "left" and "right," respectively, about handle longitudinal axis 613. It will be understood that steering actuator 614 and handle 612 are connected to a steering mechanism (not shown) on the inside of steerable catheter 600 which is connected to distal end portion 606 of elongate flexible shaft 602 for causing the deflection in distal end portion 606. Port 616, disposed on handle 612, provides access to working channel(s) 608 in elongate flexible shaft 602 of steerable catheter 600, such that a medical device may be inserted into working channel(s) 608 through port 616.

Figure 12A:
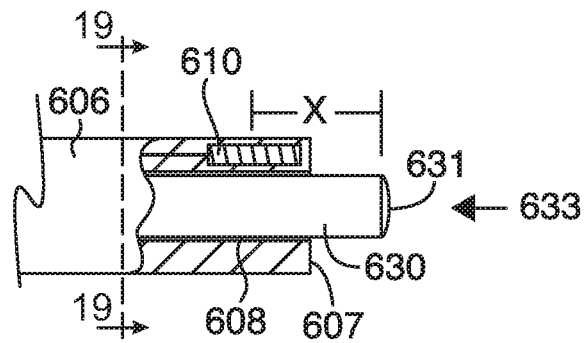
FIG. 12A is a left partial cut away view of a steerable catheter according to an embodiment of the invention.
Figure 12B:
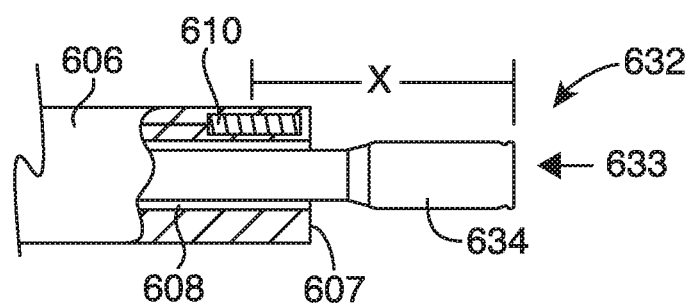
FIG. 12B is a left partial cut away view of a steerable catheter according to an embodiment of the invention.

As shown in FIGS. 12A and 12B, any number of medical devices or therapies may be inserted into working channel(s) 608 and/or extended out of tip 607 to deliver the medical devices or therapies to a target tissue. The medical devices may include, but are not limited to, imaging devices 633, tissue sensing devices 632, biopsy devices, therapy devices, steerable catheters, endoscopes, bronchoscopes, percutaneous devices, percutaneous needles, pointer probes, implants, stents, guide wires, stylets, etc. In certain embodiments, imaging devices 633 include, but are not limited to, bronchoscopic video cameras 630, endobronchial ultrasound (EBUS) devices 634, optical coherence tomography (OCT) devices, probe based Confocal Laser Endomicroscopy (pCLE) devices, or any known imaging device insertable into working channel 608 of steerable catheter 600. Tissue sensing device 632 may be any type of device which may be used to determine the presence of a target tissue in patient 10. In certain embodiments, tissue sensing device 632 may include, but is not limited to, imaging device 633, a cell analysis device, a cancer detecting device, an exhaled breath condensate analyzer, a physiological characteristic sensor, a chemical analysis device, an aromatic hydrocarbon detection device, vacuum collection device, etc. The sensitivity of certain of the tissue sampling devices, such as aromatic hydrocarbon detection devices are dependent upon the density of the sample collected. Thus, by navigating steerable catheter 600 near the desired target tissue a sample of higher density may be captured and analyzed. Additionally, a vacuum collection device may be navigated using steerable catheter 600 to near the desired target tissue and/or an airway branch within one or two segments of the desired target tissue, and an air sample may be captured. In certain embodiments, therapy devices include, but are not limited to, ablation probes, energy delivery devices, radioactive seeds, delivery of energy activated substances (e.g., porfimer sodium) and energy devices, radiofrequency (RF) energy devices, cryotherapy devices, laser devices, microwave devices, diffuse infrared laser devices, fluids, drugs, combinations thereof, or the like). In certain embodiments, biopsy devices include, but are not limited to, needles, forceps devices, brushes, etc. In certain embodiments, steerable catheter 600 may also include a suction capability.

As illustrated in FIG. 12A, for example, in certain embodiments, imaging device 633 is a bronchoscopic video camera 630. Bronchoscopic video camera 630 may be inserted into working channel 608 and/or extended out distal end portion 606 of navigated steerable catheter 600. By inserting bronchoscopic video camera 630 into working channel 608 of steerable catheter 600, steerable catheter 600 may be used like a typical steerable bronchoscope, as described more fully elsewhere herein.

As shown in FIG. 12B, tissue sensing device 632 may be an imaging device 633, wherein imaging device 633 is an endobronchial ultrasound (EBUS) device 634; however, as described above, it will be understood that imaging device 633 may include, but is not limited to, bronchoscopic video camera 630, an optical coherence tomography (OCT)

device, a probe based Confocal Laser Endomicroscopy (pCLE) device, or any known imaging device insertable into working channel 608 of steerable catheter 600.

In embodiments, where tissue sensing device 632 is imaging device 633, imaging device 633 may be able to generate a population of images of the target tissue(s), wherein the target tissue(s) may be in the airway, on the wall of the airway, in the wall of the airway, and/or beyond the wall of the airway. That is, the imaging device(s) may be able to generate images of target tissue(s) not only inside the airway, but may generate images of target tissue(s) and other anatomical structures inside and/or beyond the wall of the airway. Thus in certain embodiments, sub-surface target tissue may be imaged using the imaging device(s). Accordingly, using endobronchial ultrasound (EBUS) device 634, an optical coherence tomography (OCT) device, a probe based Confocal Laser Endomicroscopy (pCLE) device, etc. while tracking the position and orientation (POSE) of localization element 610 of steerable catheter 600, as described herein, multiple 3D volumes of image data regarding target tissue(s) and other anatomical structures inside and/or beyond the wall of the airway may be collected and a larger 3D volume of collected data may be constructed. Knowing the 3D location and orientation of the multiple 3D volumes will allow the physician or other healthcare professional to view a more robust image of, for example, pre-cancerous changes of target tissue(s) in patient 10. This data may also be correlated to pre-acquired or intra-procedurally acquired image dataset 400 to provide additional information.

Additionally, in certain embodiments wherein steerable catheter 600 includes multiple working channels 608, multiple medical devices may be inserted into the multiple working channels 608. For example, bronchoscopic video camera 630 may be inserted into one working channel and a medical device such as a needle, forceps device or a brush may be inserted into a second working channel. Accordingly, a real-time image feed from bronchoscopic video camera 630 may be used to view the operation of the medical device. Although a steerable catheter has been described, it will be understood that any type of steerable medical device may be used in accordance with the methods described herein, including, but not limited to, endoscopes, bronchoscopes, etc. without departing from the scope of the invention.

Figure 13:
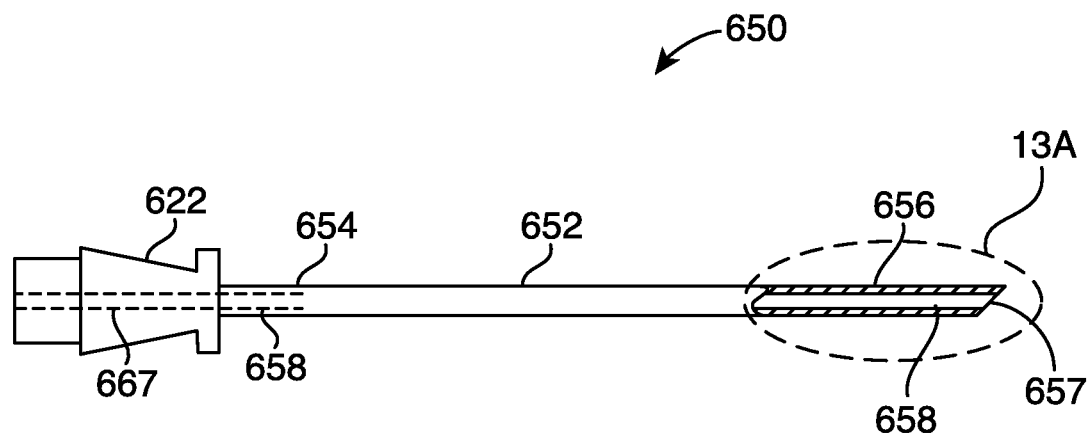
FIG. 13 is a left side view of a percutaneous needle according to an embodiment of the invention.
Figure 13A:
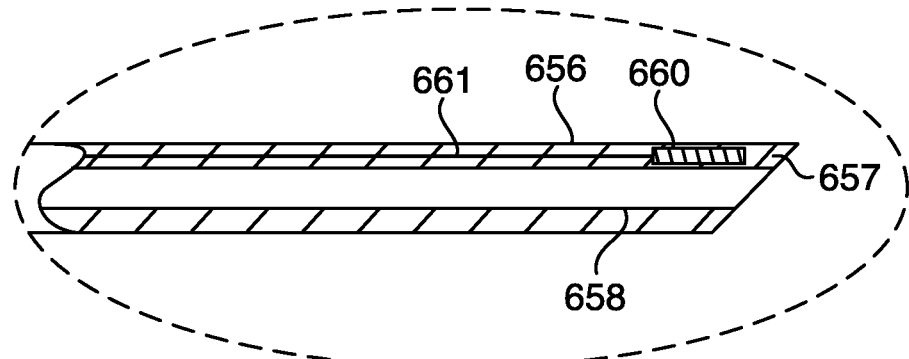
FIG. 13A is a left partial cut away view of a percutaneous needle according to an embodiment of the invention.

Another embodiment of a medical device which may be tracked by navigation system 70 is illustrated in FIGS. 13 and 13A. In one embodiment of the present invention, a percutaneous needle 650 may be used to gain access to, manipulate, remove, sample or otherwise treat target tissue within patient 10 including, but not limited to, for example, target tissue on and/or in the heart or lung. Percutaneous needle 650 comprises an elongate shaft or cannula 652 having a proximal end portion 654, a distal end portion 656 terminating in tip 657, and one or more working channels 658 may extend from proximal end portion 654 to tip 657. Percutaneous needle 650 further includes handle 652 attached to the proximal end portion 654. Port 667, disposed on handle 652, provides access to working channel(s) 658 in cannula 652 of percutaneous needle 650, such that a medical device may be inserted into working channel(s) 658 through port 667. Any number of medical devices or therapies, as described herein, may be inserted into working channel(s) 658 and/or extended out of tip 657 to deliver the medical devices or therapies (e.g., steerable catheters, needles, stents, ablation probes, biopsy devices, guide wires, forceps devices, brushes, stylets, pointer probes, radioactive seeds, implants, endoscopes, energy delivery devices, therapy delivery devices, delivery of energy activated substances (e.g., porfimer sodium) and energy devices, radiofrequency (RF) energy devices, cryotherapy devices, laser devices, microwave devices, diffuse infrared laser devices, fluids, drugs, combinations thereof, or the like) to a target tissue.

As shown in FIG. 13A, one or more localization elements 660 that are detectable by navigation system 70 are disposed proximate the distal end portion 656 of cannula 652. Accordingly, the position and orientation (POSE) of localization elements 660 are tracked by localization device 76 of navigation system 70. The one or more localization elements 660 are connected by wire 661 to navigation system 70; in alternative embodiments, the one or more localization elements 660 may be wirelessly connected to navigation system 70.

In certain embodiments, localization elements 660 comprise six (6) degree of freedom (6DOF) electromagnetic coil sensors. In other embodiments, localization elements 660 comprise five (5) degree of freedom (5DOF) electromagnetic coil sensors. In other embodiments, localization elements 660 comprise other localization devices such as radiopaque markers that are visible via fluoroscopic imaging and echogenic patterns that are visible via ultrasonic imaging. In yet other embodiments, localization elements 660 may be, for example, infrared light emitting diodes, and/or optical passive reflective markers. Localization elements 660 may also be, or be integrated with, one or more fiber optic localization (FDL) devices. Accordingly, in certain embodiments, localization elements 660 may be substantially similar or identical to localization elements 24 of PTD 20 and/or localization elements 610 of steerable catheter 600.

While localization element 660 is illustrated proximate distal end portion 656, it will be understood that localization element 660 may be located in other locations of percutaneous needle 650 without departing from the scope of the invention. For example, in certain embodiments, localization element 660 may be disposed proximate the proximal end portion 654 and/or proximate handle 662. Navigation system 70 may be able to determine the location of tip 657 in relation to the location of PTD 20 by knowing the location of localization element 660 in relation to tip 657. For example, if localization element 660 is disposed at handle 662, navigation system 770 may be able to determine the location of tip 657 in relation to the position of localization element 660 if the length between tip 657 and localization element 660 is input into navigation system 70.

In other embodiments, percutaneous needle 650 is non-navigated, such that it does not include any localization elements. However, the location of percutaneous needle 650 may still be tracked by navigation system 70 if a medical device containing a localization element is inserted into working channel 658 of percutaneous needle 650.

In various embodiments, any of the medical devices described herein that may be inserted into working channel(s) 608, 658 of steerable catheter 600 and/or percutaneous needle 650 may be tracked individually with an integrated localization element (e.g., an electromagnetic (EM) sensor). Accordingly, the medical devices may be tip tracked. Additionally, wherein the inserted medical device is an ablation probe, ablation models may be displayed to assist in optimal placement of the ablation probe for treatment. It will be understood that the medical devices may be delivered endobronchially, percutaneously, and/or endobronchially and percutaneously simultaneously.

Referring again to navigation system 70, navigation system 70 may display on display 80 multiple images which may assist a physician or other healthcare professional in conducting the methods described herein. Image dataset 400 generated during the first time interval may be registered to patient 10 using PTD 20. As described above, localization elements 24 of PTD 20 are proximate markers 22 and because one or more markers 22 of PTD 20 are visible in image dataset 400 and localization elements 24 corresponding to the one or more markers 22 are tracked by navigation system 70, image dataset 400 may be registered to patient 10. This registration may be manually accomplished or may be automatically accomplished by navigation system 70.

In addition to or alternative to registration using PTD 20, registration may be completed by different known techniques. First, point-to-point registration may be accomplished by identifying points in an image space and then touching the same points in patient space. These points are generally anatomical landmarks that are easily identifiable on the patient. Second, lumen registration may be accomplished by generating a point cloud within the airways of patient 10 and matching the shape of the generated point cloud to an inspiration 3D airway model 410, an expiration 3D airway model 412, and/or a hybrid "Inspiration-Expiration" 3D airway model 414. Using four-dimensional tracking (4D) the point cloud may be generated at the appropriate respiration cycle to match inspiration 3D airway model 410, an expiration 3D airway model 412, and/or a hybrid "Inspiration-Expiration" 3D airway model 414. Generation of a point cloud is more fully described in U.S. Ser. No. 13/773,984, entitled "Systems, Methods and Devices for Forming Respiratory-Gated Point Cloud for Four Dimensional Soft Tissue Navigation," filed on Feb. 22, 2013, which is hereby incorporated by reference. Third, surface registration may involve the generation of a surface in patient 10 space by either selecting multiple points or scanning, and then accepting the best fit to that surface in image space by iteratively calculating with processor 72 until a surface match is identified. Fourth, repeat fixation devices entail repeatedly removing and replacing a device (i.e., dynamic reference frame, etc.) in known relation to patient 10 or image fiducials of patient 10. Fifth, two-dimensional (2D) image datasets may be registered to three-dimensional (3D) image datasets wherein, the two dimensional image datasets may include, but are not limited to, fluoroscopic images, ultrasound images, etc. and the three-dimensional (3D) image datasets may include, but are not limited to, computed tomography (CT) images, fused computed tomography-positron emission tomography (CT/PET) images, magnetic resonance imaging (MRI) images. Sixth, automatic registration may be accomplished by first attaching a dynamic reference frame to patient 10 prior to acquiring image data. It is envisioned that other known registration procedures are also within the scope of the present invention, such as that disclosed in U.S. Pat. No. 6,470,207, entitled Navigational Guidance via Computer-Assisted Fluoroscopic Imaging", filed on Mar. 23, 1999, which is hereby incorporated by reference.

Figure 14:
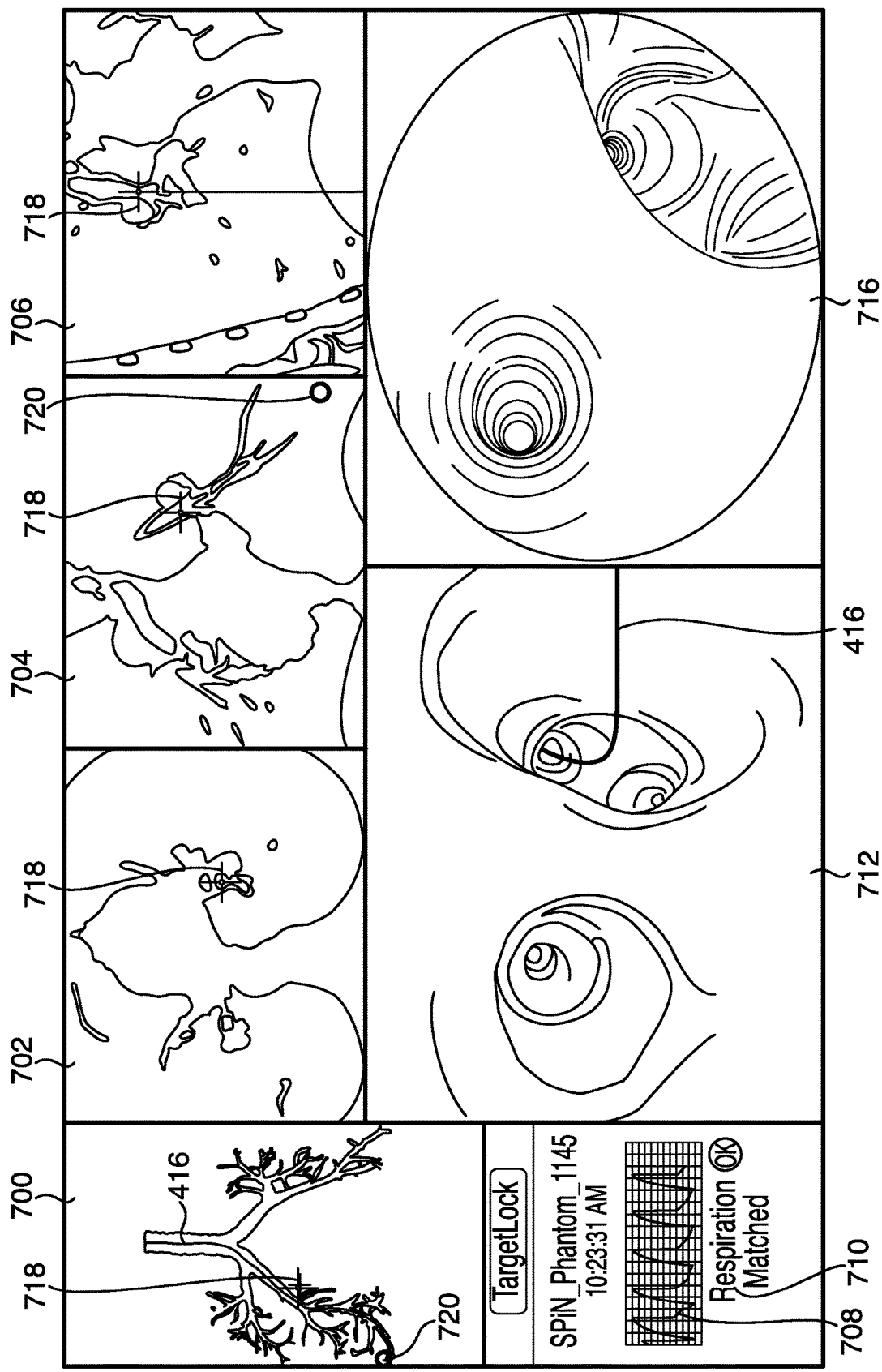
FIG. 14 illustrates a population of images which may be displayed on a display of a navigation system according to an embodiment of the invention.

After image dataset 400 is registered to patient 10, navigation system 70 displays on display 80 a variety of images as illustrated in FIG. 14. For example, as shown in panel 700, hybrid "Inspiration-Expiration" 3D airway model 414 may be displayed. Additionally, as shown in panel 700, an indicia 718 (shown as a crosshair) of the location of steerable catheter 600 is displayed. In certain embodiments, for example, indicia 718 indicates the location of distal end portion 606 of steerable catheter 600. In other embodiments, for example, indicia 718 indicates the location of localization element 610 of steerable catheter 600. In yet other embodiments, for example, indicia 718 indicates the location of tip 607 of steerable catheter 600. That is, navigation system 70 may be able to display an indicia indicating the location of a portion of steerable catheter 600 based on the tracked location of localization element 610. For example, if localization element 610 is disposed 5 mm from tip 607 of steerable catheter 600, the 5 mm distance may be taken into account by navigation system 70 and the indicia of tip 607 indicating the location of tip 607 may be displayed and not the location of localization element 610. An indicia 720 (shown as a circle) of an initial target tissue location may also be displayed on display 80 by navigation system 70 as shown in panel 700. Indicia 718, 720 are shown as a crosshair and circle, respectively; however it is envisioned that other indicia may be used to indicate the location of steerable catheter 600, initial target tissue location, confirmed target tissue location, location of percutaneous needle 650, and/or any other target tissue or medical device. For example, indicia may have different shapes, colors, sizes, line weights and/or styles, etc. without departing from the scope of the invention.

Furthermore, navigation system 70 may be able to simulate and display axial, coronal and oblique images based on the position and orientation (POSE) of localization element 610 of steerable catheter 600, as shown in panels 702, 704, and 706. To simulate these views, navigation system 70 may modify one or more images from image dataset 400 using known image manipulation techniques. Additionally, navigation system 70 may simulate and/or display orthogonal image slices, oblique or off-axis image slices, volume rendered images, segmented images, fused modality images, maximum intensity projection (MIPS) images, video, and video enhanced images. As shown, indicia of 718 of steerable catheter 600 and/or an indicia 720 of an initial target tissue location may also be displayed, as shown in panels 702, 704, and 706.

In various embodiments as shown in panel 712, navigation system 70 also simulates a virtual volumetric scene within the body of patient 10, such as the airways of patient 10, from a point of view of a medical device, such as steerable catheter 600, as it is being navigated into and/or through patient 10. This virtual volumetric scene is a computer-generated visualization of a bronchoscopy procedure and simulates what would be viewed by a bronchoscopic video camera inserted into the airways. To simulate the virtual volumetric scene, navigation system 70 modifies one or more images from image dataset 400 using known image manipulation techniques. For example, navigation system 70 may be able to simulate the virtual volumetric scene using inspiration 3D airway model 410, expiration 3D airway model 412, and/or hybrid "Inspiration-Expiration" 3D airway model 414. Accordingly navigation system 70 renders an internal view of 3D airway model(s) 410, 412, and/or 414 based on a virtual bronchoscope video camera position, for example, by applying certain surface properties (e.g., Lambertian), diffuse shading model(s), and perspective projection camera model(s). Virtual lighting and shading may be applied to the rendered view to further enhance the virtual volumetric scene. The field of view (FOV) may be changed to match the field of view of bronchoscopic video camera 630 (see FIG. 12A). The point of view may be adjusted to match bronchoscopic video camera 630 or to display a virtual volumetric scene from different points along the airway or outside the airway. Navigation system 70 may also be able to display a navigation pathway 416 in the virtual volumetric scene. Accordingly, the virtual volumetric scene may allow a physician or other healthcare professional to review the navigation pathway 416 prior to inserting steerable catheter 600 and/or other medical device into patient 10. Additionally, in certain embodiments, an indicia of the location of localization element 610 of steerable catheter 600 and/or an indicia of an initial target tissue location may also be displayed.

Additionally, in various embodiments as shown in panel 716, navigation system 70 also displays a real-time image feed from bronchoscopic video camera 630 inserted into working channel 608 of steerable catheter 600. The real-time image feed may be static images or moving video. The real-time image feed may assist the physician or other healthcare professional in navigating steerable catheter 600 to proximate the initial location of the target tissue. Thus by inserting bronchoscopic video camera 630 into working channel 608 of steerable catheter 600 (see FIG. 12A), steerable catheter 600 may be used like a typical steerable bronchoscope. Typical steerable bronchoscopes are used to visually inspect the airways of a patient and have a fixed bronchoscopic video camera in addition to one or more working channels. Typical steerable bronchoscopes may have steering actuators and steering mechanisms that permit them to be steered much like steerable catheter 600. Because the bronchoscopic video camera of a typical steerable bronchoscope is fixed during manufacture of the steerable bronchoscope, the "up" orientation of the image feed from the bronchoscopic video camera as displayed to the physician or other healthcare professional is aligned with the "up" direction of the steering actuator of the typical steerable bronchoscope. That is, the orientation of the real-time image feed from the typical steerable bronchoscope is registered to the orientation of the steering directions of the typical steerable bronchoscope. Accordingly, when the physician or other healthcare professional steers the typical steerable bronchoscope "up," the image feed will move "up." Additionally, steering the typical steerable bronchoscope "down," "left," and "right," the image feed will move "down," "left," and "right," respectively.

However, because the bronchoscopic video camera is fixed (i.e., non-removable) in the typical steerable bronchoscope, the outside diameter of the typical steerable bronchoscope must be large enough to also accommodate one or more working channels. Due to the large outside diameter of typical steerable bronchoscopes, certain portions of the airways may be unreachable by the steerable catheter because the diameter of the airway may be too small. Accordingly, it may be desirable to use steerable catheter 600 which may have a smaller outside diameter than the typical steerable bronchoscope. Bronchoscopic video camera 630 may be inserted working channel 608 of steerable catheter 600 and a real-time image feed is displayed to the physician or other healthcare professional. Using the real-time image feed, the physician or other healthcare professional may navigate steerable catheter 600 to very small diameter portions of the airway which were previously inaccessible by a typical steerable bronchoscope. Once the physician or other healthcare professional has reached the desired target tissue with steerable catheter 600, the physician or other healthcare professional may remove bronchoscopic video camera 630 from working channel 608 of steerable catheter 600 and insert one or more other medical devices into working channel 608 as described more fully elsewhere herein. Additionally, because bronchoscopic video camera 630 is not fixed in steerable catheter 600, the ratio(s) of the diameter(s) of working channel(s) 608 of steerable catheter 600 to the outside diameter of steerable catheter 600 may be much higher than the ratio(s) of the diameter(s) of working channel(s) of a typical steerable bronchoscope to the outside diameter of a typical steerable bronchoscope.

While the removable nature of bronchoscopic video camera 630 provides the above mentioned benefits, because the bronchoscopic video camera 630 is not fixed in steerable catheter 600, the "up" orientation of the image feed from bronchoscopic video camera 630 as displayed to the physician or other healthcare professional may not be aligned with the "up" direction of steering actuator 614 of steerable catheter 600. That is, depending on how the physician or other healthcare professional inserts bronchoscopic video camera 630 into working channel 608 of steerable catheter, what appears as "up" in the real-time image feed from bronchoscopic video camera 630 may not correspond to an "up" steering input to steering actuator 614. Accordingly, the real time image feed may be rotated relative to the expected steering direction. This may introduce uncertainty and or confusion to the physician or other healthcare professional. For example, the physician or other healthcare professional may see an airway on the left hand side of the displayed real-time image feed and may accordingly manipulate handle 612 of steerable catheter to cause distal end portion 606 of steerable catheter 600 to steer left. However, because the orientation of the real-time image feed is not aligned with the with steering actuator 614 of steerable catheter 600, the airway that the physician or other healthcare professional thought was on the left hand side of the real-time image feed is not actually reachable by a left hand steering input to steerable catheter 600. Accordingly, the orientation of the image feed from bronchoscopic video camera 630 as displayed to the physician or other healthcare professional may not be aligned with steering actuator 614 of steerable catheter 600. Thus, to ensure that the physician or other healthcare professional is navigating down the desired airway, the "up" orientation of the real-time image feed from bronchoscopic video camera 630 as displayed to the physician or other healthcare professional should be aligned with the "up" direction of steering actuator 614 of steerable catheter 600.

Figure 15:
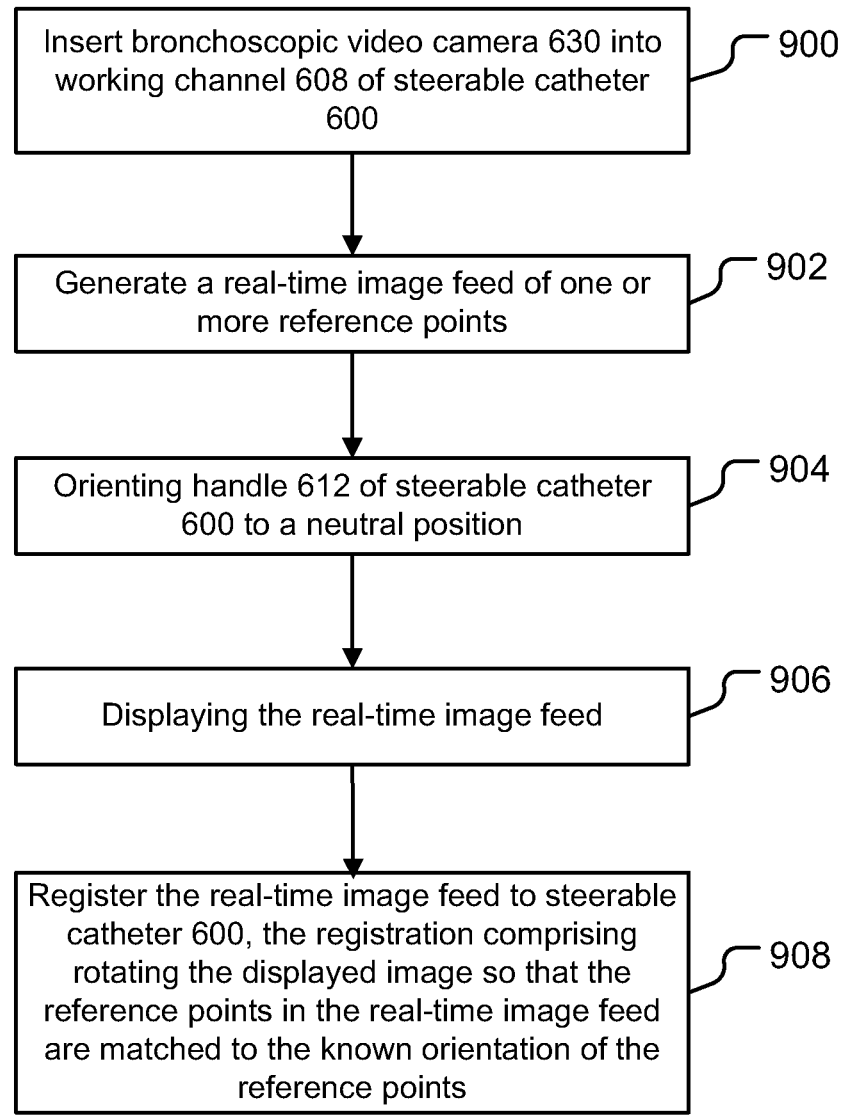
FIG. 15 is a flowchart illustrating a method of registering the real-time image feed from a bronchoscopic video camera to a steerable catheter according to an embodiment of the invention.

Referring now to FIG. 15, one method of registering the real-time image feed from a bronchoscopic video camera 630 to a steerable catheter 600 is described. At step 900, bronchoscopic video camera 630 is inserted into working channel 608 of steerable catheter 600. In certain embodiments, tip 631 (see FIG. 12A) of bronchoscopic video camera 630 is positioned proximate or extended past tip 607 of steerable catheter 600. At step 902, a real-time image feed of one or more reference points is generated using bronchoscopic video camera 630, wherein the orientation of the reference point(s) is known. That is, the physician or other healthcare professional may know or ascertain the orientation of the reference point(s) independently from the real-time image feed. At step 904, the physician or other healthcare professional orients handle 612 of steerable catheter 600 to a neutral position. Preferably, handle 612 of steerable catheter 600 is considered to be in a neutral position when longitudinal axis 613 of handle 612 is substantially vertical, when no "up" or "down" steering input is applied to steerable catheter 600 by steering actuator 614, and when no "left" or "right" steering input is applied to steerable catheter 600 by rotation of handle 612 about longitudinal axis 613. When in the neutral position, it is not required that elongate flexible shaft 602 of steerable catheter 600 be straight. Elongate flexible shaft 602 may be flexed; however it is contemplated that no additional steering inputs are applied to steerable catheter 600.

At step 906, the real-time image feed of bronchoscopic video camera 630 is displayed on display 80 of navigation system 70. At step 908, the real-time image feed is registered to steerable catheter 600 by rotating the displayed real-time image feed so that the reference point(s) in the real-time image feed are matched to the known orientation of the reference point(s). In certain embodiments, the physician or healthcare professional manually rotates the real-time image feed on display 80 of navigation system 70 using user interface device 84 (e.g., keyboard, mouse). In other embodiments, for example, navigation system 70 may automatically rotate the real-time image feed on display 80 of navigation system 70.

Optionally, the registration may be confirmed by steering steerable catheter 600 to cause a deflection of distal end portion 606 of elongate flexible shaft 602 in a direction and observing that the displayed real-time image feed moves in that same direction. For example, if physician or other healthcare professional manipulates steering actuator 614 to cause an "up" deflection in distal end portion 606 of elongate flexible shaft 602, the displayed real-time image feed will also move "up." Similarly, if the physician or other healthcare professional manipulates steering actuator 614 to cause a "down" deflection in distal end portion 606 of elongate flexible shaft 602, the displayed real-time image feed will also move "down." Additionally, if the physician or other healthcare professional rotates handle 612 "left" or "right" to cause a "left" or "right" deflection in distal end portion 606 of elongate flexible shaft 602, the displayed real-time image feed will also move "left" or "right." Accordingly, after the real-time image feed is registered to steerable catheter 600, what is displayed as "up," "down," "left," and/or "right," corresponds to "up," "down," "left," and "right" steering inputs to steerable catheter 600. That is, the orientation of the displayed real-time image feed is matched to the steering mechanics of steerable catheter 600.

Figure 16:
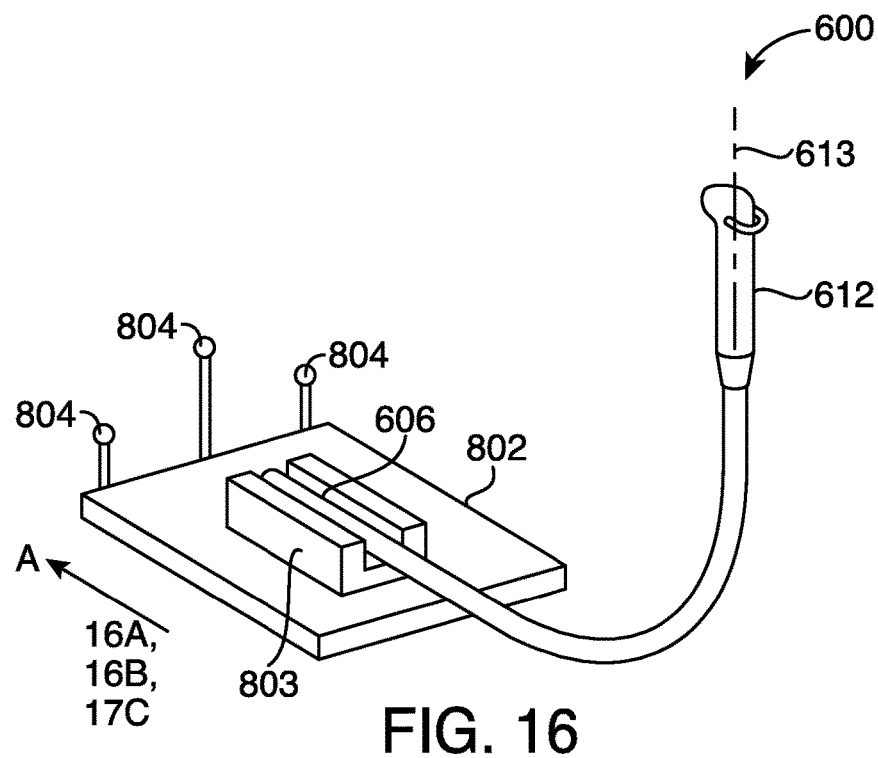
FIG. 16 is a left perspective view of a steerable catheter in a jig for registering the real-time image feed from a bronchoscopic video camera to a steerable catheter according to an embodiment of the present invention.
Figure 16A:
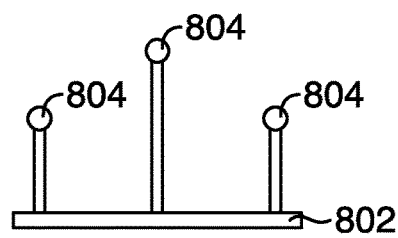
FIG. 16A is a front view of a steerable catheter in a jig for registering the real-time image feed from a bronchoscopic video camera to a steerable catheter according to an embodiment of the present invention.
Figure 16B:
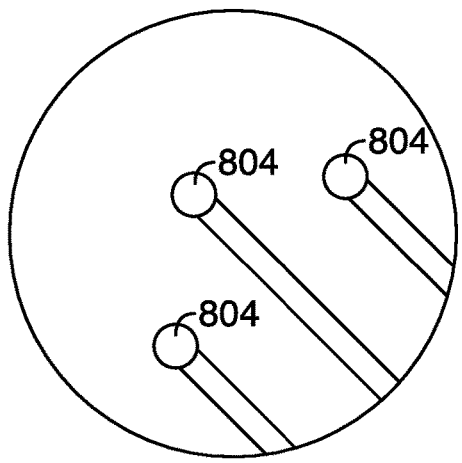
FIG. 16B is an image from a real-time image feed from a non-registered bronchoscopic video camera in a steerable catheter according to an embodiment of the present invention.
Figure 16C:
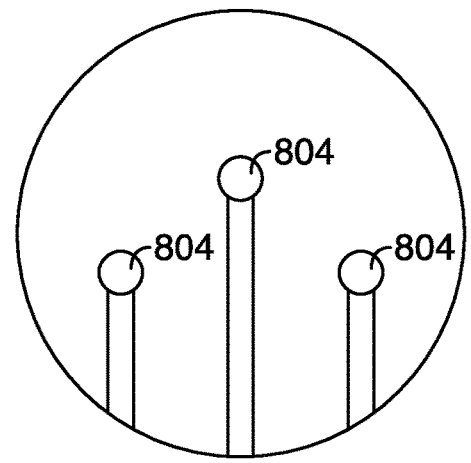
FIG. 16C is an image from a real-time image feed from a registered bronchoscopic video camera in a steerable catheter according to an embodiment of the present invention.

As shown in FIGS. 16 and 16A-16C, a jig 802 may be used in conjunction with the method of registering the real-time image feed from a bronchoscopic video camera 630 to a steerable catheter 600 described in FIG. 15. As shown in FIG. 16, jig 802 may include receiver 803 into which distal end portion 606 of steerable catheter 600 may be placed. Jig 802 further includes three round objects 804 which serve as the reference points described above. Accordingly, when viewed along arrow A, round objects 804 are known to be oriented as shown in FIG. 16A. When placed in jig 802, bronchoscopic video camera 630 is inserted into working channel 608 of steerable catheter 600 and handle 612 of steerable catheter 600 is oriented in a neutral position, as described above. Thus if the three round objects 804 are rotated a certain angle in the displayed real-time image feed from bronchoscopic video camera 630 as shown in FIG. 16B, the real-time image feed needs to be registered by rotating the displayed real-time image feed so that the three round objects 804 in the real-time image feed are matched to the known orientation of the three round objects 804 as shown in FIG. 16C. While reference points are illustrated as three round objects 804, it will be understood that any shape object may be used as a reference point, including, but not limited to, a T-shaped object, a cross-shaped object, a square shaped object, etc. Additionally, while three reference points are illustrated, it will be understood that jig 802 may include one or more reference points. In other embodiments, for example, jig 802 may include a picture or pattern which serves as the one or more reference points.

Figure 17:
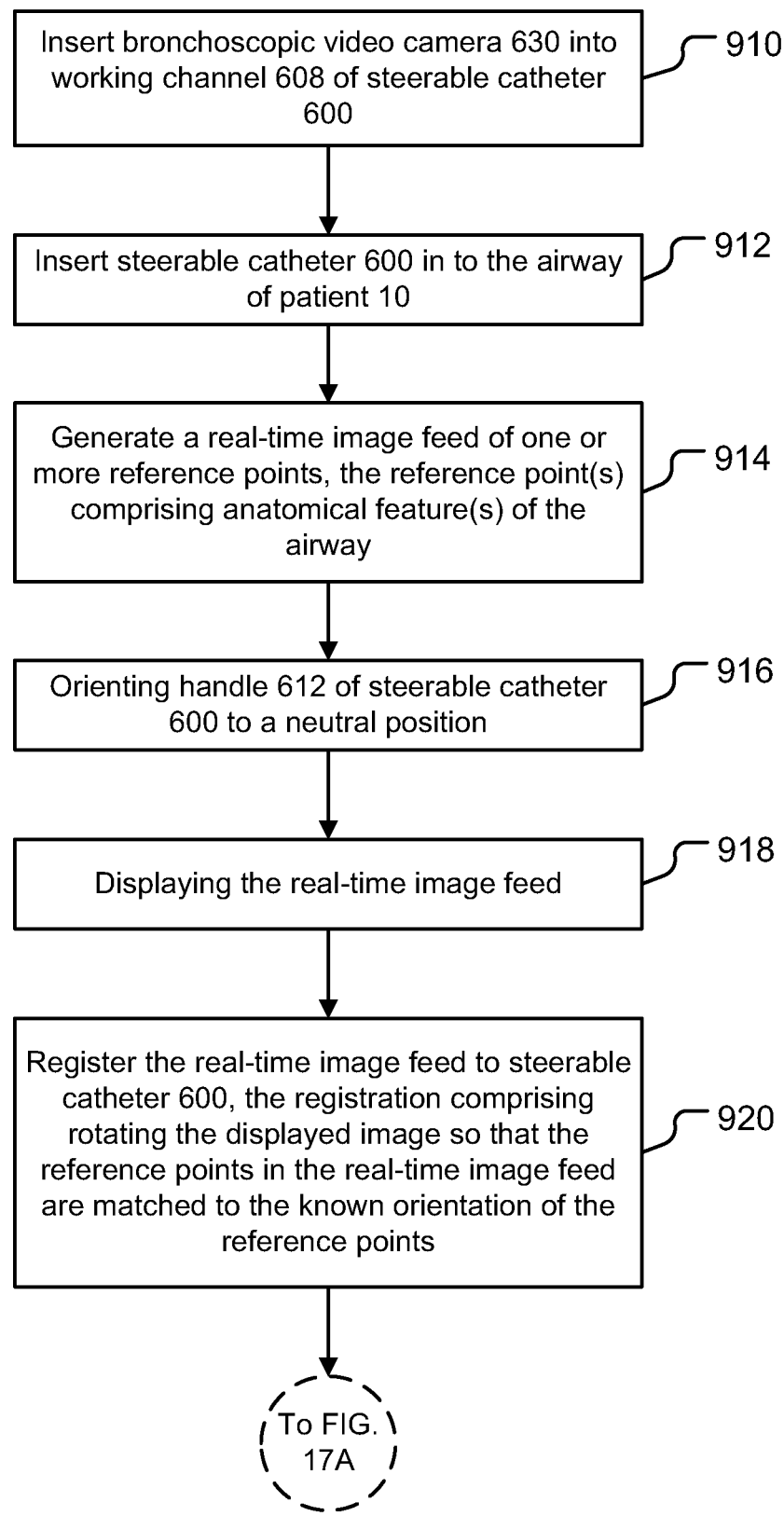
FIG. 17 is a flowchart illustrating a method of registering the real-time image feed from a bronchoscopic video camera to a steerable catheter according to an embodiment of the invention.

Another embodiment of the method of registering the real-time image feed from a bronchoscopic video camera 630 to a steerable catheter 600 is shown in FIG. 17. At step 910, bronchoscopic video camera 630 is inserted into working channel 608 of steerable catheter 600. In certain embodiments, tip 631 (see FIG. 12A) of bronchoscopic video camera 630 is positioned proximate or extended past tip 607 of steerable catheter 600. At step 912, steerable catheter 600 is inserted into the airway of patient 10. At step 914, a real-time image feed of one or more reference points is generated using bronchoscopic video camera 630, the reference point(s) comprising anatomical feature(s) of the airway wherein the orientation of the anatomical feature(s) is known. In certain embodiments, the anatomical feature(s) may include the right main bronchus (RMB) and the left main bronchus (LMB).

Figure 18A:
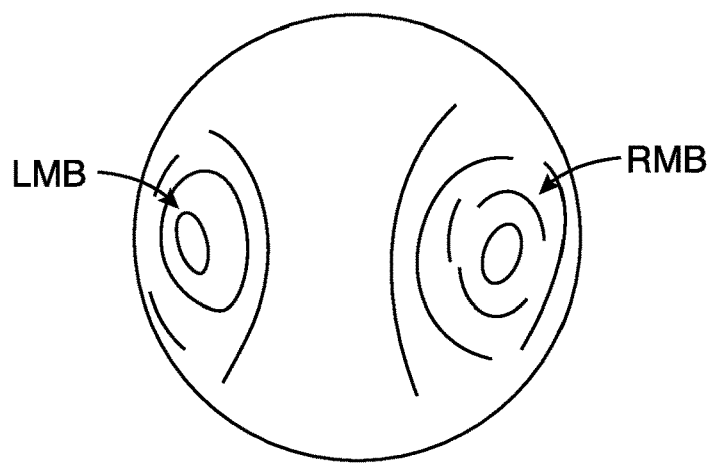
FIG. 18A is an image of an expected orientation of anatomical features in the airway of the patient according to an embodiment of the invention.

As shown in FIG. 18A, it is generally understood that the RMB and the LMB of most patients are oriented at about a 3 o'clock position and about a 9 o'clock position respectively when viewed with a typical steerable bronchoscope. Referring again to FIG. 17, at step 916, the physician or other healthcare professional orients handle 612 of steerable catheter 600 to a neutral position. Preferably, handle 612 of steerable catheter 600 is considered to be in a neutral position when longitudinal axis 613 of handle 612 is substantially vertical, when no "up" or "down" steering input is applied to steerable catheter 600 by steering actuator 614, and when no "left" or "right" steering input is applied to steerable catheter 600 by rotation of handle 612 about longitudinal axis 613. When in the neutral position, it is not required that elongate flexible shaft 602 of steerable catheter 600 be straight. Elongate flexible shaft 602 may be flexed; however it is contemplated that no additional steering inputs are applied to steerable catheter 600.

At step 918, the real-time image feed of bronchoscopic video camera 630 is displayed on display 80 of navigation system 70. As shown in FIG. 18B, the displayed real-time image feed of bronchoscopic video camera 630 shows the RMB and LMB rotated such that the RMB appears at about a 2 o'clock position and the LMB appears at about an 8 o'clock position. At step 920, the real-time image feed is registered to steerable catheter 600 by rotating the displayed real-time image feed so that the anatomical feature(s) in the real-time image feed are matched to the known orientation of the anatomical feature(s). Thus as shown in FIG. 18C, after registration, the displayed real-time image feed of bronchoscopic video camera 630 shows the RMB and LMB at about a 3 o'clock position and at about a 9 o'clock position, respectively. In certain embodiments, the physician or healthcare professional manually rotates the real-time image feed on display 80 of navigation system 70 using user interface device 84 (e.g., mouse). In other embodiments, for example, navigation system 70 may automatically rotate the real-time image feed on display 80 of navigation system 70. The method may optionally continue according to steps illustrated in FIG. 17A as described more fully elsewhere herein.

Optionally, the registration may be confirmed by steering steerable catheter 600 to cause a deflection of distal end portion 606 of elongate flexible shaft 602 in a direction and observing that the displayed real-time image feed moves in that same direction. For example, if physician or other healthcare professional manipulates steering actuator 614 to cause an "up" deflection in distal end portion 606 of elongate flexible shaft 602, the displayed real-time image feed will also move "up." Similarly, if the physician or other healthcare professional manipulates steering actuator 614 to cause a "down" deflection in distal end portion 606 of elongate flexible shaft 602, the displayed real-time image feed will also move "down." Additionally, if the physician or other healthcare professional rotates handle 612 "left" or "right" to cause a "left" or "right" deflection in distal end portion 606 of elongate flexible shaft 602, the displayed real-time image feed will also move "left" or "right." Accordingly, after the real-time image feed is registered to steerable catheter 600, what is displayed as "up," "down," "left," and "right," corresponds to "up," "down," "left," and "right" steering inputs to steerable catheter 600.

In some embodiments, the registration of the real-time image feed to steerable catheter 600 may be enhanced by correcting image distortion in the real time image feed. For example, bronchoscopic video cameras typically include fish-eye lenses which increase the field of view of the bronchoscopic video camera thus providing the physician or other healthcare professional with a larger view of the airway of patient 10. However, the fish-eye lenses introduce barrel distortion into the real-time image feed. Due to this barrel distortion, the interpretation of the real-time image feed may be compromised. Correcting for this image distortion in the real-time image feed provides a more accurate depiction of the airway of patient 10, thus permitting an enhanced registration of the real-time image feed to steerable catheter 600.

Referring again to FIG. 14, in yet other embodiments, the virtual volumetric scene displayed in panel 712 may be registered to the real-time image feed from a bronchoscopic video camera 630 displayed in panel 716. However, as steerable catheter 600 is navigated through the airways of patient 10, steerable catheter 600 may be positioned in such a way such that what appears "up" in the real-time image feed may not correspond to the physical "up" direction of patient 10. That is, the physical "up" of patient 10 usually corresponds to the anterior direction of patient 10 as patient 10 is oriented during the procedure. Typically, patient 10 is in the supine position and thus, the physical "up" of the patient will correspond to an actual "up." However, in certain situations, patient 10 may be in different orientations during the procedure, such as on their side or chest However, the virtual volumetric scene displayed in panel 712 is shown with the chest of patient 10 facing up. Accordingly, the real-time image feed as shown in panel 716 may not match the virtual volumetric scene displayed in panel 712. To assist the physician or other healthcare professional in navigating down the correct airway, the virtual volumetric scene may be registered to the real-time image feed, wherein the real-time image feed has been registered to steerable catheter 600.

In some embodiments, image correction is applied to the real-time image feed to assist in registering the virtual volumetric scene to the real-time image feed. To register the virtual volumetric scene as shown in panel 712 with the real-time image feed from bronchoscopic video camera 630 as shown in panel 716, the lens distortion of the real-time image feed must be corrected or the same lens distortion must be applied to the virtual volumetric scene.

After correcting the real-time image feed for lens distortion, virtual volumetric scene is registered to the real-time image feed. An initial registration may be performed in a region of the airway that is easily locatable with steerable catheter 600, such as the trachea for example. Thus the virtual volumetric scene as shown in panel 712 may be manually or automatically rotated to match one or more airway structure(s) (e.g., RMB and LMB) visible in both the virtual volumetric scene and the real-time image. In various embodiments, a matching algorithm may then be used to maintain registration of the virtual volumetric scene to the real-time image feed as steerable catheter 600 is navigated through the airway. Other registration methods known in the art may also be applied without departing from the scope of the invention. For example, the virtual volumetric scene may be registered to the real-time image feed using intensity based maximization of information mutual to the real-time image feed and the virtual volumetric scene instead of matching structures. In other embodiments, for example, surface normals of the real-time image feed may be calculated using a linear shape from shading algorithm based on the unique camera and/or lighting configurations of bronchoscopic video camera 630. The virtual volumetric scene may then be registered to the real-time image feed by matching the calculated surface normal with surface normal of the virtual volumetric scene. Accordingly, the registration of the virtual volumetric scene to the real-time image feed may cause both the real-time image feed and the virtual volumetric scene to be displayed on display 80 with "up" as "up."

In yet other embodiments, the registration of the virtual volumetric scene to the real-time image feed may be enhanced by registering the real-time image feed to localization element 610 of steerable catheter 600. By registering the real-time image feed to localization element 610, both the real-time image feed and/or the virtual volumetric scene may be shown in the "up" orientation on display 80 no matter what the position and orientation (POSE) of localization element 610 in steerable catheter 600 is as tracked by navigation system 70. The physician or other healthcare professional may always expect that an "up" steering input on steering actuator 614 will always result in the displayed real-time image moving "up." Thus, even if physician or other healthcare professional moves handle 612 of steerable catheter such that longitudinal axis 613 is not substantially vertical and thereby causes a rotation of distal end portion 606 of steerable catheter 600, because the real-time image feed is registered to steerable catheter 600 and to localization element 610, navigation system 70 may display real-time image feed and/or virtual volumetric scene with "up" as "up." Accordingly, the physician or other healthcare professional may still be able to easily determine how to manipulate steering actuator 614 of steerable catheter 600 to navigate steerable catheter 600 along navigation pathway 416 displayed in panel 712.

Figure 17A:
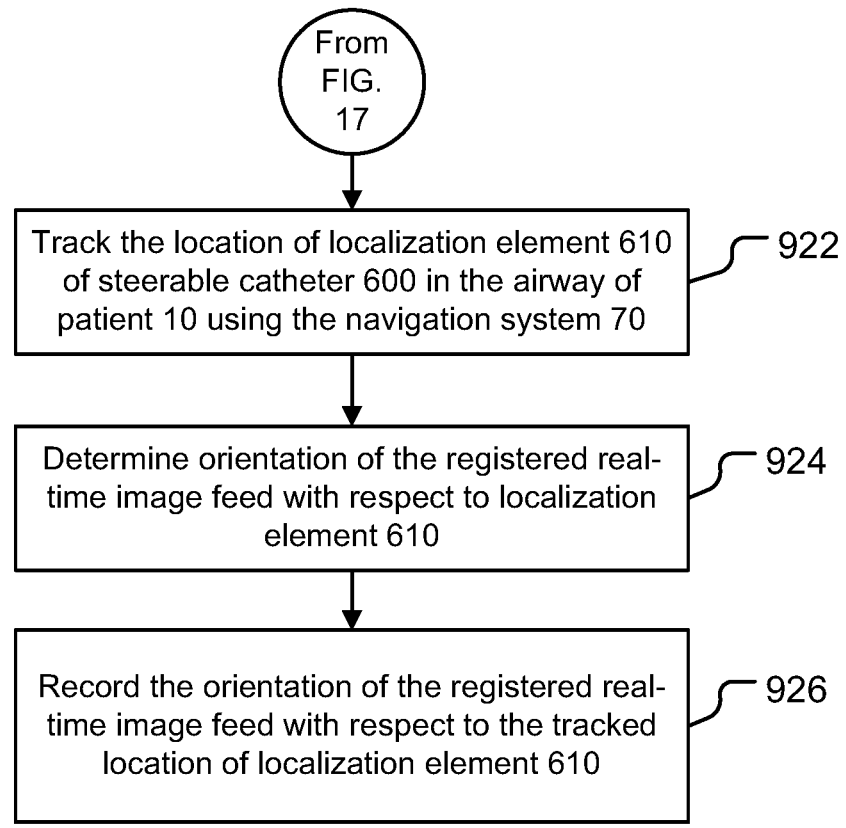
FIG. 17A is a flowchart illustrating additional steps of a method of registering the real-time image feed from a bronchoscopic video camera to a steerable catheter according to an embodiment of the invention.
Figure 18B:
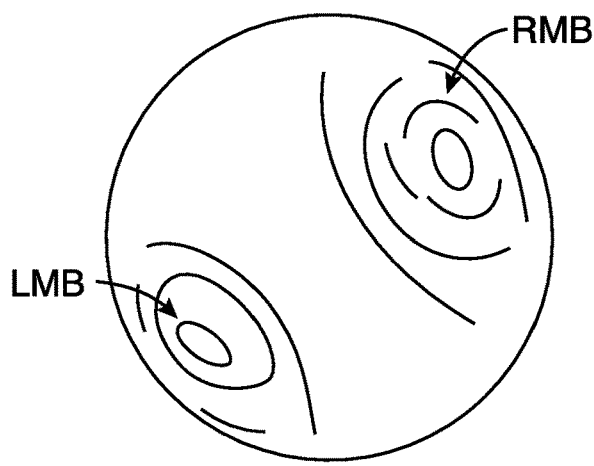
FIG. 18B is an image from a real-time image feed from a non-registered bronchoscopic video camera in a steerable catheter according to an embodiment of the present invention.
Figure 18C:
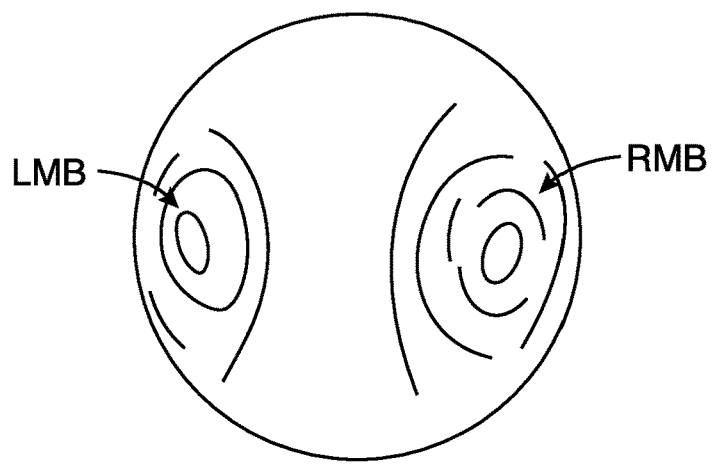
FIG. 18C is an image from a real-time image feed from a registered bronchoscopic video camera in a steerable catheter according to an embodiment of the present invention.
Figure 19:
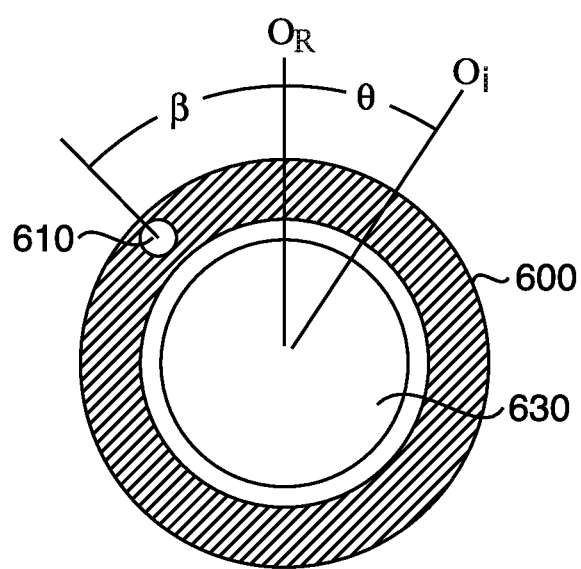
FIG. 19 is a section view of steerable catheter illustrating registering the real-time image feed from a bronchoscopic video camera to a steerable catheter and to a localization element of the steerable catheter according to an embodiment of the invention.

Referring now to FIG. 17A, a method of registering the real-time image feed from bronchoscopic video camera 630 to localization element 610 of steerable catheter 600 is described. Preferably, registration of the real-time image feed from bronchoscopic video camera 630 to localization element 610 of steerable catheter 600 is performed after the real-time image feed from bronchoscopic video camera 630 is registered to steerable catheter 600. At step 922, navigation system 70 tracks the location of localization element 610 of steerable catheter 600. At step 924, the orientation of the registered real-time image feed with respect to localization element 610 is determined. Referring now to FIG. 19, a section view of steerable catheter 600 is shown to aid in describing the registration of the real-time image feed from bronchoscopic video camera 630 to localization element 610 of steerable catheter 600. For purposes of simplicity not all structure of steerable catheter 600, localization element 610, and bronchoscopic video camera 630 are illustrated. As shown in FIG. 19, $O_i$ represents the un-registered orientation of the real-time image feed from bronchoscopic video camera 630. $O_R$ represents the orientation of the real-time image feed from bronchoscopic video camera 630 after the real-time image feed from bronchoscopic video camera 630 is registered to steerable catheter 600. Thus during registration of the real-time image feed from bronchoscopic video camera 630 to steerable catheter 600, the real-time image feed was rotated by angle Θ (see FIGS. 15, 17 steps 908, 920 respectively).

Thus, referring again to FIG. 17A, determining the orientation of the registered real-time image feed with respect to localization element 610 at step 924, comprises determining the angle β from $O_R$ to the tracked location of localization element 610. At step 926, the determined orientation (e.g., angle β) is recorded to navigation system 70. Accordingly, after the real-time image feed from bronchoscopic video camera 630 is registered to localization element 610 of steerable catheter 600, the real-time image feed and/or the virtual volumetric scene may be shown in the "up" orientation on display 80 regardless of the position and orientation (POSE) of localization element 610 in steerable catheter 600 as tracked by navigation system 70. Additionally, by registering the real-time image feed from bronchoscopic video camera 630 to localization element 610 of steerable catheter 600, the registration of the virtual volumetric scene may be maintained to the real-time image feed as steerable catheter 600 is navigated in the airway of patient 10.

In various embodiments as described above, registering the real-time image feed from a bronchoscopic video camera 630 to a steerable catheter 600 permits displaying one or more navigational aids over the real-time image feed from bronchoscopic video camera 630, wherein the navigational aids are registered to the real-time image feed. In certain embodiments, the navigational aids may be determined using the hybrid "Inspiration-Expiration" 3D airway model 414. For example, in certain embodiments, navigation system 70 may overlay navigation pathway 416 onto the real-time image feed from bronchoscopic video camera 630. In other embodiments, for example, navigation system may also overlay directional cues such as arrows or other indicators on the real-time image feed from bronchoscopic video camera 630. Integrating navigational aids, including but not limited to navigation pathway 416 and/or directional cues, with the real-time image feed may assist the physician or other healthcare professional in navigating steerable catheter 600 to the desired target tissue. Accordingly, in certain embodiments wherein navigational aids are overlaid onto real-time image feed, a virtual volumetric scene does not need to be displayed on display 80 of navigation system 70.

Although registering the real-time image feed from a bronchoscopic video camera 630 to a steerable catheter 600 has been described in detail herein, it will be understood that image feeds from other imaging devices 633 inserted into working channel 608 of steerable catheter 600 may be registered in similar manners. The imaging devices 633 may include, but are not limited to, endobronchial ultrasound (EBUS) device 634 (see FIG. 12B), an optical coherence tomography device (OCT), and probe based Confocal Laser Endomicroscopy (pCLE).

Returning to FIG. 14, navigation system 70 may also display a graphical representation 708 of the respiratory cycle of patient 10 monitored using PTD 20. In certain embodiments, one or more of the images and/or indicia displayed in panels 700, 702, 704, 706, 712 and 716 are displayed as a function of the monitored respiratory state. That is, images in image dataset 400 and/or generated from image dataset 400 are displayed on display 80 that depict the anatomy of patient 10 at the monitored respiratory state. For example, when the patient is at expiration as monitored by PTD 20, images of the anatomy of the patient depicting the anatomy at expiration are displayed. Accordingly, when the patient is at inspiration as monitored by PTD 20, images of the anatomy of patient 10 depicting the anatomy at inspiration are displayed. In other embodiments, one or more of the images displayed in panels 700, 702, 704, 706, 712 and 716 may not be displayed as a function of the monitored respiratory state. That is, images in image dataset 400 and/or generated from image dataset 400 are displayed on display 80 that depict the anatomy of patient 10 at one respiratory state. For example, when the patient is at expiration and inspiration as monitored by PTD 20, images of the anatomy of patient 10 depicting the anatomy at expiration are displayed. In embodiments where images are not displayed according to the monitored respiratory state, an indication 710 of whether the displayed images match the monitored respiratory state may be shown (e.g., "Respiration Matched", "Respiration out of Sync").

Additionally, the display of indicia of the locations of the target tissue and/or indicia of the location of various medical devices may be synchronized or gated with an anatomical function, such as the cardiac or respiratory cycle, of patient 10. That is, in certain embodiments, the indicia are displayed on display 80 as a function of the monitored respiratory state. In certain instances, the cardiac or respiratory cycle of patient 10 may cause the indicia to flutter or jitter within patient 10. In these instances, the indicia will likewise flutter or jitter on the image(s) displayed on display 80.

To eliminate the flutter of the indicia on the displayed image(s), the position and orientation (POSE) of localization elements 610, 660 is acquired at a repetitive point within each cycle of either the cardiac cycle or the respiratory cycle of patient 10. To synchronize the acquisition of position data for localization elements 610, 660, navigation system 70 may use a timing signal (e.g., respiratory phase signal) generated by PTD 20; however one skilled in the art will readily recognize other techniques for deriving a timing signal that correlate to at least one of the cardiac or respiratory cycle or other anatomical cycle of the patient.

As described above, the indicia indicate the location of steerable catheter 600 and percutaneous needle 650 based on the location of localization elements 610, 660 tracked by navigation system 70 as steerable catheter 600 and percutaneous needle 650 are navigated by the physician or other healthcare profession on and/or within patient 10. Rather than display the indicia on a real-time basis, the display of the indicia may be periodically updated based on the timing signal from PTD 20. In various embodiments, PTD 20 may be connected to navigation system 70. Navigation system 70 may then track localization elements 610, 660 in response to a timing signal received from PTD 20. The position of the indicia may then be updated on display 80. It is readily understood that other techniques for synchronizing the display of an indicia based on the timing signal are within the scope of the present invention, thereby eliminating any flutter or jitter which may appear on the displayed image(s). It is also envisioned that a path (or projected path) of steerable catheter 600, percutaneous needle 650, and/or other medical devices may also be illustrated on the displayed image(s).

Figure 20A:
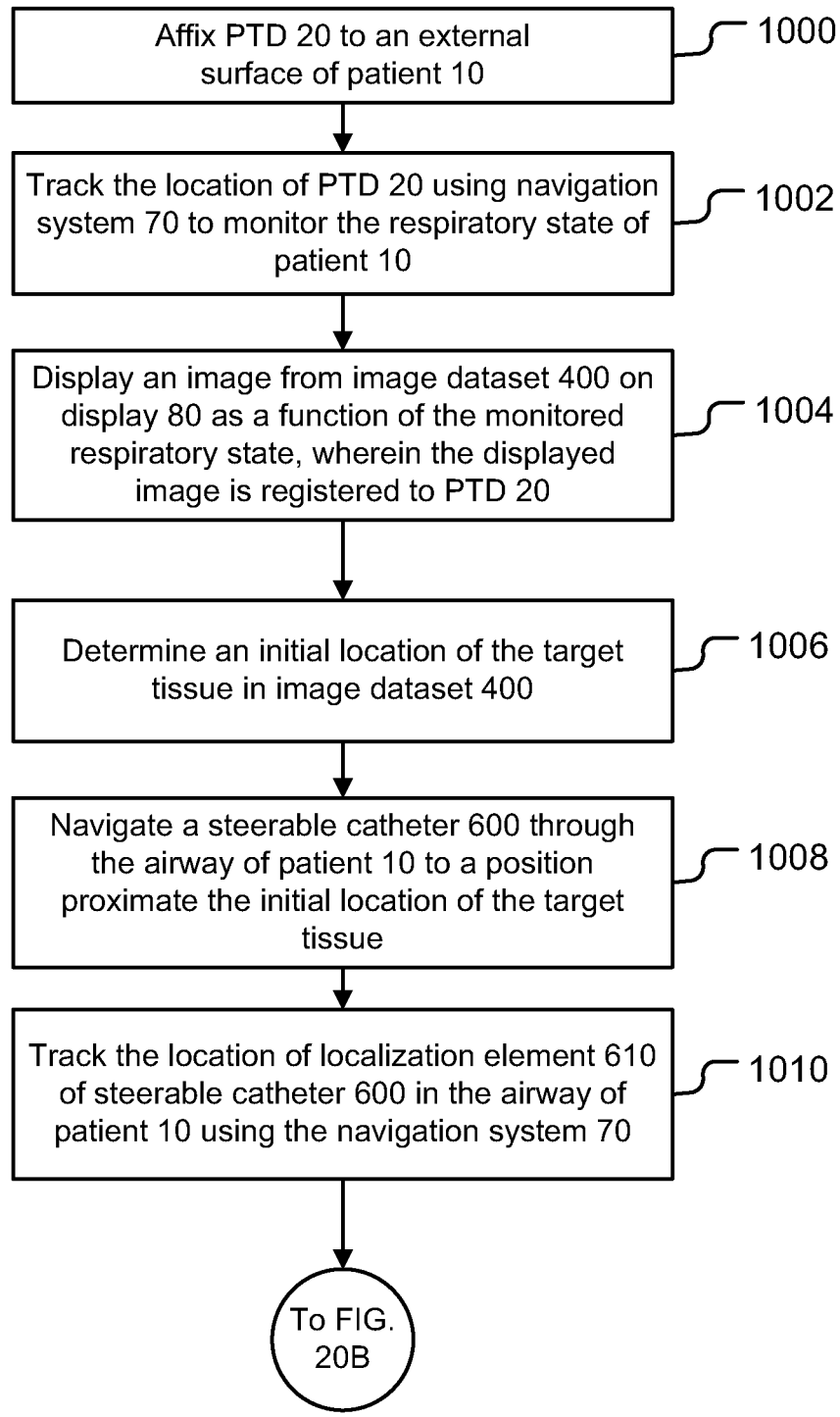
FIG. 20A is a flowchart illustrating a portion of a method of confirming the location of a target tissue according to an embodiment of the invention.
Figure 20B:
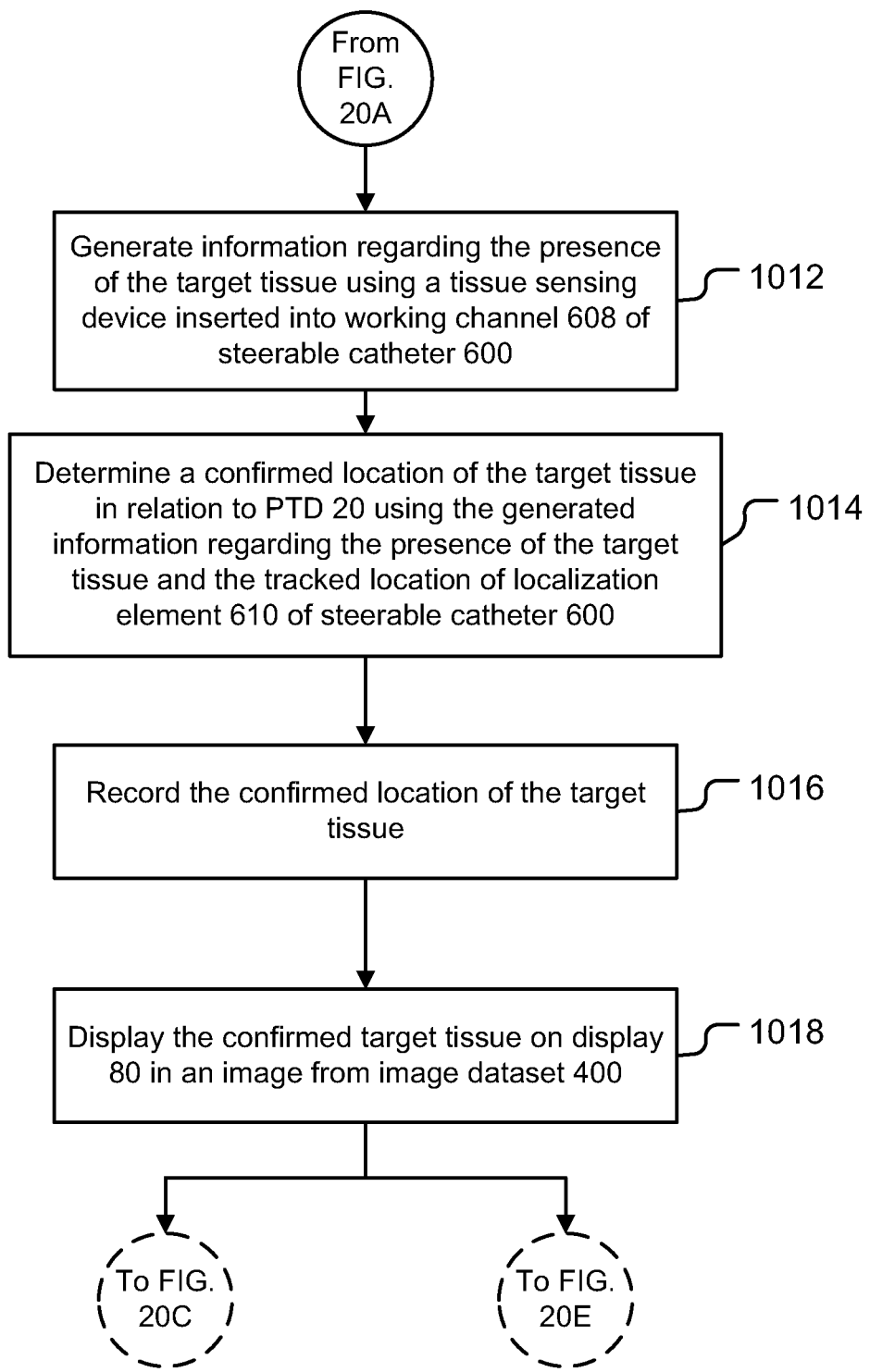
FIG. 20B is a flowchart illustrating a portion of a method of confirming the location of a target tissue according to an embodiment of the invention.

Utilizing the devices, systems, and/or methods described herein, a method of endobronchially confirming the location of a target in the lung of a patient and percutaneously intercepting the target at the confirmed location may be performed. In various embodiments, this method is performed during a second time interval after an image dataset 400 is generated during a first time interval. As illustrated in FIGS. 20A-20B, an embodiment of a method of endobronchially confirming the location of a target is illustrated. At step 1000, PTD 20 is affixed to the external surface of a patient 10. At step 1002, the respiratory state of patient 10 may be monitored by tracking the location of PTD 20 using navigation system 70. At step 1004, navigation system 70 displays an image from image dataset 400 on display 80 as a function of the monitored respiratory state. The displayed image is selected from one or more images in image dataset 400 and/or is generated by navigation system 70 using one or more images in image dataset 400. The displayed image is registered to PTD 20. At step 1006, an initial location of one or more target tissues in image dataset 400 is determined. This initial location of the target tissue is where it is believed that a target tissue is located within patient 10.

In certain embodiments, for example, the initial location of the target tissue(s) is determined after image dataset 400 is generated during the first time interval. In certain embodiments, for example, the initial location of the target tissue(s) may be selected at the start of and/or during the second time interval. The initial location of the target tissue(s) may be determined automatically using nodule detection or segmentation algorithms carried out by processor 52 of image analysis system 50 and/or processor 72 of navigation system 70. Additionally or alternatively, a physician or other healthcare professional manually identifies a target tissue on an image displayed on display 60 of image analysis system 50 and/or display 80 of navigation system 70. The physician or other healthcare professional may then determine the initial location of the target tissue(s) by selecting the target tissue depicted on display(s) 50, 80 using user interface device(s) 64, 84 (e.g., by clicking on displayed target tissue with a mouse) or some other point selection tool. In other embodiments, the initial location of the target tissue may be determined by the physician or other healthcare professional using nodule segmentation tools and/or using nodule density information. An indicia 720 of the initial target tissue location may then be displayed on display 80 as shown in FIG. 14.

Returning to FIG. 20A, at step 1008, a physician or other healthcare professional navigates steerable catheter 600 through the airway of patient 10 to a position proximate the initial location of the target tissue. Additionally, in certain embodiments, an imaging device 633 such as bronchoscopic video camera 630 (see FIG. 12A) is inserted into working channel 608, navigation system 70 displays on display 80 the real-time image feed of the inside of the airway of patient 10 generated by bronchoscopic video camera 630 as shown in panel 716 of FIG. 14. As described above the real-time image feed may be registered to steerable catheter 600. In certain embodiments, navigation system 70 may overlay navigation pathway 416 onto the real-time image feed from bronchoscopic video camera 630. In other embodiments, for example, navigation system may also overlay directional cues such as arrows or other indicators on the real-time image feed from bronchoscopic video camera 630. Integrating navigational aids, including but not limited to navigation pathway 416 and/or directional cues, with the real-time image feed may assist the physician or other healthcare professional in navigating steerable catheter 600 to the desired target tissue. Accordingly, in certain embodiments wherein navigational aids are overlaid onto real-time image feed, a virtual volumetric scene does not need to be displayed on display 80 of navigation system 70.

With reference again to FIG. 20A, as steerable catheter 600 is navigated through the airway of patient 10, at step 1010, navigation system 70 tracks the location of localization element 610 of steerable catheter 60. As described above, an indicia of 718 of the location of steerable catheter 600 may also be displayed on display 80 as shown in panels 700, 702, 704, and 706 of FIG. 14.

Figure 21:
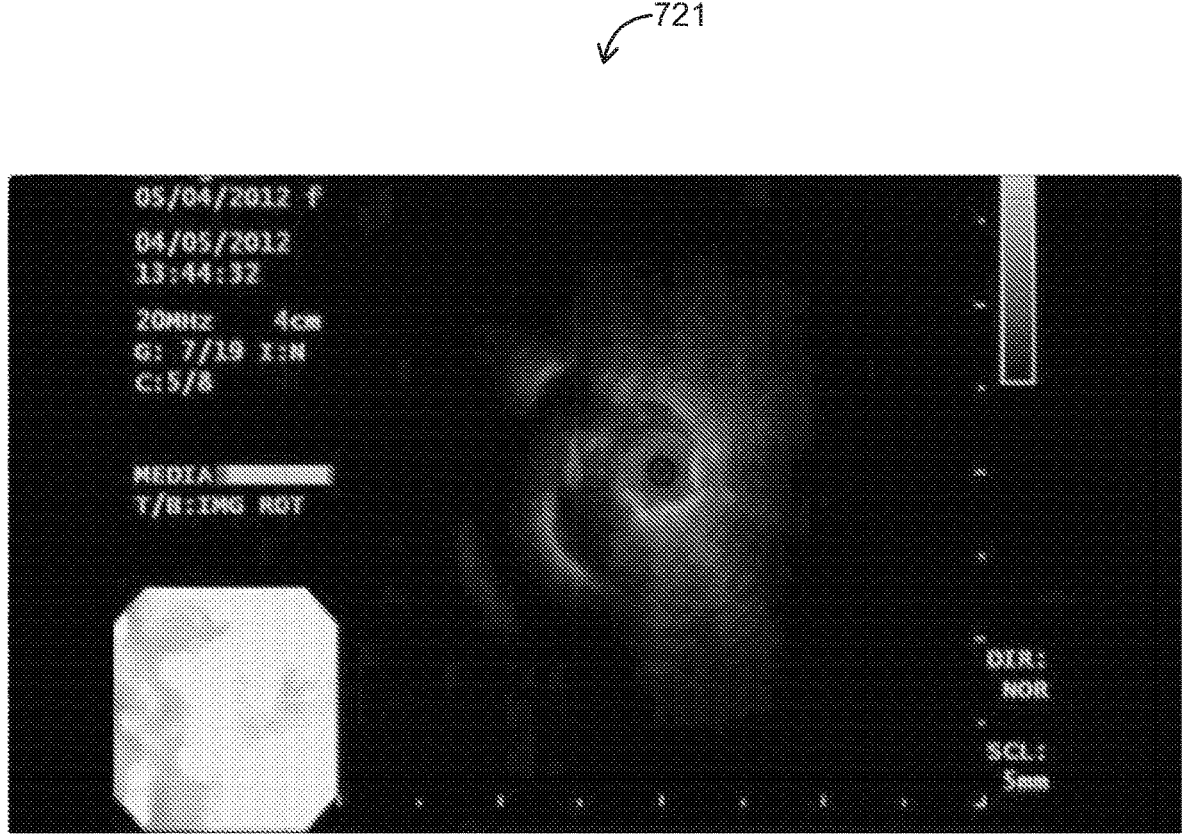
FIG. 21 is an image from an endobronchial ultrasound device according to an embodiment of the invention.

Referring now to FIG. 20B, the method continues at step 1012, where information regarding the presence of the target tissue is generated using tissue sensing device 632 inserted into working channel 608 of steerable catheter 600. In certain embodiments, tissue sensing device 632 may be imaging device 633 inserted into the airway of patient 10, such as, for example, endobronchial ultrasound (EBUS) device 634 (see FIG. 12B), an optical coherence tomography device (OCT), and/or probe based Confocal Laser Endomicroscopy (pCLE). Imaging device 633 may be extended out tip 607 of steerable catheter 600 and may generate a population of images of the target tissue. Where imaging device 637 is EBUS device 634, EBUS device 634 may be a radial EBUS device or a linear EBUS device. Illustrated in FIG. 21 is an exemplary image 721 of the target tissue generated by a radial EBUS device which may be displayed on display 80. In other embodiments, tissue sensing device 632 may include, but is not limited to, a cell analysis device, a cancer detecting device, an exhaled breath condensate analyzer, a physiological characteristic sensor, a chemical analysis device, an aromatic hydrocarbon detection device, etc.

Returning to FIG. 20B, a confirmed location of the target is using the generated information regarding the presence of the target tissue and the tracked location of localization element 610 of steerable catheter 600. For example, if tissue sensing device 632 is an imaging device 633 which generates a population of images of the target tissue, navigation system 70 tracks the extension (x), if any, of imaging device 633 in relation to localization element 610. By tracking the extension (x) in relation to localization element 610 and the position and orientation (POSE) of localization element 610, navigation system 70 knows the coordinates at which the population of images of the target tissue are generated and may thus determine the actual location and size of the target tissue within patient 10. In certain embodiments, the confirmed location of the target tissue is determined in relation to the location of PTD 20. In other embodiments, for example, the confirmed location of the target tissue is determined in relation to the location of electromagnetic (EM) field generator 82 of navigation system 70.

At step 1016, after the confirmed location of the target tissue is determined, the confirmed location of the target tissue is recorded. In one embodiment, for example, recording the confirmed location of the target tissue comprises recording a three-dimensional (3D) location of the confirmed target tissue in relation to PTD 20. In another embodiment, for example, recording the confirmed location of the target tissue comprises recording a three-dimensional (3D) location of the confirmed target tissue in relation to electromagnetic (EM) field generator 82 of navigation system 70. In one embodiment, for example, recording the confirmed location of the target tissue comprises recording four-dimensional data (4D) comprising a three-dimensional (3D) location of the confirmed target tissue in relation to PTD 20 and the respiratory state of patient 10 at the time the location of the target tissue was confirmed. In another embodiment, for example, recording the confirmed location of the target tissue comprises recording four-dimensional data (4D) comprising a three-dimensional (3D) location of the confirmed target tissue in relation to electromagnetic (EM) field generator 82 of navigation system 70 and the respiratory state of patient 10 at the time the location of the target tissue was confirmed. In yet another embodiment, for example, recording the confirmed location of the target tissue comprises recording four-dimensional (4D) data comprising a three-dimensional location (3D) of the confirmed target tissue in relation to PTD 20 and a cardiac state of the patient at the time the location of the target tissue was confirmed. In yet another embodiment, for example, recording the confirmed location of the target tissue comprises recording four-dimensional (4D) data comprising a three-dimensional location (3D) of the confirmed target tissue in relation to electromagnetic (EM) field generator 82 and a cardiac state of the patient at the time the location of the target tissue was confirmed. In various embodiments, this confirmed location of the target tissue may then be applied to one or more images from image dataset 400 depicting the airway at the respiratory state of patient 10 at the time the location of the target tissue was confirmed. This information is recorded in memory component 74 of navigation system 70.

Figure 22:
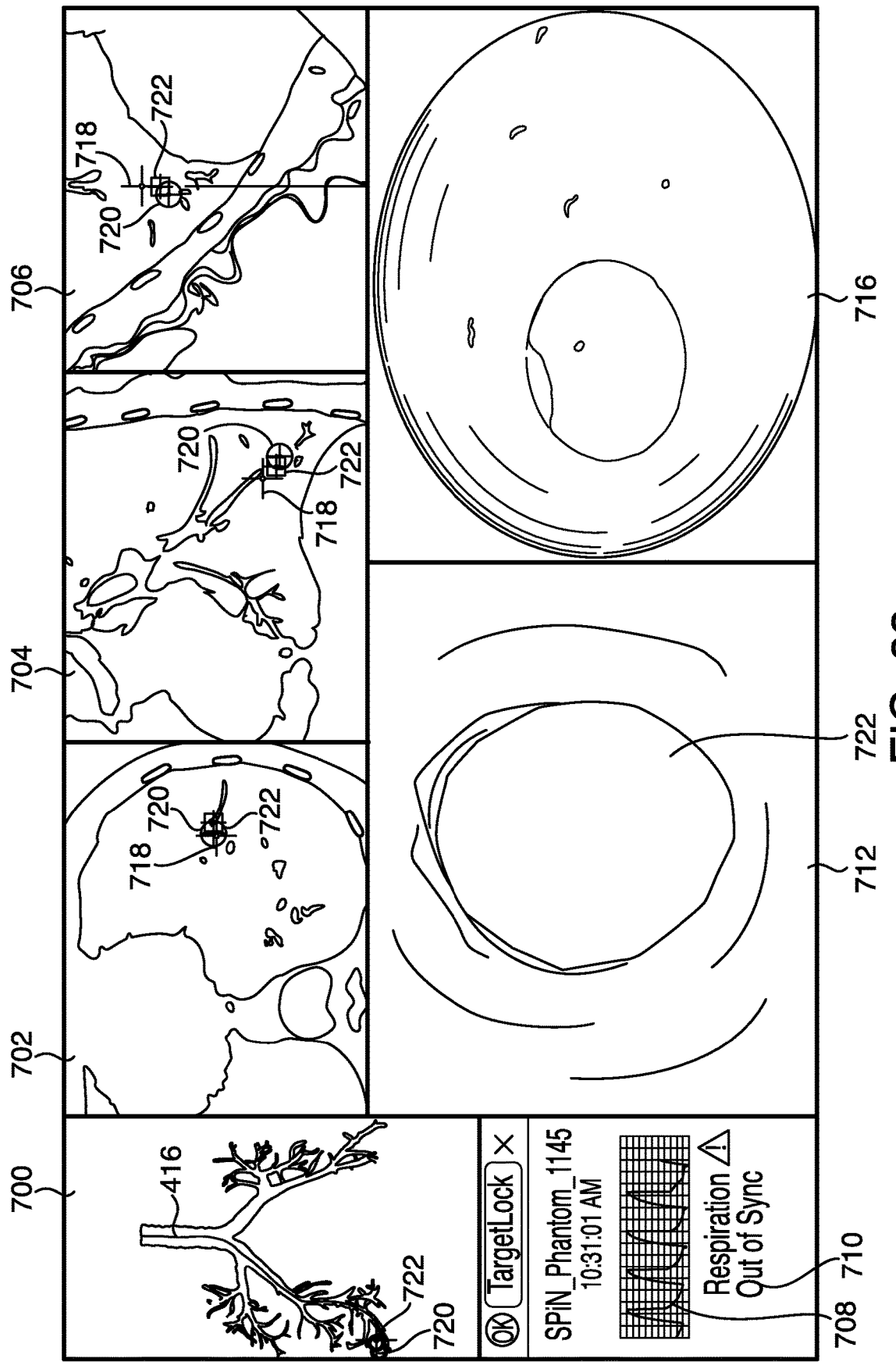
FIG. 22 illustrates a population of images which may be displayed on a display of a navigation system according to an embodiment of the invention.
Figure 22A:
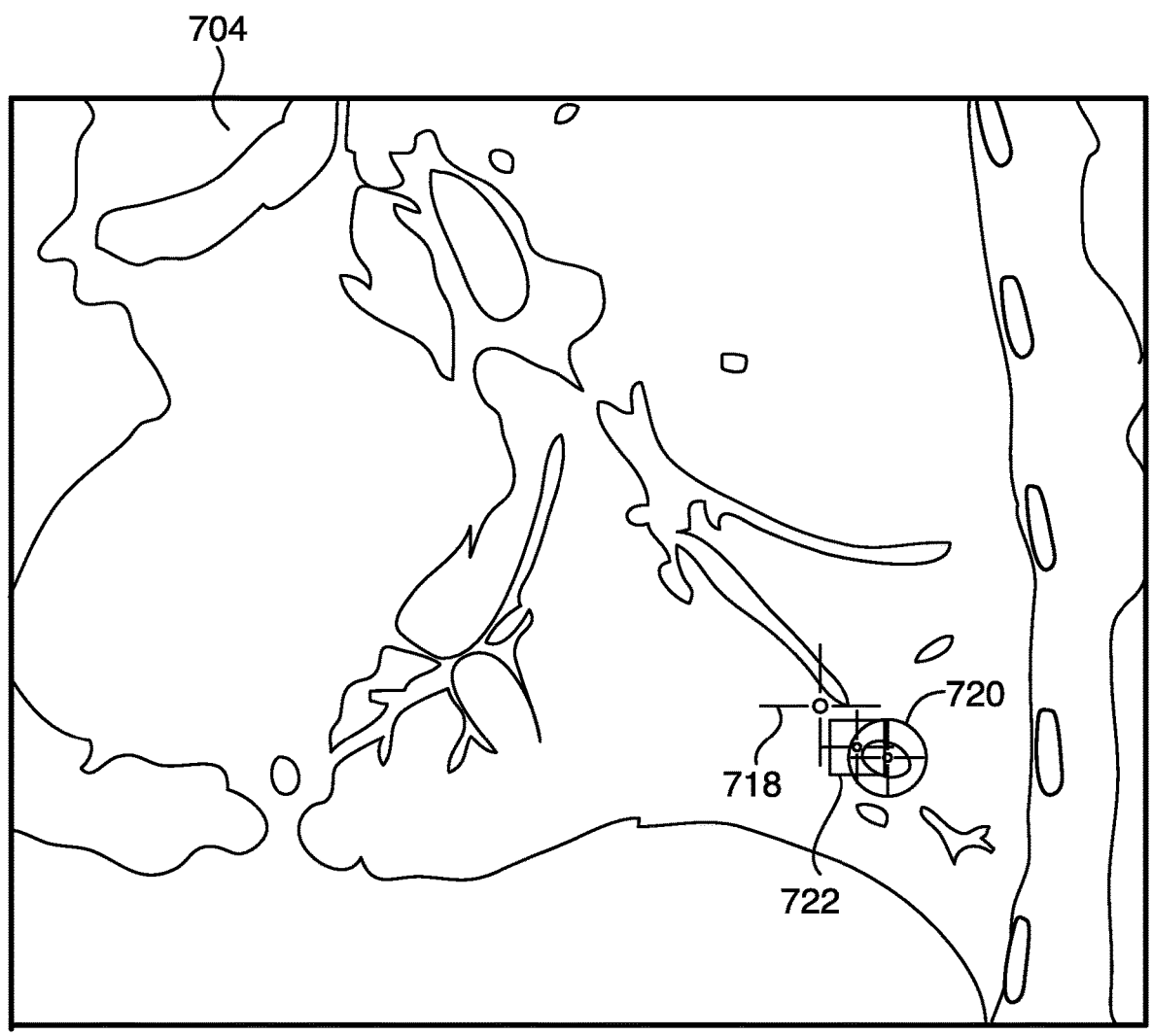
FIG. 22A illustrates an enlarged view of an image which may be displayed on a display of a navigation system according to an embodiment of the invention.

At step 1018, the confirmed location of the target tissue is displayed on display 80 of navigation system 70 in one or more images from image dataset 400. In certain embodiments, the displayed image(s) depict the airway of the patient at the respiratory state of patient 10 at the time the location of the target tissue was confirmed. As shown in FIG. 22, navigation system 70 may display an indicia 722 (shown as crosshair bounded by a square) of the confirmed location of the target tissue in a variety of images, including but not limited to, hybrid "Inspiration-Expiration" 3D airway model 414 in panel 700, axial, coronal and oblique images in panels 702, 704 (shown enlarged in FIG. 22A), and 706, respectively, and virtual volumetric scene in panel 712. Navigation system 70 may be able to display an indicia 720 (shown as circle in crosshair bounded by a circle) of the initial location of the target tissue, an indicia 722 of the confirmed location of the target tissue, and an indicia 718 (shown as crosshair) of steerable catheter 600. The method may optionally continue according to steps illustrated in FIGS. 20C and 20E as described more fully elsewhere herein.

After the confirmed location of the target tissue is recorded, the physician or other healthcare professional can return to the confirmed location of the target tissue using a medical device, such as steerable catheter 600 or percutaneous needle 650, without needing to re-register the patient. Accordingly, because, in certain embodiments, the confirmed location of the target tissue is recorded in relation to the location of patient tracking device 20, the physician or other healthcare professional can navigate medical device to the confirmed location of the target tissue knowing the location of patient tracking device 20. For example, in certain embodiments, the physician or other healthcare professional navigates to the confirmed location of the target tissue wherein navigation system 70 displays on display 80 only an indicia 722 of the confirmed location of the target tissue, an indicia 718 of steerable catheter 600, and/or an indicia 734 of percutaneous needle 650 (see FIG. 23). Using one or more of indicia 722, 718, 734, physician or other healthcare professional navigates medical device to the confirmed location of the target tissue without needing navigation system 70 to display hybrid "Inspiration-Expiration" 3D airway model 414, one or more images from image dataset 400, navigation pathway 416, and/or real time image feed from bronchoscopic video camera 630.

Additionally, because, in certain embodiments, the confirmed location of the target tissue is recorded in relation to the location of electromagnetic (EM) field generator 82, the physician or other healthcare professional can navigate medical device to the confirmed location of the target tissue if patient 10 has not moved relative to localization device 76. For example, in certain embodiments, the physician or other healthcare professional navigates to the confirmed location of the target tissue wherein navigation system 70 displays on display 80 an indicia 722 of the confirmed location of the target tissue, an indicia 718 of steerable catheter 600, and/or an indicia 734 of percutaneous needle 650. Using one or more of indicia 722, 718, 734, physician or other healthcare professional navigates medical device to the confirmed location of the target tissue without needing navigation system 70 to display hybrid "Inspiration-Expiration" 3D airway model, one or more images from image dataset 400, navigation pathway 416, and/or real time image feed from bronchoscopic video camera 630.

Due to a variety of factors including, but not limited to, registration errors, shifting of patient location, changes in patient anatomy, the initial target location determined at step 1006 may not match the actual confirmed location of the target determined in step 1014. Accordingly, without performing this confirmation step, a biopsy or medical therapy delivered to the initial target location may only partially intercept the actual target tissue or may be performed at an incorrect location such as healthy tissue. Insufficient and/or incorrect sampling or treatment of the target tissue and/or healthy tissue may lead to misdiagnoses and/or reduced treatment efficacy. Thus, by confirming the actual location of the target tissue in relation to PTD 20 and/or electromagnetic (EM) field generator 82, intercepting (e.g., sampling, treating) the target tissue may be more accurately carried out in a variety of ways. Consequently, a physician or other healthcare professional may have a higher confidence that they are intercepting the target tissue. In certain embodiments, for example, the target tissue may be sampled using a variety of medical devices including, but not limited to, forceps devices, needles, brushes, etc. Treatment may also be endobronchially delivered to the confirmed location of the target tissue using a variety of medical devices including, but not limited to, ablation probes, radioactive seeds, implants, energy delivery devices, therapy delivery devices, delivery of energy activated substances (e.g., porfimer sodium) and energy devices, radiofrequency (RF) energy devices, cryotherapy devices, laser devices, microwave devices, diffuse infrared laser devices, fluids, drugs, combinations thereof, or the like.

In certain embodiments, the target tissue may not be reachable using endobronchial methods, accordingly, after the location of the target tissue is endobronchially confirmed, the target tissue may be percutaneously intercepted. The percutaneous interception may be carried out using a percutaneous device. Percutaneous device may preferably be percutaneous needle 650 described above. Because percutaneous needle 650 includes localization element 660, the position and orientation (POSE) of tip 657 is tracked by navigation system 70. Accordingly, navigation system 70 calculates and displays a trajectory of percutaneous needle 650 based on where percutaneous needle 650 is located and oriented by physician or other healthcare professional. However, in various embodiments, for example, percutaneous device may include, but is not limited to percutaneous needle 650, a thoracic wedge resection device, a biopsy gun, a tracked core biopsy device, and/or any other medical device which may be used to percutaneously intercept a target tissue. The percutaneous devices preferably include a localization element so that the position and orientation (POSE) of the percutaneous devices may be tracked by navigation system 70.

Figure 20C:
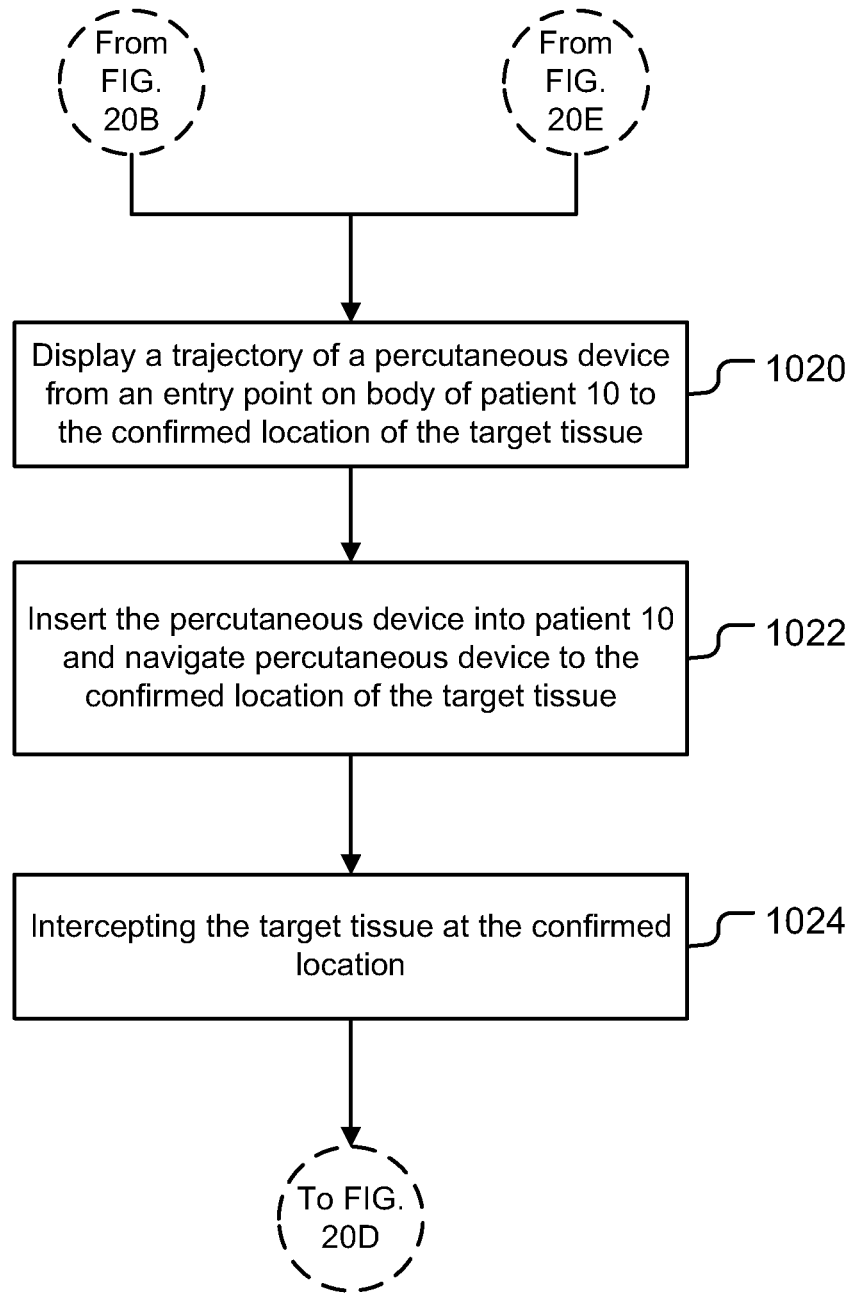
FIG. 20C is a flowchart illustrating a portion of a method of confirming the location of a target tissue according to an embodiment of the invention.

Referring now to FIG. 20C, at step 1020, navigation system 70 displays on display 80 one or more trajectories from an entry point on the surface of patient 10 to the confirmed location of the target tissue. In certain embodiments, a displayed trajectory may be a suggested trajectory calculated by navigation system 70 wherein the suggested trajectory is the shortest distance from the confirmed location of the target tissue to the external surface of patient 10. Navigation system 70 may utilize procedural position of patient 10 such as supine, prone, or laying on the left or right side to calculate the suggested trajectory. Accordingly, navigation system 70 may display a suggested trajectory that does not require altering the procedural position of patient 10. For example, if the trajectory having the shortest distance from the confirmed location of the target tissue to the external surface of patient 10 requires entry through the back of patient 10, but patient 10 is supine, an alternative suggested trajectory may be calculated and displayed which permits entry through the chest or side of patient 10.

In certain embodiments, the suggested trajectory may be calculated that extends through the longest axis or longest diameter of the target tissue to ensure that the amount of target tissue sampled and/or treated is increased and/or maximized. Additionally, the patient 10 specific segmented target tissue may also have characteristics such as high density or spiculations that identify preferred regions to sample and/or treat. For example, in certain embodiments, the suggested trajectory may be calculated to extend through spiculations of the target tissue. In other embodiments, for example, a change in size of the target tissue may be seen between inspiration and expiration scans. In certain situations, this apparent change in size may be the result of infected tissue near the target tissue changing in size from inspiration to expiration. Typically, however, the target tissue will not change in size from inspiration to expiration, accordingly image analysis system 50 and/or navigation system 70 may be able to identify the target tissue based on a minimal or no change in density, size, location, and shape from inspiration to expiration. The suggested trajectory may thus be calculated to extend through such portions of the target tissue.

Additionally or alternatively, in certain embodiments, a displayed trajectory may be an actual trajectory calculated by navigation system 70 wherein the actual trajectory is the based on where percutaneous needle 650 is located and oriented by physician or other healthcare professional. Accordingly, in certain embodiments, navigation system 70 may be able to display on display 80 both a suggested trajectory and an actual trajectory of percutaneous needle 650. Thus, a physician or other healthcare professional may move tip 657 of percutaneous needle 650 along the body of patient 10 and may orient percutaneous needle 650 so that the suggested trajectory and the actual trajectory displayed by navigation system 70 on display 80 are in alignment. Once the actual trajectory and the suggested trajectory are in alignment, the physician or other healthcare professional inserts percutaneous needle 650 into patient along the actual trajectory. In other embodiments, for example, no suggested trajectory may be displayed.

Figure 23:
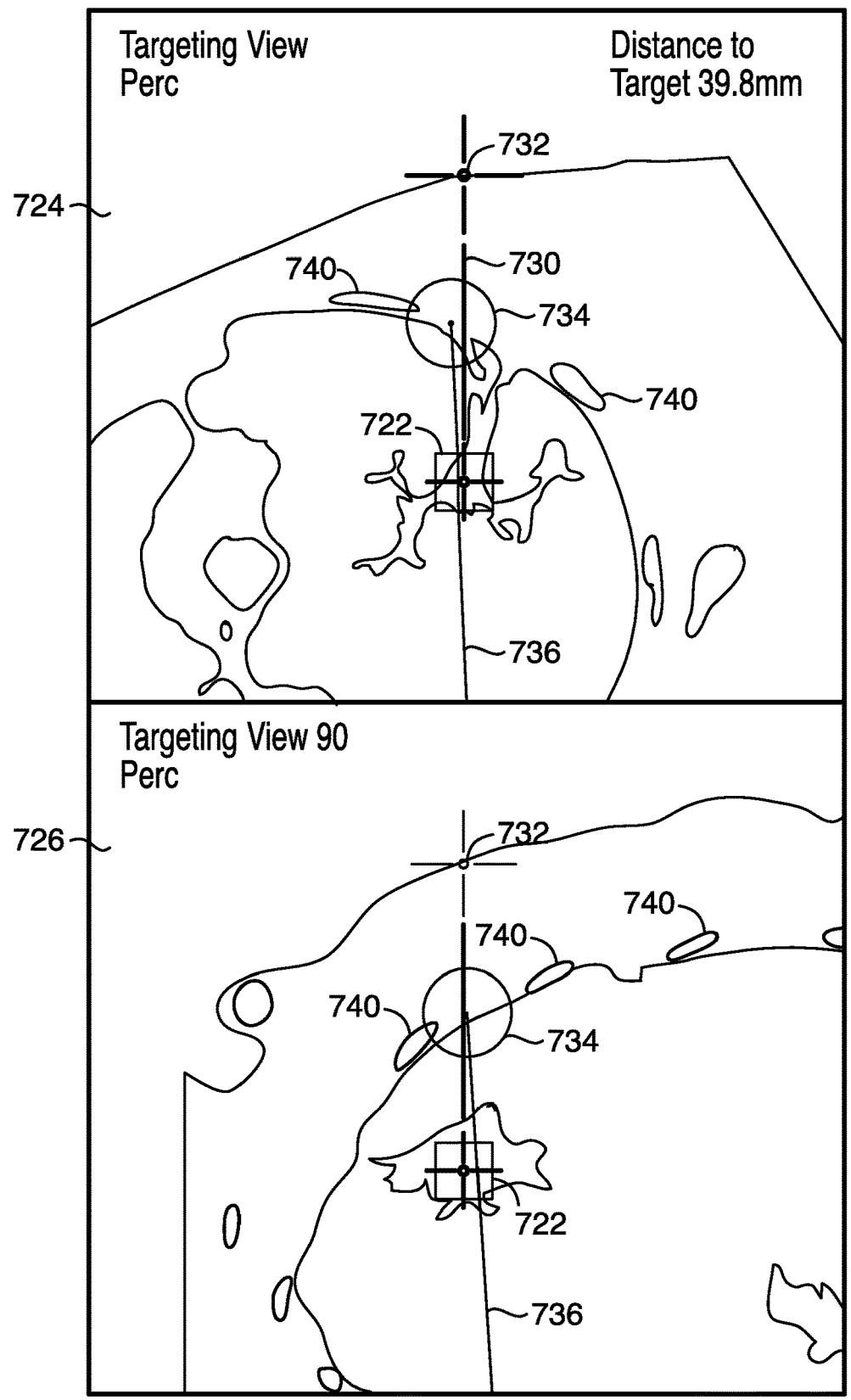
FIG. 23 illustrates a population of images which may be displayed on a display of a navigation system according to an embodiment of the invention.

FIG. 23 illustrates one embodiment where navigation system 70 displays on display 80 suggested and actual trajectories from an entry point on the surface of patient 10 to the confirmed location of the target tissue. Panels 724 and 726 illustrate views that navigation system 70 may display. The displayed images may be selected from one or more images in image dataset 400 or may be generated by navigation system 70 using one or more images in image dataset 400. Additionally, indicia 722 (shown as crosshair bounded by a square) of the confirmed location of the target tissue and suggested trajectory 730 from entry point 732 to the confirmed location of the target tissue are displayed on display 80. Furthermore, an indicia 734 of the location of percutaneous needle 650 is displayed. In certain embodiments, for example, indicia 734 indicates the location of distal end portion 656 of percutaneous needle 650. In other embodiments, for example, indicia 734 indicates the location of localization element 660 of percutaneous needle 650. In yet other embodiments, for example, indicia 734 indicates the location of tip 657 of percutaneous needle 650. An actual trajectory 736 of percutaneous needle 650 is also displayed on display 80 by navigation system 70 as shown in panels 724, 726. As described more fully elsewhere herein, suggested trajectory 730 may avoid anatomical structures 740 such as, for example, bone, the heart, the liver, other organs, fissures, diseased tissue, such as chronic obstructive pulmonary disease (COPD) lung tissue, and blood vessels. Furthermore, as shown in panel 724, navigation system 70 may be able to display a distance from tip 657 of percutaneous needle 650 to the confirmed location of the target tissue.

Referring again to FIG. 20C, at step 1022, the physician or other healthcare professional inserts percutaneous needle 650 into the patient and navigates tip 657 proximate to the confirmed location of the target tissue. Then at step 1024, the target tissue at the confirmed location is intercepted. In certain embodiments, for example, intercepting the target tissue at the confirmed location includes inserting a biopsy device into working channel 658 of percutaneous needle 650 and extending the biopsy device beyond tip 657 to sample the target tissue. In other embodiments, for example, intercepting the target tissue at the confirmed location includes inserting a therapy device into working channel 658 of percutaneous needle 650 and delivering therapy to the target tissue. In various embodiments, therapy device may be an ablation probe and navigation system 70 may be able to display on display 80 ablation models at the confirmed location of the target tissue. The ablation models may assist the physician or other healthcare professional in delivering the appropriate amount of treatment to the target tissue. The method may optionally continue according to steps illustrated in FIG. 20D as described more fully elsewhere herein.

In various embodiments, the method as described in FIGS. 20A-20C may further include the step of taking a population of images of at least a portion of percutaneous needle 650 at the confirmed location of the target tissue using imaging device 633 disposed in the airway of the patient. For example, as described above, imaging device 633 may be EBUS device 634 extended out tip 607 of steerable catheter 600. The images may be used to confirm that tip 657 of percutaneous needle 650 was actually navigated to proximate the confirmed location of the target tissue. The image(s) of percutaneous needle 650 at the confirmed location of the target tissue may be recorded into a patient file as proof that the confirmed location of the target was reached. Additionally, imaging device 633 may be used to generate a population of images of the biopsy device sampling the target tissue and/or a population of images of the therapy device delivering therapy to the target tissue. The image(s) of biopsy device and therapy device sampling or delivering therapy to the target tissue may be recorded into a patient file as proof that the target tissue was sampled and/or treated.

Additional to or alternative to using imaging device 633 to evaluate whether percutaneous needle 650 has been navigated to proximate the confirmed location of the target tissue, a sensing device may be used to sense the presence of at least a portion of percutaneous needle 650 at the confirmed location of the target tissue. For example, the sensing device may include, but is not limited to, a heat sensor, magnetic sensor, electrical sensor, that may be extended out tip 607 of steerable catheter 600. In certain embodiments, the sensing device may also be able to sense the presence of the biopsy device sampling the target tissue and/or the therapy device delivering therapy to the target tissue. For example, a heat sensor extended out tip 607 of steerable catheter 600 may be used to determine when the target tissue has been sufficiently treated. Additionally, navigating steerable catheter 600 down multiple airways adjacent to a target tissue and extending a heat sensor out tip 607 of steerable catheter 600 in each of the adjacent airways may be used to determine when a target tissue that is located between the adjacent airways has been treated. In certain embodiments, heat sensors may be placed in multiple airways adjacent to a target tissue using steerable catheter 600 and the multiple heat sensors may be used to determine when a target tissue that is located between the adjacent airways has been treated.

Figure 20D:
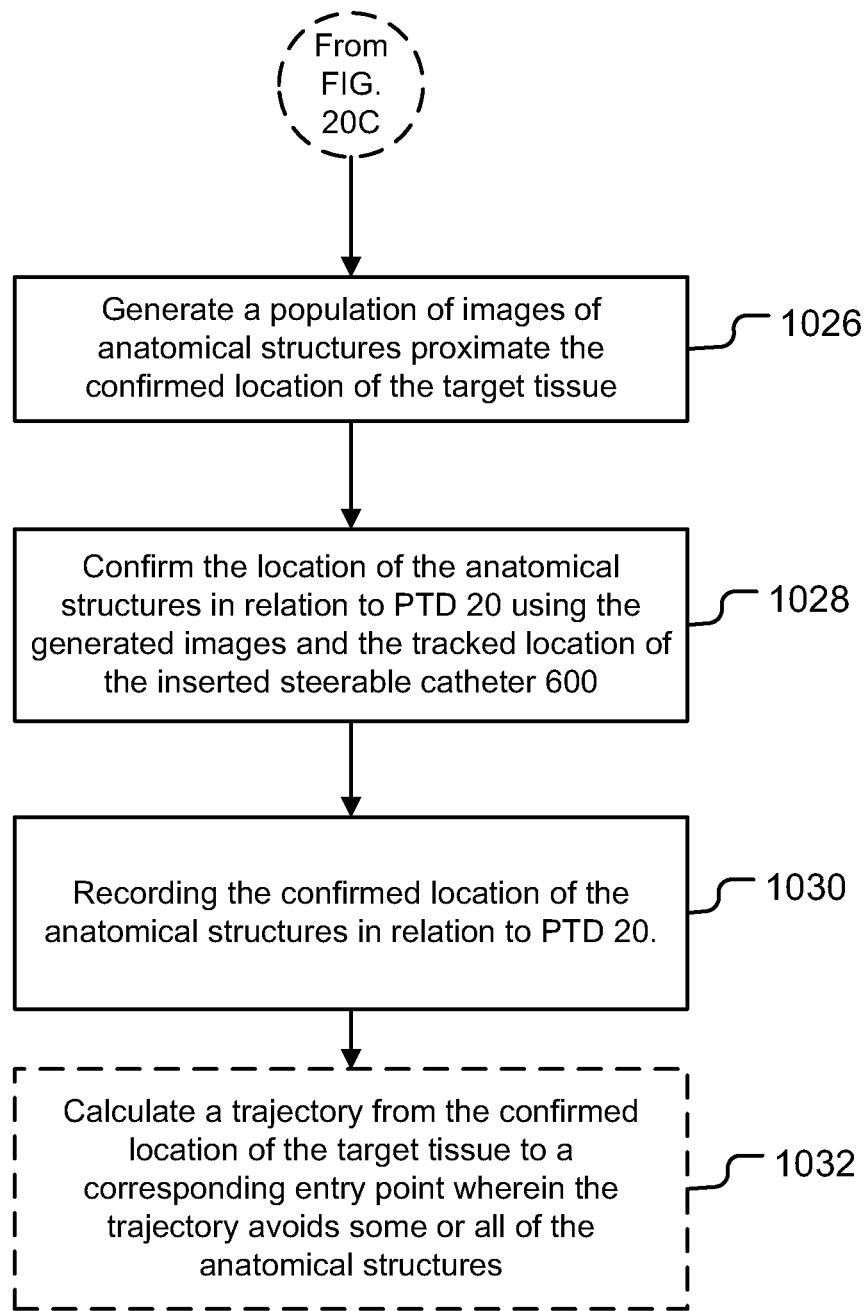
FIG. 20D is a flowchart illustrating a portion of a method of confirming the location of a target tissue according to an embodiment of the invention.

In various embodiments, the method as described in FIGS. 20A-20C may further include the steps outlined in FIG. 20D. At step 1026, using imaging device 633 disposed in the airway of patient 10, a population of images are generated of one or more anatomical structures proximate the confirmed location of the target tissue. Anatomical structures may include, but are not limited to, bone, the heart, the liver, other organs, fissures, diseased tissue, such as, for example chronic obstructive pulmonary disease (COPD) lung tissue, and blood vessels. Accordingly, the anatomical structures may be any structure within the body of patient 10 that should be avoided, if possible, by percutaneous needle 650. The imaging device, for example, may be EBUS device 634 extended out tip 607 of steerable catheter 600. At step 1028, a confirmed location of the anatomical structure(s) is determined in relation to the location of PTD 20 using the population of images and the tracked location of localization element 610 of steerable catheter 600. For example, navigation system 70 tracks the extension (x), if any, of EBUS device 634 in relation to localization element 610. By tracking the extension (x) in relation to localization element 610, navigation system 70 knows the coordinates at which the population of images of the anatomical structure(s) are generated and may thus determine the actual location and size of the anatomical structure(s) within patient 10 with respect to PTD 20.

At step 1030, after the location of the anatomical structure(s) is determined, the confirmed location of the anatomical structure(s) is recorded. In one embodiment, for example, recording the confirmed location of the anatomical structure(s) comprises recording a three-dimensional (3D) location of the confirmed anatomical structure(s) in relation to PTD 20. In another embodiment, for example, recording the confirmed location of the anatomical structure(s) comprises recording a three-dimensional (3D) location of the confirmed anatomical structure(s) in relation to electromagnetic (EM) field generator 82 of navigation system 70. In one embodiment, for example, recording the confirmed location of the anatomical structure(s) comprises recording four-dimensional data (4D) comprising a three-dimensional (3D) location of the confirmed anatomical structure(s) in relation to PTD 20 and the respiratory state of patient 10 at the time the location of the anatomical structure(s) was confirmed. In another embodiment, for example, recording the confirmed location of the anatomical structure(s) com- prises recording four-dimensional data (4D) comprising a three-dimensional (3D) location of the confirmed anatomical structure(s) in relation to electromagnetic (EM) field generator 82 of navigation system 70 and the respiratory state of patient 10 at the time the location of the anatomical structure(s) was confirmed. In yet another embodiment, for example, recording the confirmed location of the anatomical structure(s) comprises recording four-dimensional (4D) data comprising a three-dimensional location (3D) of the confirmed anatomical structure(s) in relation to PTD 20 and a cardiac state of the patient at the time the location of the anatomical structure(s) was confirmed. In yet another embodiment, for example, recording the confirmed location of the anatomical structure(s) comprises recording four-dimensional (4D) data comprising a three-dimensional location (3D) of the confirmed anatomical structure(s) in relation to electromagnetic (EM) field generator 82 and a cardiac state of the patient at the time the location of the anatomical structure(s) was confirmed. In various embodiments, this confirmed location of the anatomical structure(s) may then be applied to one or more images from image dataset 400 depicting the airway at the respiratory state of patient 10 at the time the location of the anatomical structure(s) was confirmed. This information is recorded in memory component 74 of navigation system 70.

Optionally, at step 1032, navigation system 70 calculates and displays a trajectory of a percutaneous device (e.g., percutaneous needle 650) from the confirmed location of the target tissue to a corresponding entry point on the body of patient 10. This trajectory may avoid some or all of the anatomical structures. Accordingly, if a physician or other healthcare professional inserts percutaneous device, such as percutaneous needle 650, following this trajectory, the percutaneous device may avoid some or all of the anatomical structures thereby preventing damage to the anatomical structure(s).

In various embodiments, in addition to calculating and/or displaying any of the trajectories described herein, navigation system 70 displays an extended trajectory of a medical device that may be inserted into working channel 658 of percutaneous needle 650 and extended past tip 657. In certain embodiments, for example, the medical device may include, but is not limited to, an aspiration needle, a forceps device, a brush, or any type of biopsy device. In other embodiments, for example, the medical device may include, but is not limited to, an ablation probe, a radioactive seed placement device, a fiducial placement device, and/or any type of therapy device. The extended trajectory displays the potential extension of the medical device so that it may be confirmed that potential extension of the medical device will sample and/or treat the target tissue and will not hit one or more anatomical structures. The displayed extended trajectory may also aid in ensuring that a sufficient sample is taken and/or that the treatment may be properly placed in the target tissue.

Figure 20E:
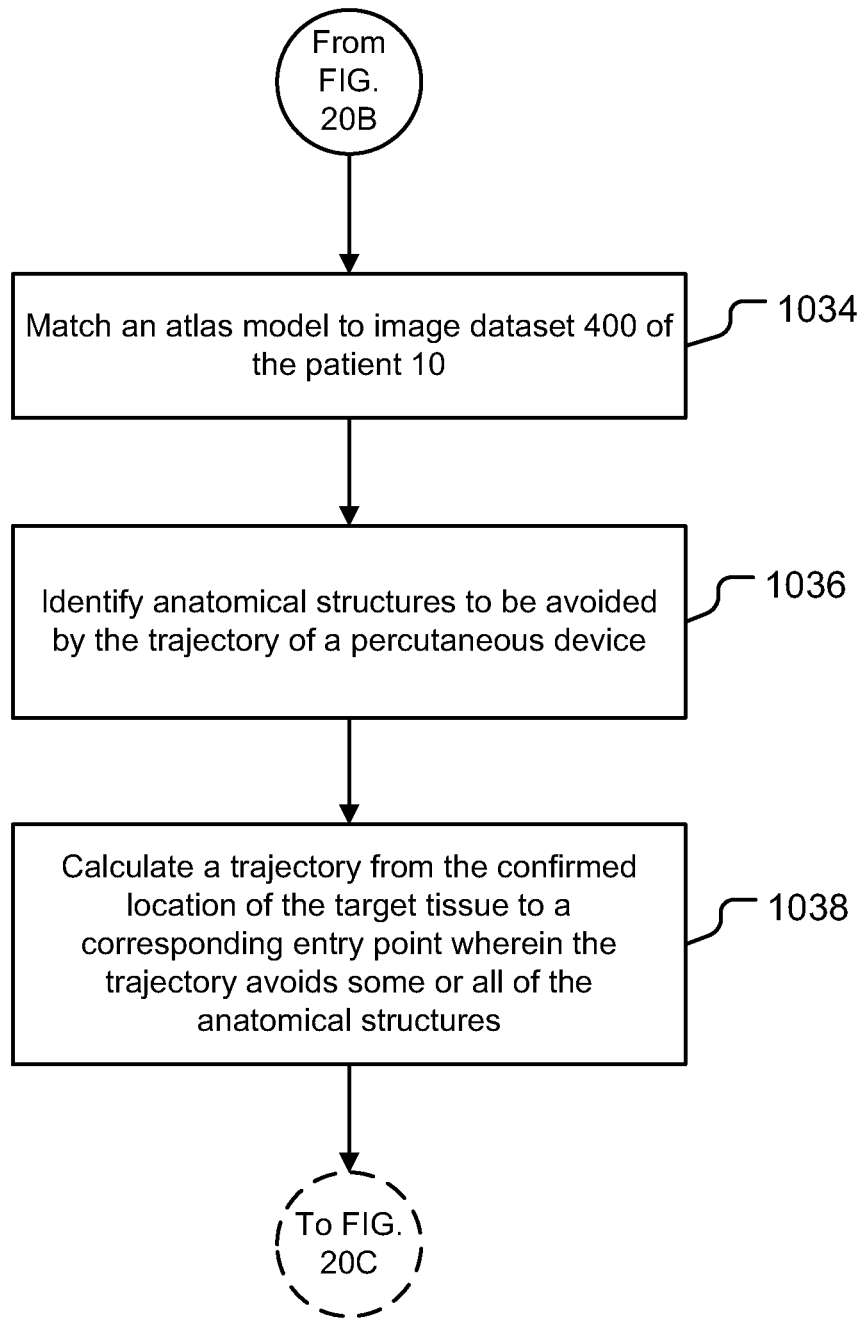
FIG. 20E is a flowchart illustrating a portion of a method of confirming the location of a target tissue according to an embodiment of the invention.

In various embodiments, the method as described in FIGS. 20A-20B may further include the steps outlined in FIG. 20E. In addition to or alternative to generating images of anatomical structures of patient 10 using imaging device 633 inserted into the airway of patient 10, one or more atlas models are employed to assist the procedure during the second time interval. The atlas model(s) are three-dimensional models of human anatomy and therefore include a variety of anatomical structures. The anatomical structures may include, but are not limited to, bone, the heart, the liver, other organs, fissures, diseased tissue, such as, for example, chronic obstructive pulmonary disease (COPD) lung tissue, and blood vessels. Accordingly, the anatomical structures may be any structure within the body of patient 10 that should be avoided, if possible, by percutaneous device (e.g., percutaneous needle 650). Additionally, the atlas model(s) may include weighted information related to the acceptability of a planned trajectory or planned ablation procedure to determine the optimal plan. This weighted information may include, but is not limited to, information regarding which anatomical structure(s) cannot be crossed by a medical device, information regarding avoid anatomical structure(s) by at least a given distance, and information regarding the heat sink effect of anatomical structure(s) so that ablation location and amount may be adjusted.

Thus as shown in FIG. 20E at step 1034, one or more atlas models is matched to image dataset 400 of patient 10 wherein the matching may comprise deforming the atlas model(s) to the image dataset 400 and/or registering the atlas model(s) to patient 10. At step 1036, navigation system 70 identifies anatomical structure(s) to be avoided by the trajectory of the percutaneous device. At step 1038, navigation system 70 may calculate and display a trajectory of the percutaneous device from the confirmed location of the target tissue to a corresponding entry point on the body of patient 10. This trajectory may avoid some or all of the anatomical structures. Accordingly, if a physician or other healthcare professional inserts percutaneous device, such as percutaneous needle 650, following this trajectory, percutaneous device may avoid some or all of the anatomical structures thereby preventing damage to the anatomical structure(s). Following the steps outlined in FIG. 20E, the method may optionally further include the steps illustrated in FIG. 20C.

In any of the embodiments of the methods described herein, a dye may be injected into the target tissue at the confirmed location using a needle inserted into working channel 608 of steerable catheter 600 or using a needle inserted into working channel 658 of percutaneous needle 650. Thus, when sampling the target tissue using a medical device inserted into working channel 658 of percutaneous needle 650, the presence of dye in the sample provides another indication that the correct target tissue was sampled. These additional steps may be helpful, for example, in lung resections where there is significant movement of the lungs of patient 10. For example, during lung resections there may be a gap between the chest wall and the lung and the physician or other healthcare profession may use a rigid scope to enter into patient 10. Because the confirmed target tissue was previously dyed using a needle inserted into working channel 608 of steerable catheter 600 or using a needle inserted into working channel 658 of percutaneous needle 650, the physician or other healthcare professional may be able to visually see the dye. This may assist the physician or healthcare professional in sampling and/or treating the correct target tissue.

Additionally, in various embodiments of the methods described herein, after tip 607 of steerable catheter 600 has been navigated proximate confirmed location of target tissue a sample of air proximate the confirmed location of the target tissue may be taken. Then cells, scents or other potential indicators of cancer within the air sample may then be analyzed to determine if the target tissue is cancerous. In certain embodiments, a breath analysis device may be inserted into working channel 608 of steerable catheter 600 and this breath analysis device may sample the air in situ. In other embodiments, a vacuum of air may be drawn on working channel 608 from port 616 to sample the air proximate the confirmed location of the target tissue may be taken. The vacuum may be created by a syringe inserted into port 616 or by some other suction device known in the art. In yet other embodiments, a sample of air proximate an airway segment near the confirmed location of the target tissue may be taken instead of, or in addition to, the sample taken proximate the confirmed location of the target.

Furthermore, in any of the embodiments of the methods described herein, navigation system 70 may be able to control a robotic medical device having a percutaneous needle. Navigation system 70 may be able to cause robotic medical device to navigate a percutaneous needle to the calculated entry point on the surface of patient 10. The percutaneous needle may then be inserted into patient 10 at the calculated entry point on the surface of patient 10 and the percutaneous needle may be extended to the confirmed location along the calculated trajectory. Thus, a robotic medical device may use information from navigation system 70 to perform any of the methods described herein.

The accompanying Figures and this description depict and describe certain embodiments of a navigation system (and related methods and devices) in accordance with the present invention, and features and components thereof. It should also be noted that any references herein to front and back, right and left, top and bottom and upper and lower are intended for convenience of description, not to limit the present invention or its components to any one positional or spatial orientation.

It is noted that the terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. Thus, a method, an apparatus, or a system that "comprises," "has," "contains," or "includes" one or more items possesses at least those one or more items, but is not limited to possessing only those one or more items. Individual elements or steps of the present methods, apparatuses, and systems are to be treated in the same manner.

The terms "a" and "an" are defined as one or more than one. The term "another" is defined as at least a second or more. The term "coupled" encompasses both direct and indirect connections, and is not limited to mechanical connections.

Those of skill in the art will appreciate that in the detailed description above, certain well known components and assembly techniques have been omitted so that the present methods, apparatuses, and systems are not obscured in unnecessary detail.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the patient tracking device, steerable catheter, percutaneous needle, and localization elements may be constructed from any suitable material, and may be a variety of different shapes and sizes, not necessarily specifically illustrated, while still remaining within the scope of the invention.

The invention claimed is:

1. A method of orienting an image feed on a display comprising:
   a) inserting an imaging device that provides the image feed into a channel of a steerable catheter, wherein the steerable catheter has a distal end portion and a localization element proximate the distal end portion;
   b) using the imaging device to generate a reference image feed of a reference of a known orientation;
   c) using a processor to determine a registered rotation angle θ by which the reference image feed must be rotated to obtain a registered orientation such that the reference in the reference image feed is matched to its known orientation when the reference image feed is rotated to the registered orientation;
   d) determining a localization element orientation of the localization element of the steerable catheter;
   e) determining a localization element angle β between the registered orientation and the localization element orientation; and
   f) using the processor and the determined localization element angle β to ensure that a real-time image feed from the imaging device is shown in an "up" orientation on the display as the steerable catheter is manipulated.

2. The method of claim 1, wherein the processor and the display form part of a navigation system, and further wherein the steerable catheter is navigated into an airway of a patient using the navigation.

3. The method of claim 1, wherein the step of using the processor to determine the registered rotation angle θ further comprises ensuring that no steering input is applied to the steerable catheter after generating the reference image feed of the reference while using the processor to determine the registered rotation angle θ.

4. The method of claim 2, wherein the reference comprises an anatomical feature of the airway of the patient.

5. The method of claim 2, further comprising overlaying a navigational aid onto the real-time image feed, wherein the navigational aid is registered to the real-time image feed.

6. The method of claim 2, further comprising displaying a virtual volumetric scene of the airway on the display and registering the virtual volumetric scene to the real-time image feed.

7. The method of claim 2, wherein the localization element orientation is determined by using the navigation system to determine the position and orientation of the localization element.

8. The method of claim 5, wherein the navigational aid is selected from a set of aids comprising a navigation pathway and a directional cue.

* * * * *